(12) United States Patent
Miyake et al.

(10) Patent No.: US 7,541,482 B2
(45) Date of Patent: Jun. 2, 2009

(54) PROCESS FOR PRODUCTION OF ALKYLTIN ALKOXIDES

(75) Inventors: Nobuhisa Miyake, Kurashiki (JP);
Kazuhiro Onishi, Kurashiki (JP);
Budianto Bijanto, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 348 days.

(21) Appl. No.: 11/596,885

(22) PCT Filed: May 18, 2005

(86) PCT No.: PCT/JP2005/009032

§ 371 (c)(1),
(2), (4) Date: Nov. 17, 2006

(87) PCT Pub. No.: WO2005/111049

PCT Pub. Date: Nov. 24, 2005

(65) Prior Publication Data

US 2008/0275262 A1  Nov. 6, 2008

(30) Foreign Application Priority Data

May 19, 2004  (JP) .............................. 2004-148710

(51) Int. Cl.
*C07F 7/22* (2006.01)
*C07C 69/96* (2006.01)

(52) U.S. Cl. .......................... 556/89; 502/152; 558/274; 558/277; 556/83

(58) Field of Classification Search .................. 556/83, 556/89; 558/274, 277; 502/152
See application file for complete search history.

(56) References Cited

U.S. PATENT DOCUMENTS

| | | | |
|---|---|---|---|
| 2,700,675 A | 1/1955 | Mack et al. | |
| 3,470,221 A | 9/1969 | Chadha et al. | |
| 3,651,015 A * | 3/1972 | Ishida et al. | 528/223 |
| 3,745,219 A * | 7/1973 | Baum et al. | 514/493 |
| 4,554,110 A * | 11/1985 | Mark | 558/270 |
| 5,545,600 A | 8/1996 | Knudsen et al. | |
| 5,759,941 A * | 6/1998 | Saleh | 502/152 |
| 2005/0240045 A1 * | 10/2005 | Miyake et al. | 558/270 |

FOREIGN PATENT DOCUMENTS

| | | |
|---|---|---|
| EP | 1 460 056 | 9/2004 |
| JP | 2003-192643 | 7/2003 |
| JP | 2003-192644 | 7/2003 |
| NL | 6612421 | 3/1967 |
| TW | 200407346 | 5/2004 |
| TW | 200407384 | 5/2004 |
| WO | 03/055840 | 7/2003 |

OTHER PUBLICATIONS

Office Action issued in corresponding Taiwanese Patent Application No. 094116363 on Jan. 3, 2008.
English Abstract for Journal of the Chemical Society of Japan, Industrial Chemistry Section, May 1969, vol. 72, No. 5, pp. 1543-1549.
Journal of the Chemical Society of Japan, Industrial Chemistry Section, May 1969, vol. 72, No. 5, pp. 1543-1549.
International Search Report dated Jul. 5, 2005 (International Application No. PCT/JP2005/009032, filed on May 18, 2005). (4 pp).

* cited by examiner

*Primary Examiner*—Porfirio Nazario Gonzalez
(74) *Attorney, Agent, or Firm*—Staas & Halsey LLP

(57) ABSTRACT

A process for the production of alkyltin alkoxides which comprises subjecting at least one alkyltin compound selected from among organotin compounds having tin-oxygen-tin linkages as the starting compound and a hydroxyl compound as the reactant to dehydration to obtain an alkyltin alkoxide corresponding to the starting compound and the reactant, characterized by continuously feeding the starting compound and the reactant into a reactor, discharging a water-containing low boiling point component from the reactor, and continuously withdrawing a reaction fluid containing an alkyltin alkoxide as the bottom from the reactor.

26 Claims, 7 Drawing Sheets

PROCESS FOR PRODUCTION OF ALKYLTIN ALKOXIDES

CROSS REFERANCE TO RELATED APPLICATIONS

This application claims the benefit under 35 U.S.C. Section 371, of PCT international Application Number PCT/JP2005/009032, filed May 18, 2005 and Japanese Application No. 2004-148710, filed May 19, 2004 in Japan, the contents of which are incorporated herein by referance.

TECHNICAL FIELD

The present invention relates to a process for production of alkyltin alkoxides, a process for production of carbonate ester or isocyanate using, as a catalyst, a dialkyltin alkoxide obtained by the above described production process, and carbonate ester or isocyanate produced by the above described process.

BACKGROUND ART

Alkyltin alkoxides are very useful as catalysts for the synthesis or transesterification of esters or the curing reaction of silicon polymer or urethane.

Currently used processes for production of alkyltin alkoxides include: for example, the process which uses a dialkyldichlorotin as a raw material (see, for example, Patent Reference 1); and the process which uses a dialkyltin oxide as a raw material (see, for example, Patent Reference 2). The former process, which uses a dialkyldichlorotin as a raw material, uses a high-cost metal alcoholate as a secondary material. In addition, it produces two moles of metal salt per one mole of dialkyltin alkoxide, as an aimed product, as shown in the following reaction equation (8), which causes problems of wastes or the like. Thus, use of the former process as an industrial production process still poses problems, including high production cost and waste production.

[Formula 1]

(8)

The latter process, which uses a dialkyltin oxide as a raw material, is preferable in that it does not produce a large amount of wastes. Thus, investigations have been made of producing dialkyltin alkoxides using the latter process. One example of such production processes is such that it produces a dialkyltin alkoxide from dibutyltin oxide and an alcohol by a two-stage reaction, as shown in the following reaction equation (9) (see Patent Reference 3). In the first stage, dibutyltin oxide and an alcohol are allowed to react in benzene or toluene at a temperature in the range of 80° C. to 110° C., followed by removal of formed water by azeotropic distillation, to produce 1,1,3,3-tetrabutyl-1,3-dialkoxy-distannoxane. In the second stage, the above described distannoxane is subjected to disproportionation at a temperature in the range of 180° C. to 220° C., followed by distillation, to produce a dibutyltin dialkoxide. This process is superior in that it does not produce wastes; however, the disproportionation in the second stage of the process involves the distillation of a high boiling point dialkyltin alkoxide under a high temperature, and therefore consuming a significant amount of energy. Thus, use of the latter process as an industrial production process still poses problems, including high energy consumption. Further, the process has a low productivity.

[Formula 2]

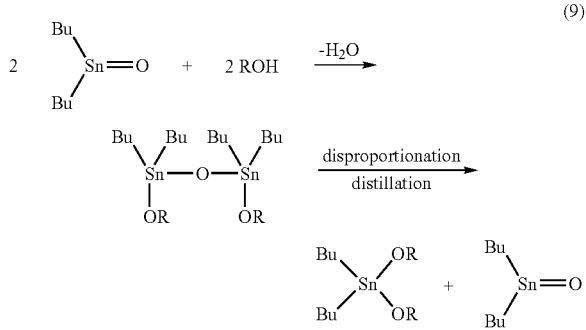

(9)

As a process for producing a dialkyltin dialkoxide directly from a dialkyltin oxide and an alcohol, a process is disclosed in which a high boiling point alcohol is used, as shown in the following reaction equation (10) (see Patent Reference 2). In this process, the reaction is performed at a temperature higher than that of the case where the reaction is performed in benzene or toluene, since it is performed at the boiling point of the alcohol as a reactant, followed by removal of the formed water, as an azeotropic mixture of water and alcohol as a reactant. This process is superior to the above described process in that it does not require the heat distillation of a high boiling point dialkyltin dialkoxide. However, since the reaction temperature is the boiling point of the alcohol as a reactant, the reaction rate is low for the alcohols with a small number of carbon atoms and even for the alcohols with a large number of carbon atoms. Thus the process has a low productivity.

[Formula 3]

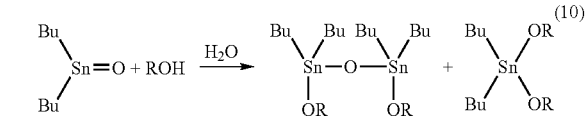

(10)

Further, in the above described process, since the reaction was performed in a high boiling point alcohol at a high temperature, a large amount of trialkyltin compound, which is probably produced in accordance with the following reaction equation (11), is actually produced. In fact, it is well known that trialkyltin compounds are produced by the pyrolysis of dialkyltin alkoxides (see Non-Patent Reference 1), and the trialkyltin compound may form a complex mixture of reaction by-products, other than the dialkyltin dialkoxide which the present invention is aiming at. Thus, this process is not preferable, either, as an industrial production process.

[Formula 4]

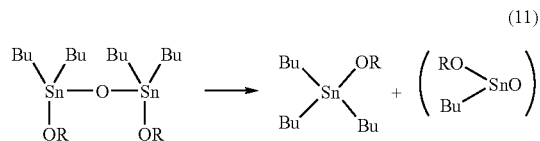

(11)

To increase the productivity, which is one of the problems the above described processes have, there is disclosed a process which uses an alcohol and a carbonate ester as reactants, as shown in the reaction equation (12) (see Patent Reference 2). This process involves the use of high cost carbonate ester as a reactant, though it improves the productivity the above described processes have; thus, use of this process still poses problems, including high production cost.

[Formula 5]

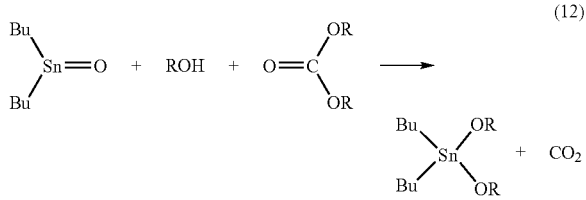

(12)

[Patent Reference 1] U.S. Pat. No. 2,700,675
[Patent Reference 2] U.S. Pat. No. 5,545,600
[Patent Reference 3] NL-6612421
[Non-Patent Reference 1] Journal of the Society of Chemical Industry, 72,7 (1969), 1543

DISCLOSURE OF THE INVENTION

Problems to be Solved by the Invention

As described above, in conventional processes for production of alkyltin alkoxides, when intending to increase the productivity, it is inevitable to use high cost raw materials. In such circumstances, there have been demands for a convenient and highly productive process for production of alkyltin alkoxides.

Accordingly, the object of the present invention is to provide a process for industrially producing alkyltin alkoxides, in particular, a process for industrially and continuously producing alkyltin alkoxides.

Means for Solving the Problems

After directing tremendous research effort toward overcoming the above described problems, the present inventors have found that if a starting material, which is selected from the group consisting of organotin compounds each having a tin-oxygen-tin bond, and a hydroxy compound, as a reactant, are continuously supplied to a reactor, and low boiling point components, which result from the reaction, are continuously removed from the reactor, a reaction solution that contains an alkyltin alkoxide corresponding to the starting material and the reactant can be continuously taken out from the reactor, as a component remaining in the bottom of the reactor. Thus the inventors achieved the completion of the present invention.

Specifically, the present invention is as follows:

[1] A process for production of alkyltin alkoxides, including subjecting at least one alkyltin compound, as a starting material, which is selected from the group consisting of organotin compounds each having a tin-oxygen-tin bond and a hydroxy compound, as a reactant, to dehydration reaction to produce an alkyltin alkoxide corresponding to the starting material and the reactant, characterized in that the starting material and the reactant are continuously supplied to a reactor; low boiling point components containing water are taken out from the reactor; and a reaction solution, as a component in the bottom of the reactor, which contains the alkyltin alkoxide is continuously taken out from the reactor.

[2] The process according to the above item [1], characterized in that the above described at least one alkyltin compound, as a starting material, is a tetraalkyl-dialkoxy-1,3-distannoxane and/or dialkyltin oxide generally existing in the form of a polymer resulting from polymerization via a tin-oxygen-tin bond.

[3] The process according to the above item [2], characterized in that the tetraalkyl-dialkoxy-1,3-distannoxane is a tetraalkyl-dialkoxy-1,3-distannoxane represented by the following chemical formula (1):

[Formula 6]

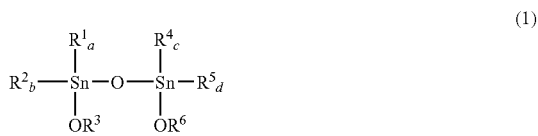

(1)

wherein $R^1$, $R^2$, $R^4$ and $R^5$ each independently represent an alkyl group, aralkyl group or aryl group; $R^3$ and $R^6$ each represent an alkyl group or aralkyl group; a and b are integers of 0 to 2, a+b being 2; and c and d are integers of 0 to 2, c+d being 2.

[4] The process according to the above item [2], characterized in that the above described dialkyltin oxide is a polymer of a dialkyltin oxide represented by the following chemical formula (2):

[Formula 7]

(2)

wherein $R^7$ and $R^8$ each independently represent an alkyl group, aralkyl group or aryl group; and e and f are integers of 0 to 2, e+f being 2.

[5] The process according to the above item [2], wherein the above described starting material is any one selected from a monomer, a dimer (aggregate of the same monomer or aggregate of different monomers), an oligomer or a polymer.

[6] The process according to the above item [1], characterized in that the above described hydroxy compound is an alcohol represented by the following chemical formula (3):

[Formula 8]

$R^9OH$ (3)

wherein R⁹ represents an n-butyl group, a 2-methylpropyl group, a linear or branched alkyl group with 5 to 12 carbon atoms, a cycloalkyl group with 5 to 12 carbon atoms, a linear or branched alkenyl group with 2 to 12 carbon atoms, a substituted or unsubstituted aryl with 6 to 19 carbon atoms, or aralkyl group with 7 to 20 carbon atoms that contains an alkyl selected from the group consisting of a linear or branched alkyl with 1 to 14 carbon atoms and a cycloalkyl with 5 to 14 carbon atoms.

[7] The process according to the above item [6], characterized in that the above described alcohol is selected from the group consisting of 1-butanol, 2-methyl-1-propanol and alkyl alcohol with 5 to 8 carbon atoms.

[8] The process according to the above item [1], including the step of: continuously supplying the starting material and the reactant to a reactor to allow them to undergo a dehydration reaction in a liquid phase or in a gas-liquid phase in the reactor; and at the same time, taking out a high boiling point reaction mixture, in the form of a liquid, that contains the produced alkyltin alkoxide or alkyltin alkoxide mixture from the bottom of the reactor, while continuously removing, from the reactor, a low boiling point reaction mixture containing the produced water in the form of a gas by distillation.

[9] The process according to the above item [1] or [8], wherein the reactor includes: lines for supplying the above described starting material and the above described reactant, respectively, or a line for supplying the mixed solution of the above described starting material and the above described reactant; a line for removing the low boiling point reaction mixture containing water; and a line for taking out the high boiling point reaction mixture.

[10] The process according to the above item [9], wherein the line for removing the low boiling point reaction mixture containing water is in a position where gas-phase components are removed, while the line for taking out the high boiling point reaction mixture is in a lower position where the liquid-phase component is taken out.

[11] The process according to any one of the above items [1] to [10], wherein the above described reactor is a tank reactor or a column reactor.

[12] The process according to any one of the above items [1] to [11], wherein the above described reactor is a type that includes a stirring tank, a multistage stirring tank, a distillation column, a multistage distillation column, a continuous multistage distillation column, a packed column, a thin film evaporator, a reactor with a support in its inside, forced circulation reactor, a falling film evaporator, a falling drop evaporator, a trickle bed reactor or a bubble column.

[13] The process according to any one of the above items [1] to [12], wherein an inert gas and/or a gaseous reactant and/or a gaseous inert organic compound and/or an organic solvent that forms an azeotropic mixture with water are supplied to the reactor.

[14] The process according to the above item [13], wherein the inert gas is selected from nitrogen, carbon dioxide and argon.

[15] The process according to the above item [1], wherein the above described dehydration reaction is performed at a temperature in a range of 60° C. to 160° C.

[16] The process according to the above item [1], wherein a ratio of the total mole number of tin atoms contained in the starting material to the mole number of the reactant, as the ratio of the starting material to the reactant, is in a range of 3 to 100.

[17] The process according to any one of the above items [4] to [16], characterized in that the dehydration reaction is performed at a dehydration rate represented by the following expression (4):

[Expression 1]

$$\text{Dehydration rate} > \frac{60X + 10Y}{A^{-1} \cdot \exp\left(\frac{B}{R \cdot T}\right)} \quad (4)$$

wherein the dehydration rate means the amount of the water that is formed by the dehydration reaction and drawn out of the system per unit time [mol·hr⁻¹]; X represents the total mole number [mol] of tin atoms contained in the alkyltin compound represented by the general formula (2) which is contained in the starting material; Y represents the total mole number [mol] of tin atoms contained in the alkyltin compound represented by the general formula (1) which is contained in the starting material; T represents a temperature [K] at which the dehydration reaction is performed; R represents a gas constant=8.314 J·mol⁻¹·K⁻¹; and A and B are coefficients depending on the kind of alkyltin compound, wherein coefficients A and B in the above described expression (4) depend on the kind of alkyltin compound as the starting material and are obtained based on the set primary standard substance. When the starting material contains an alkyltin compound represented by the chemical formula (1), the above described coefficients A and B represent a frequency factor and an activation energy of a pyrolytic reaction of the primary standard substance which is an alkyltin compound arbitrarily selected from the alkyltin compounds represented by the chemical formula (1) and contained in the starting material, and are obtained from the following equation (5). When the starting material does not contain an alkyltin compound represented by the chemical formula (1), but contains an alkyltin compound represented by the chemical formula (2), the above described coefficients A and B represent a frequency factor and an activation energy of a pyrolytic reaction of the primary standard substance which is an alkyltin alkoxide arbitrarily selected from the alkyltin alkoxides represented by the following chemical formula (7) formed from the alkyltin compounds represented by the following chemical formula (2) contained in the starting material and the reactant, and are obtained from the following equation (5).

[Expression 2]

$$k = A \cdot \exp\left(-\frac{B}{R \cdot T}\right) \quad (5)$$

wherein k represents a first-order rate constant [hr⁻¹]; A represents a frequency factor [hr⁻¹]; B represents an activation energy [J·mol⁻¹]; R represents a gas constant=8.314 J·mol⁻¹·K⁻¹; and T represents a temperature [K] at which the pyrolytic reaction is performed. The above described k represents first-order rate constant of the pyrolytic reaction which is obtained by the following equation (6):

[Expression 3]

$$k \cdot t = -\ln(1-X) \quad (6)$$

wherein k represents first-order rate constant [hr$^{-1}$]; t represents a heating time; and X [hr] represents a reduction ratio [mol/mol] with respect to the initial concentration of a primary standard substance,

[Formula 9]

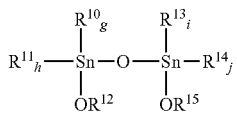

(7)

wherein $R^{10}$, $R^{11}$, $R^{13}$ and $R^{14}$ correspond to either $R^7$ or $R^8$ of the starting material; g, h, i and j correspond to either e or f of the starting material; at least one of $R^{12}$ and $R^{15}$ corresponds to $R^9$ of the reactant; g and h are integers of 0 to 2, g+h=2; and i and j are integers of 0 to 2, i+j=2.

[18] A process for production of a carbonate ester characterized by using a dialkyltin alkoxides, as a catalyst, produced by the process according to any one of the above items [1] to [17].

[19] A carbonate ester produced using, as a catalyst, a dialkyltin alkoxide produced by the process according to any one of the above items [1] to [17].

[20] An isocyanate produced using the carbonate ester according to the above item [19].

[21] A polycarbonate produced using the carbonate ester according to the above item [19].

Effect of the Invention

In the process for production of alkyltin alkoxides according to the present invention, a starting material and a reactant are continuously subjected to dehydration reaction, and at the same time, the formed water and products are continuously being drawn out of the system, whereby alkyltin alkoxides can be produced with high productivity. Thus, the process is very useful for industrial application.

Best Mode for Carrying out the Invention

The present invention is characterized by continuously supplying a starting material that contains a dialkyltin oxide and/or a tetraalkyl-dialkoxy-distannoxane and a reactant, a hydroxy compound, to a reactor and taking out the low boiling point components containing water from the reactor to continuously obtain a reaction solution, as the component in the bottom of the reactor, which contains an alkyltin alkoxide corresponding to the starting material and the reactant.

The present inventors have presumed that the reaction of a dialkyltin oxide with an alcohol that produces a dialkyltin alkoxide is based on the equilibrium reactions represented by the following reaction equations (13) and (14.)

[Formula 10]

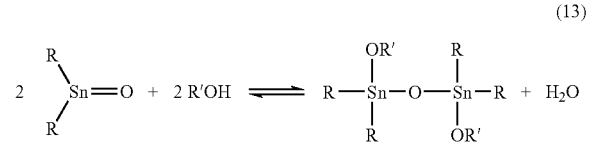

(13)

[Formula 11]

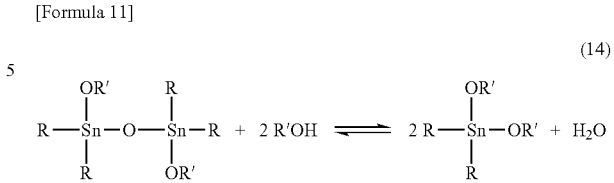

(14)

Conventionally, the above described reaction has been carried out by batch process, while distilling away the formed water at atmospheric pressure or under reduced pressure. The reason is that, since the equilibrium in the reactions represented by the formulae (13) and (14) inclines to the left (reactants), it is necessary to make the equilibrium to shift to the right (products) and take the formed water out of the system so that the reaction progresses. At the same time, to increase the reaction rate, the above reaction has been carried out at high temperatures.

As a result, when using an alcohol with a large number of carbon atoms and a high boiling point as a reactant in the above described reaction, the reaction progresses in several hours, whereas when using an alcohol with a small number of carbon atoms and a low boiling point as a reactant so as to produce a dialkyltin alkoxide corresponding to the alcohol, the productivity is significantly low. It is known that the reaction represented by the reaction formula (13), that is, the dehydration reaction of a dialkyltin oxide with an alcohol to produce a tetraalkyl-dialkoxy-distannoxane quantitatively progresses relatively easily even by conventional processes. However, in the reaction represented by the reaction formula (14), since the equilibrium inclines significantly to the left (reactants), the water formed by the reaction rapidly reacts with the formed dialkyltin dialkoxide; thus, a dialkyltin dialkoxide cannot be obtained with high productivity. To obtain an increased amount of intended product in the reaction represented by the reaction formula (14), it is necessary to use a large amount of hydroxy compound. Use of a large amount of hydroxy compound certainly makes it possible to enhance the conversion of a tetraalkyl-dialkoxy-1,3-distannoxane to a dialkyltin dialkoxide; however, it requires a huge reactor, and moreover, a large amount of unreacted hydroxy compound to be removed by distillation; consequently, it cannot increase the productivity.

After intensive examination of conventional processes, the present inventors have found that in the above described conventional techniques, a large amount of tributyltin compound, which is not an intended compound, is produced since the reaction is carried out at high temperatures and for a long time, though this is not clearly described in the documents. Specifically, the reaction by conventional batch process has a serious problem of causing by-production of a trialkylin compound, as described above (FIG. 1 shows the change with time in pyrolysis of 1,1,3,3-tetrabutyl-1,3-bis(2-ethylhexyloxy)-distannoxane) into a tributyltin compound), because an alkyltin alkoxide as a starting material or as a product resides in the reactor due to its low reaction rate and its batch reaction.

After directing tremendous research effort toward solution of the above described problem, the present inventors have found that when employing a process that includes: continuously supplying a starting material, which is selected from the group consisting of dialkyltin oxides, tetraalkyl-dialkoxy-distannoxanes and the mixtures thereof, and a reactant, a hydroxy compound, to a reactor; taking out the low boiling point components from the reactor; and continuously taking out the reaction solution, as the component in the bottom of the reactor, which contains an alkyltin alkoxide corresponding to the starting material and the reactant, surprisingly, the reaction time is short and the productivity is high, compared with conventional batch processes; moreover, the above described by-production of a tributyltin compound is inhibited.

Specifically, the present inventors came up with an idea that the rate of producing alkyltin alkoxides by conventional batch processes was largely restricted by the rate of removing the formed water, and then they have found that a process, as a process for overcoming the problem, which includes: rapidly and continuously removing the formed water from the system; and at the same time, rapidly and continuously taking out the resultant product, an alkyltin alkoxide, from the system makes it possible to produce a dialkyltin alkoxide with high productivity. They have also found that the process of the present invention enables the formation of an unintended compound, a tributyltin compound, to be reduced.

First, the raw materials used in the present invention will be described.

The starting material is a composition that contains a dialkyltin oxide and/or a tetraalkyl-dialkoxy-distannoxane. The composition may contain a tetraalkyl-dialkoxy-distannoxane alone or an arbitrary amount of dialkyltin oxide, which is the precursor of tetraalkyl-dialkoxy-distannoxane. Specifically, both the reaction represented by the reaction formula (13) whereby a tetraalkyl-dialkoxy-distannoxane is obtained from a dialkyltin oxide and the reaction represented by the reaction formula (14) whereby a dialkyltin dialkoxide is obtained from a tetraalkyl-dialkoxy-distannoxane are the same dehydration reaction; therefore, a dialkyltin alkoxide can be obtained even from a starting material that contains an arbitrary amount of dialkyltin oxide.

Tetraalkyl-dialkoxy-distannoxanes used in the present invention may be the tetraalkyl-dialkoxy-distannoxanes represented by the following chemical formula (1), and they may be monomers, aggregates, oligomers or polymers having a structural formula represented by the chemical formula (1).

[Formula 12]

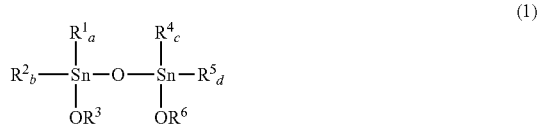

(1)

wherein $R^1$, $R^2$, $R^4$ and $R^5$ each independently represent an alkyl group, aralkyl group or aryl group; $R^3$ and $R^6$ each represent an alkyl group or aralkyl group; a and b are integers of 0 to 2, a+b being 2; and c and d are integers of 0 to 2, c+d being 2.

Examples of $R^1$, $R^2$, $R^4$ and $R^5$ in the tetraalkyl-dialkoxy-distannoxanes represented by the chemical formula (1) include: alkyl groups as aliphatic hydrocarbon groups with 1 to 12 carbon atoms and cycloalkyl groups as aliphatic hydrocarbon groups with 5 to 12 carbon atoms, such as methyl, ethyl, propyl, butyl (its isomers), pentyl (its isomers), hexyl (its isomers), heptyl (its isomers), octyl (its isomers), nonyl (its isomers), decyl (its isomers), undecyl (its isomers), dodecyl (its isomers), 2-butenyl, cyclobutenyl, cyclobutyl, cyclopentyl, cyclohexyl, cyclopentyl, cyclopentadienyl and cyclohexenyl groups; aralkyl groups with 7 to 20 carbon atoms, such as benzyl and phenylethyl groups; and aryl groups with 6 to 20 carbon atoms, such as phenyl, tolyl and naphthyl groups. They may contain an ether linkage or may be halogenated hydrocarbon groups in which all of or part of hydrogen atoms of each hydrocarbon group are replaced by halogen atoms, such as nonafluorobutyl and heptafluorobutyl (their isomers); however, they are not limited to these examples. Preferably, $R^1$, $R^2$, $R^4$ and $R^5$ are lower alkyl groups. More preferably, they are linear or branched alkyl groups with 1 to 8 carbon atoms. The above described kinds of groups with more carbon atoms than those described above can also be used; however, they sometimes impair the flowability or the productivity of dialkyltin alkoxides. $R^1$, $R^2$, $R^4$ and $R^5$ in the tetraalkyl-dialkoxy-distannoxanes represented by the chemical formula (1) may be the same or different.

$R^3$ and $R^6$ represent a linear or branched alkyl group with 1 to 12 carbon atoms, cycloalkyl group with 5 to 12 carbon atoms or linear or branched alkenyl group with 2 to 12 carbon atoms, and an aralkyl groups with 7 to 20 carbon atoms that includes a substituted or unsubstituted aryl with 6 to 19 carbon atoms and an alkyl group selected from the group consisting of linear or branched alkyls with 1 to 14 carbon atoms and cycloalkyls with 5 to 14 carbon atoms. They may contain an ether linkage or may be halogenated hydrocarbon groups in which all of or part of hydrogen atoms of each hydrocarbon group are replaced by halogen atoms, such as nonafluorobutyl and heptafluorobutyl (their isomers); however, they are not limited to these examples. Preferably, $R^3$ and $R^6$ are lower alkyl groups. More preferably, they are n-butyl group, 2-methylpropyl group or linear or branched alkyl groups with 5 to 9 carbon atoms. The above described kinds of groups with a larger number of carbon atoms than those described above can also be used; however, they sometimes impair the flowability or the productivity of dialkyltin alkoxides. $R^3$ and $R^6$ in the tetraalkyl-dialkoxy-distannoxanes represented by the chemical formula (1) may be the same or different.

Examples of tetraalkyl-dialkoxy-distannoxanes represented by the chemical formula (1) include: tetraalkyl-dialkoxy-distannoxanes and tetraalkyl-diaralkyloxy-distannoxanes, such as 1,1,3,3-tetramethyl-1,3-di(n-butoxy)-distannoxane, 1,1,3,3-tetramethyl-1,3-bis(2-methylpropyloxy)-distannoxane, 1,1,3,3-tetramethyl-1,3-di-pentyloxy-distannoxane (its isomers), 1,1,3,3-tetramethyl-1,3-di-hexyloxy-distannoxane (its isomers), 1,1,3,3-tetramethyl-1,3-di-heptyloxy-distannoxane-(its isomers), 1,1,3,3-tetramethyl-1,3-di-octyloxy-distannoxane (its isomers), 1,1,3,3-tetramethyl-1,3-di-nonyloxy-distannoxane (its isomers), 1,1,3,3-tetramethyl-1,3-di-decyloxy-distannoxane (its isomers), 1,1,3,3-tetramethyl-1,3-di-bezyloxy-distannoxane, 1,1,3,3-tetramethyl-1,3-di-phenylethoxy-distannoxane, 1,3-dibutyl-1,3-dimethyl-1,3-di(n-butoxy)-distannoxane, 1,3-dibutyl-1,3-dimethyl-1,3-bis(2-methylpropyl)-distannoxane, 1,3-dibutyl-1,3-dimethyl-1,3-di-pentyloxy-distannoxane (its isomers), 1,3-dibutyl-1,3-dimethyl-1,3-di-hexyloxy-distannoxane (its isomers), 1,3-dibutyl-1,3-dimethyl-1,3-di-heptyloxy-distannoxane (its isomers), 1,3-dibutyl-1,3-dimethyl-1,3-di-octyloxy-distannoxane (its isomers), 1,3-dibutyl-1,3-dimethyl-1,3-di-nonyloxy-distannoxane (its isomers), 1,3-dibutyl-1,3-dimethyl-1,3-di-decyloxy-distannoxane (its isomers), 1,3-dibutyl-1,3-dimethyl-1,3-di-benzyloxy-distannoxane, 1,3-dibutyl-1,3-dimethyl-1,3-di-phenylethoxy-distannoxane, 1,3-dibutyl-1,3-diethyl-1,3-di(n-butoxy)-distannoxane, 1,3-dibutyl-1,3-diethyl-1,3-bis(2-methylpropyl)-distannoxane, 1,3-dibutyl-1,3-diethyl-1,3-di-pentyloxy-distannoxane (its isomers), 1,3-dibutyl-1,3-diethyl-1,3-di-hexyloxy-distannoxane (its isomers), 1,3-dibutyl-1,3-diethyl-1,3-di-heptyloxy-distannoxane (its isomers), 1,3-dibutyl-1,3-diethyl-1,3-di-octyloxy-distannoxane (its isomers), 1,3-dibutyl-1,3-diethyl-1,3-di-nonyloxy-distannoxane (its isomers), 1,3-dibutyl-1,3-diethyl-1,3-di-decyloxy-distannoxane (its isomers), 1,3-dibutyl-1,3-diethyl-1,3-di-benzyloxy-distannoxane, 1,3-dibutyl-1,3-diethyl-1,3-di-phenylethoxy-distannoxane, 1,3-dibutyl-1,3-dipropyl-1,3-di(n-butoxy)-distannoxane, 1,3-dibutyl-1,3-dipropyl-1,3-bis(2-methylpropyl)-distannoxane (its isomers), 1,3-dibutyl-1,3-dipropyl-1,3-di-pentyloxy-distannoxane (its isomers), 1,3-dibutyl-1,3-dipropyl-1,3-di-hexyloxy-distannoxane (its isomers), 1,3-dibutyl-1,3-dipropyl-1,3-di-heptyloxy-distannoxane (its isomers), 1,3-dibutyl-1,3-dipropyl-1,3-di-octyloxy-distannoxane (its isomers), 1,3-dibutyl-1,3-dipropyl-1,3-di-nonyloxy-distannoxane (its isomers), 1,3-dibutyl-1,3-dipropyl-1,3-di-decyloxy-distannoxane (its isomers), 1,3-dibutyl-1,3-dipropyl-1,3-di-benzyloxy-distannoxane, 1,3-dibutyl-1,3-dipropyl-1,3-di-phenylethoxy-distannoxane, 1,1,3,3-tetrabutyl-1,3-di(n-butoxy)-distannoxane, 1,1,3,3-tetrabutyl-1,3-bis(2-methylpropyl)-distannoxane (its isomers), 1,1,3,3-tetrabutyl-1,3-di-pentyloxy-distannoxane (its isomers), 1,1,3,3-tetrabutyl-1,3-di-hexyloxy-distannoxane (its isomers), 1,1,3,3-tetrabutyl-1,3-di-heptyloxy-distannoxane (its isomers), 1,1,3,3-tetrabutyl-1,3-di-octyloxy-distannoxane (its isomers), 1,1,3,3-tetrabutyl-1,3-di-nonyloxy-distannoxane (its isomers), 1,1,3,3-tetrabutyl-1,3-di-decyloxy-distannoxane (its isomers), 1,1,3,3-tetrabutyl-1,3-di-bezyloxy-distannoxane, 1,1,3,3-tetrabutyl-1,3-di-phenylethoxy-distannoxane, 1,1,3,3-tetraphenyl-1,3-di(n-butoxy)-distannoxane, 1,1,3,3-tetraphenyl-1,3-bis(2-methylpropyl)-distannoxane, 1,1,3,3-tetraphenyl-1,3-di-pentyloxy-distannoxane (its isomers), 1,1,3,3-tetraphenyl-1,3-di-hexyloxy-distannoxane (its isomers), 1,1,3,3-tetraphenyl-1,3-di-heptyloxy-distannoxane (its isomers), 1,1,3,3-tetraphenyl-1,3-di-octyloxy-distannoxane (its isomers), 1,1,3,3-tetraphenyl-1,3-di-nonyloxy-distannoxane (its isomers), 1,1,3,3-tetraphenyl-1,3-di-decyloxy-distannoxane (its isomers), 1,1,3,3-tetraphenyl-1,3-di-bezyloxy-distannoxane, 1,1,3,3-tetraphenyl-1,3-di-phenylethoxy-distannoxane, 1,1,3,3-tetra(trifluorobutyl)-1,3-di(n-butoxy)-distannoxane, 1,1,3,3-tetra(trifluorobutyl)-1,3-bis(2-methylpropyl)-distannoxane (its isomers), 1,1,3,3-tetra(trifluorobutyl)-1,3-di-pentyloxy-distannoxane (its isomers), 1,1,3,3-tetra(trifluorobutyl)-1,3-di-hexyloxy-distannoxane (its isomers), 1,1,3,3-tetra(trifluorobutyl)-1,3-di-heptyloxy-distannoxane (its isomers), 1,1,3,3-tetra(trifluorobutyl)-1,3-di-octyloxy-distannoxane (its isomers), 1,1,3,3-tetra(trifluorobutyl)-1,3-di-nonyloxy-distannoxane (its isomers), 1,1,3,3-tetra(fluorobutyl)-1,3-di-decyloxy-distannoxane (its isomers), 1,1,3,3-tetra(trifluorobutyl)-1,3-di-bezyloxy-distannoxane, 1,1,3,3-tetra(trifluorobutyl)-1,3-di-phenylethoxy-distannoxane, 1,1,3,3-tetra(pentafluorobutyl)-1,3-di(n-butoxy)-distannoxane, 1,1,3,3-tetra(pentafluorobutyl)-1,3-bis(2-methylpropyl)-distannoxane, 1,1,3,3-tetra(pentafluorobutyl)-1,3-di-pentyloxy-distannoxane (its isomers), 1,1,3,3-tetra(pentafluorobutyl)-1,3-di-hexyloxy-distannoxane (its isomers), 1,1,3,3-tetra(pentafluorobutyl)-1,3-di-heptyloxy-distannoxane (its isomers), 1,1,3,3-tetra(pentafluorobutyl)-1,3-di-octyloxy-distannoxane (its isomers), 1,1,3,3-tetra(pentafluorobutyl)-1,3-di-nonyloxy-distannoxane (its isomers), 1,1,3,3-tetra(pentafluorobutyl)-1,3-di-decyloxy-distannoxane (its isomers), 1,1,3,3-tetra(pentafluorobutyl)-1,3-di-bezyloxy-distannoxane, 1,1,3,3-tetra(pentafluorobutyl)-1,3-di-phenylethoxy-distannoxane, 1,1,3,3-tetra(heptafluorobutyl)-1,3-di(n-butoxy)-distannoxane, 1,1,3,3-tetra(heptafluorobutyl)-1,3-bis(2-methylpropyl)-distannoxane (its isomers), 1,1,3,3-tetra(heptafluorobutyl)-1,3-di-pentyloxy-distannoxane (its isomers), 1,1,3,3-tetra(heptafluorobutyl)-1,3-di-hexyloxy-distannoxane (its isomers), 1,1,3,3-tetra(heptafluorobutyl)-1,3-di-heptyloxy-distannoxane (its isomers), 1,1,3,3-tetra(heptafluorobutyl)-1,3-di-octyloxy-distannoxane (its isomers), 1,1,3,3-tetra(heptafluorobutyl)-1,3-di-nonyloxy-distannoxane (its isomers), 1,1,3,3-tetra(heptafluorobutyl)-1,3-di-decyloxy-distannoxane (its isomers), 1,1,3,3-tetra(heptafluorobutyl)-1,3-di-bezyloxy-distannoxane, 1,1,3,3-tetra(heptafluorobutyl)-1,3-di-phenylethoxy-distannoxane, 1,1,3,3-tetra(nonafluorobutyl)-1,3-di(n-butoxy)-distannoxane, 1,1,3,3-tetra(nonafluorobutyl)-1,3-bis(2-methylpropyl)-distannoxane, 1,1,3,3-tetra(nonafluorobutyl)-1,3-di-pentyloxy-distannoxane (its isomers), 1,1,3,3-tetra(nonafluorobutyl)-1,3-di-hexyloxy-distannoxane (its isomers), 1,1,3,3-tetra(nonafluorobutyl)-1,3-di-heptyloxy-distannoxane (its isomers), 1,1,3,3-tetra(nonafluorobutyl)-1,3-di-octyloxy-distannoxane (its isomers), 1,1,3,3-tetra(nonafluorobutyl)-1,3-di-nonyloxy-distannoxane (its isomers), 1,1,3,3-tetra(nonafluorobutyl)-1,3-di-decyloxy-distannoxane (its isomers), 1,1,3,3-tetra(nonafluorobutyl)-1,3-di-bezyloxy-distannoxane, and 1,1,3,3-tetra(nonafluorobutyl)-1,3-di-phenylethoxy-distannoxane. As the tetraalkyl-dialkoxy-distannoxane, only one may be selected from the above described group or two or more may be selected and used in the form of a mixture.

The dialkyltin oxides used in the present invention are those represented by the following formula (2). Although they are represented by the structural formula (2), they may be monomers, aggregates, oligomers or polymers. It is known that dialkyltin oxides do not exist in the form of a monomer, since a double bond like Sn=O cannot be normally formed, and do exist in the form of a polymer resulting from polymerization via a tin-oxygen-tin bond as shown in the following formula (15).

[Formula 13]

(2)

wherein $R^7$ and $R^8$ each independently represent an alkyl group, aralkyl group or aryl group; and e and f are integers of 0 to 2, e+f being 2.

[Formula 14]

(15)

wherein $R^{16}$ and $R^{17}$ each represent the same groups as defined above in connection with $R^7$ and $R^8$; k and l represent the same as defined above in connection with e and f; and n is an integer of 2 or more. The structure of the end group is unknown, and therefore omitted.

Examples of $R^7$ and $R^8$ in the dialkyltin oxides represented by the formula (2) include: alkyl groups as aliphatic hydrocarbon groups with 1 to 12 carbon atoms and cycloalkyl groups as aliphatic hydrocarbon groups with 5 to 12 carbon atoms, such as methyl, ethyl, propyl (its isomers), butyl (its isomers), pentyl (its isomers), hexyl (its isomers), heptyl (its isomers), octyl (its isomers), nonyl (its isomers), decyl (its isomers), undecyl (its isomers), dodecyl (its isomers), 2-butenyl, cyclobutenyl, cyclobutyl, cyclopentyl, cyclohexyl, cyclopentyl, cyclopentadienyl and cyclohexenyl groups; aralkyl groups with 7 to 20 carbon atoms, such as benzyl and phenylethyl groups; and aryl groups with 6 to 20 carbon atoms, such as phenyl, tolyl and naphthyl groups. They may contain an ether linkage or may be halogenated hydrocarbon groups in which all of or part of hydrogen atoms of each hydrocarbon group are replaced by halogen atoms, such as nonafluorobutyl and heptafluorobutyl (their isomers); however, they are not limited to these examples. Preferably, $R^7$ and $R^8$ are lower alkyl groups. More preferably, they are linear or branched alkyl groups with 1 to 8 carbon atoms. The above described kinds of groups with a larger number of carbon atoms than those described above can also be used; however, they sometimes impair the flowability or the productivity of dialkyltin alkoxides.

Examples of such dialkyltin oxides include: dialkyltin oxides, such as dimethyltin oxide, diethyltin oxide, dipropyltin oxide (its isomers), dibutyltin oxide (its isomers), dipentyltin oxide-(its isomers), dihexyltin oxide (its isomers), diheptyltin oxide (its isomers), dioctyltin oxide, and dicyclohexyltin oxide; diaralkyltin oxides, such as ditolyltin oxide and diphenylethyltin oxide; and diaryltin oxides, such as diphenyltin oxide, bis(2,6-dimethyl-phenyl)tin oxide and dinaphthyltin oxide. As the dialkyltin oxide, only one may be selected from the above described group or two or more may be selected and used in the form of a mixture.

As the starting material, either an aggregate or polymer of a tetraalkyl-dialkoxy-distannoxane represented by the formula (1) and a dialkyltin oxide represented by the formula (2) may be used.

The tetraalkyl-dialkoxy-distannoxane represented by the formula (1), which is used as the starting material, can be produced by any known process. This tetraalkyl-dialkoxy-distannoxane can also be produced by the process of the present invention using the dialkyltin oxide represented by the formula (2) as starting material and the hydroxy compound represented by the formula (3) as reactant.

The reactant used in the present invention is a hydroxy compound and preferably an alcohol represented by the following formula (3).

[Formula 15]

$$R^9 OH \qquad (3)$$

wherein $R^9$ represents a n-butyl group, 2-methylpropyl group, linear or branched alkyl group with 5 to 12 carbon atoms, cycloalkyl group with 5 to 12 carbon atoms, linear or branched alkenyl group with 2 to 12 carbon atoms, substituted or unsubstituted aryl group with 6 to 19 carbon atoms, or aralkyl group with 7 to 20 carbon atoms that includes an alkyl selected from the group consisting of linear or branched alkyl with 1 to 14 carbon atoms and cycloalkyl with 5 to 12 carbon atoms.

Concrete examples of the above described hydroxy compounds include: aliphatic alcohols with 1 to 12 carbon atoms and alicyclic alcohols with 5 to 12 carbon atoms, such as 1-butanol, 2-methyl-1-propanol, 2-methyl-2-propanol, cyclobutanol, 1-pentanol, 2-pentanol (its isomers), 3-pentanol, 3-methyl-1-butanol, 2-methyl-1-butanol, 2-methyl-2-butanol (its isomers), 2-methyl-2-butanol (its isomers), 3-methyl-2-butanol (its isomers), cyclopentanol, 2-methyl-1-cyclobutanol (its isomers), 3-methyl-1-cyclobutanol (its isomers), 1-methyl-1-cyclobutanol (its isomers), cyclobutyl-methanol (its isomers), 1-hexanol, 2-hexanol (its isomers), 3-hexanol (its isomers), 4-methyl-1-pentanol (its isomers), 3-methyl-1-pentanol (its isomers), 2-methyl-1-pentanol (its isomers), 2-ethyl-1-butanol, 3-methyl-2-pentanol (its isomers), 3-methyl-3-pentanol (its isomers), cyclohexanol, 1-methyl-1-cyclopentanol (its isomers), 2-methyl-1-cyclopentanol (its isomers), cyclobutylmethanol (its isomers), 2-cyclobutylethanol (its isomers), 1-cyclobutylethanol (its isomers), (1-methyl-cyclobutyl)-methanol (its isomers), (2-methyl-cyclobutyl)-methanol (its isomers), heptanol (its isomers), cyclohexylmethanol (its isomers), (methyl-cyclohexyl)methanol (its isomers), cyclohexylethanol (its isomers), (ethyl-cyclobutyl)-methanol (its isomers), (methyl-cyclopropyl)ethanol (its isomers), (ethyl-cyclopropyl) methanol (its isomers), octanol (its isomers), nonanol (its isomers), decanol (its isomers), undecanol (its isomers), dodecanol (its isomers), propenyl alcohol, butenyl alcohol (its isomers), pentenyl alcohol (its isomers), cyclopentanol (its isomers), cyclopentadienyl alcohol, hexenol (its isomers), and cyclohexanol (its isomers); and aralkyl alcohols such as benzyl alcohol and phenylethyl alcohol.

Of these hydroxy compounds, preferable are primary or secondary monohydric alcohols with 1 to 8 carbon atoms, such as 1-butanol, 2-butanol (its isomers), 2-methyl-1-propanol, 2-methyl-2-propanol, cyclobutanol, 1-pentanol, 2-pentanol (its isomers), 3-pentanol, 3-methyl-1-butanol, 2-methyl-1-butanol, 2-methyl-2-butanol (its isomers), 2-methyl-2-butanol (its isomers), 3-methyl-2-butanol (its isomers), cyclopentanol, 2-methyl-1-cyclobutanol (its isomers), 3-methyl-1-cyclobutanol (its isomers), 1-methyl-1-cyclobutanol (its isomers), cyclobutylmethanol (its isomers), 1-hexanol, 2-hexanol (its isomers), 3-hexanol (its isomers), 4-methyl-1-pentanol (its isomers), 3-methyl-1-pentanol (its isomers), 2-methyl-1-pentanol (its isomers), 2-ethyl-1-butanol, 3-methyl-2-pentanol (its isomers), 3-methyl-3-pentanol (its isomers), cyclohexanol, 1-methyl-1-cyclopentanol (its isomers), 2-methyl-1-cyclopentanol (its isomers), cyclobutylmethanol (its isomers), 2-cyclobutylethanol (its isomers), 1-cyclobutylethanol (its isomers), (1-methyl-cyclobutyl)-methanol (its isomers), (2-methyl-cyclobutyl)-methanol (its isomers), heptanol (its isomers), cyclohexylmethanol (its isomers), (methyl-cyclohexyl)methanol (its isomers), cyclohexylethanol (its isomers), (ethyl-cyclobutyl)-methanol (its isomers), (methyl-cyclopropyl)ethanol (its isomers), (ethyl-cyclopropyl)methanol (its isomers), octanol (its isomers) and hexenol; and primary or secondary aralkyl alcohols with 7 to 8 carbon atoms, such as benzyl alcohol.

Of the group of the above described hydroxy compounds, more preferable are primary alkyl alcohols and aralkyl alcohols with a boiling point at atmospheric pressure higher than that of water in which the carbon atom with a hydroxyl group attached to it takes the form of —$CH_2$—OH. Most preferable alcohols are 1-butanol, 2-methyl-1-propanol and alkyl alcohols with 5 to 8 carbon atoms. These hydroxy compounds may be used separately or in the form of a mixture of those selected from the above group.

In addition to these starting materials and/or reactants, other organometallic or inorganometallic compounds may be added or a solvent may also be added.

In the following, dialkyltin alkoxides produced by the process of the present invention will be described.

The dialkyltin alkoxides produced by the process of the present invention are dialkyltin alkoxides obtained by subjecting the above described starting material(s) and the reactant(s) to reaction.

The dialkyltin alkoxides produced by the process of the present invention are tetraalkyl-dialkoxy-distannoxanes having a structural formula represented by the following formula

(22) and dialkyltin dialkoxides having a structural formula represented by the following formula (16). These may be monomers, aggregates, oligomers or polymers.

[Formula 16]

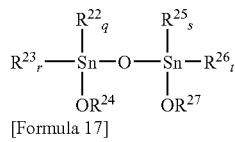
(22)

[Formula 17]

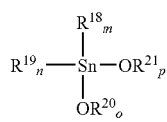
(16)

wherein $R^{22}$, $R^{23}$, $R^{25}$, $R^{26}$, $R^{18}$ and $R^{19}$ each correspond to any one of $R^1$, $R^2$, $R^4$, $R^5$, $R^7$ and $R^8$ of its starting material(s); $R^{24}$, $R^{27}$, $R^{20}$ and $R^{21}$ are selected from $R^3$, $R^6$ and $R^9$ of the corresponding starting material and reactant (provided that at least either one of $R^{24}$ and $R^{27}$ is $R^9$); q, r, s, t, m and n depend on the starting material(s) and are integers of 0 to 2, q+r being 2, s+t being 2, and m+n being 2; o and p are integers of 0 to 2, o+p being 2.

The tetraalkyl-dialkoxy-distannoxanes represented by the above formula (22) are tetraalkyl-dialkoxy-distannoxanes obtained from a starting material(s) and a reactant(s). When the reactant(s) contains compounds represented by the formula (1) and/or the formula (2), $R^{22}$, $R^{23}R^{25}$ and $R^{26}$ each correspond to any one of $R^1$, $R^2$, $R^4$, $R^5$, $R^7$ and $R^8$ shown in the formula (1) and/or the formula (2) and $R^{24}$ and $R^{27}$ each correspond to any one of $R^3$, $R^6$ and $R^9$ shown in the formula (1) and/or the formula (3) (provided that at least either one of $R^{24}$ and $R^{27}$ is $R^9$). Examples of such tetraalkyl-dialkoxy-distannoxanes are the same as those represented by the above described formula (1).

The dialkyltin dialkoxides represented by the above described formula (16) are dialkyltin dialkoxides obtained from a starting material(s) and a reactant(s).

When the reactant(s) contains compounds represented by the formula (1) and/or the formula (2), $R^{18}$ and $R^{19}$ of the dialkyltin oxides represented by the formula (16) each correspond to any one of $R^1$, $R^2$, $R^4$, $R^5$, $R^7$ and $R^8$ shown in the formula (1) and/or the formula (2) and $R^{20}$ and $R^{21}$ each correspond to any one of $R^3$, $R^6$ and $R^9$ shown in the formula (1) and/or the formula (3) (provided that at least either one of $R^{20}$ and $R^{21}$ is $R^9$).

Examples of such dialkyltin dialkoxides include: dimethyl-di(n-butoxy)-tin, dimethyl-bis(2-methylpropyloxy)-tin, dimethyl-di-pentyloxy-tin (its isomers), dimethyl-di-hexyloxy-tin (its isomers), dimethyl-di-heptyloxy-tin (its isomers), dimethyl-di-octyloxy-tin (its isomers), dimethyl-di-nonyloxy-tin (its isomers), dimethyl-di-decyloxy-tin (its isomers), butyl-methyl-di(n-butoxy)-tin, butyl-methyl-bis(2-methylpropyloxy)-tin (its isomers), butyl-methyl-di-pentyloxy-tin (its isomers), butyl-methyl-di-hexyloxy-tin (its isomers), butyl-methyl-di-heptyloxy-tin (its isomers), butyl-methyl-di-octyloxy-tin (its isomers), ethyl-butyl-di(n-butoxy)-tin, ethyl-butyl-bis(2-methylpropyloxy)-tin, ethyl-butyl-di-pentyloxy-tin (its isomers), ethyl-butyl-di-hexyloxy-tin (its isomers), ethyl-butyl-di-heptyloxy-tin (its isomers), ethyl-butyl-di-octyloxy-tin (its isomers), butyl-propyl-di(n-butoxy)-tin, butyl-propyl-bis(2-methylpropyloxy)-tin, butyl-propyl-di-pentyloxy-tin (its isomers), butyl-propyl-di-hexyloxy-tin (its isomers), butyl-propyl-di-heptyloxy-tin (its isomers), butyl-propyl-di-octyloxy-tin (its isomers), dibutyl-di(n-butoxy)-tin, dibutyl-bis(2-methylpropyloxy)-tin, dibutyl-di-pentyloxy-tin (its isomers), dibutyl-di-hexyloxy-tin (its isomers), dibutyl-di-heptyloxy-tin (its isomers), dibutyl-di-octyloxy-tin (its isomers), dibutyl-di-nonyloxy-tin (its isomers), dibutyl-di-decyloxy-tin (its isomers), dibutyl-di-benzyloxy-tin, dibutyl-di-phenylethoxy-tin, diphenyl-di(n-butoxy)-tin, diphenyl-bis(2-methylpropyloxy)-tin, diphenyl-di-pentyloxy-tin (its isomers), diphenyl-di-hexyloxy-tin (its isomers), diphenyl-di-heptyloxy-tin (its isomers), diphenyl-di-octyloxy-tin (its isomers), diphenyl-di-nonyloxy-tin (its isomers), diphenyl-di-decyloxy-tin (its isomers), diphenyl-di-benzyloxy-tin, diphenyl-di-phenylethoxy-tin, di(n-butoxy)-di-trifluorobutyl-tin, bis(2-methylpropyloxy)-di-trifluorobutyl-tin, dipentyloxy-di-trifluorobutyl-tin (its isomers), dihexyloxy-di-trifluorobutyl-tin (its isomers), diheptyloxy-di-trifluorobutyl-tin (its isomers), dioctyloxy-di-trifluorobutyl-tin (its isomers), dinonyloxy-di-trifluorobutyl-tin (its isomers), didecyloxy-di-trifluorobutyl-tin (its isomers), dibenzyloxy-di-trifluorobutyl-tin, diphenylethoxy-di-trifluorobutyl-tin, di(n-butoxy)-di-pentafluorobutyl-tin, bis(2-methylpropyloxy)-di-pentafluorobutyl-tin (its isomers), dipentyloxy-di-pentafluorobutyl-tin (its isomers), dihexyloxy-di-pentafluorobutyl-tin (its isomers), diheptyloxy-di-pentafluorobutyl-tin (its isomers), dioctyloxy-di-pentafluorobutyl-tin (its isomers), dinonyloxy-di-pentafluorobutyl-tin (its isomers), didecyloxy-di-pentafluorobutyl-tin (its isomers), dibenzyloxy-di-pentafluorobutyl-tin, diphenylethoxy-di-pentafluorobutyl-tin, di(n-butoxy)-di-heptafluorobutyl-tin, bis(2-methylpropyloxy)-di-heptafluorobutyl-tin (its isomers), dipentyloxy-di-heptafluorobutyl-tin (its isomers), dihexyloxy-di-heptafluorobutyl-tin (its isomers), diheptyloxy-di-heptafluorobutyl-tin (its isomers), dioctyloxy-di-heptafluorobutyl-tin (its isomers), dinonyloxy-di-heptafluorobutyl-tin (its isomers), didecyloxy-di-heptafluorobutyl-tin (its isomers), dibenzyloxy-di-heptafluorobutyl-tin, diphenylethoxy-di-heptafluorobutyl-tin, di(n-butoxy)-di-nonafluorobutyl-tin, bis(2-methylpropyloxy)-di-nonafluorobutyl-tin, dipentyloxy-di-nonafluorobutyl-tin (its isomers), dihexyloxy-di-nonafluorobutyl-tin (its isomers), diheptyloxy-di-nonafluorobutyl-tin (its isomers), dioctyloxy-di-nonafluorobutyl-tin (its isomers), dinonyloxy-di-nonafluorobutyl-tin (its isomers), didecyloxy-di-nonafluorobutyl-tin (its isomers), dibenzyloxy-di-nonafluorobutyl-tin and diphenylethoxy-di-nonafluorobutyl-tin.

The method of analyzing the starting materials used in the present invention and the compounds obtained by the reaction will be described.

For the analysis of the alkyltin alkoxides represented by the formulae (1), (7), (22) and (16), a method employing $^{119}$Sn-NMR can be used. This method is known as a method for analyzing alkyltin alkoxides (see, for example, U.S. Pat. No. 5,545,600). The $^{119}$Sn-NMR shift value of the dialkyltin dialkoxides represented by the formula (16), however, varies greatly depending on the concentration of the organometal compounds represented by the formula (16) or the presence of alcohol in a sample; thus, preferably the analysis is conducted using $^1$H-NMR and $^{13}$C-NMR together. The $^{119}$Sn-NMR shift value is shown, as an example, in Table 1 which corresponds to the structure of the alkyltin alkoxide of the formula (16) synthesized using 2-ethyl-1-hexanol as a reactant and dibutyltin oxide as a starting material.

TABLE 1

Concentration, in solution, of organometallic compound of formula (16) having a 2-ethyl-1-hexyloxy group vs. $^{119}$Sn-NMR shift value $^{119}$Sn-NMR data

| wt. % | δ ppm |
|---|---|
| 48.0 | −64.2 |
| 20.5 | −19.1 |
| 11.2 | −6.6 |
| 3.4 | 2.7 |

Note:
The chemical shift value (δ) is the frequency of the resonance expressed with reference to tetramethyltin (SnMe4). The concentration of the organometallic compound is the concentration by weight (wt %) in deuterated chloroform (CDCl$_3$).

In the following, the steps included in the production process of the present invention will be described in detail.

The present invention is a process for production of alkyltin alkoxides, including subjecting a starting material, which is selected from the group consisting of tetraalkyl-dialkoxy-distannoxanes represented by the chemical formula (1), dialkyltin oxides represented by the chemical formula (2), and the mixture, aggregates or polymers thereof, and a reactant represented by the chemical formula (3), a hydroxy compound, to dehydration reaction to produce an alkyltin alkoxide represented by the chemical formula (22) and/or the chemical formula (16) which corresponds to the starting material and the reactant, characterized in that the starting material and the reactant are continuously supplied to a reactor; the low boiling point components including water are taken out from the reactor; and the reaction solution, as the component in the bottom of the reactor, which contains the alkyltin alkoxide represented by the chemical formula (22) and/or the chemical formula (16) is continuously taken out from the reactor.

The starting material and the reactant may be supplied to a reactor separately, or they may be mixed with each other before being supplied to a reactor. When the starting material is a solid material, it may be brought to the liquid state by heating or brought to the liquid or slurry state by using a reactant and/or a solvent before being supplied to a reactor. The starting material and the reactant may be continuously or intermittently supplied to a reactor.

The present inventors have presumed that the reaction of a starting material with a reactant by the process of the present invention is based on the equilibrium reactions represented by the following equations (17) and (18).

[Formula 18]

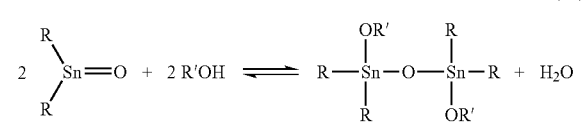

(17)

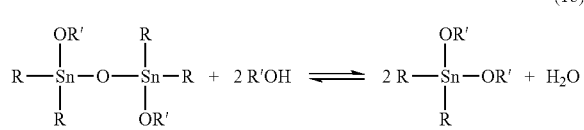

(18)

According to the present invention, a starting material and a reactant undergo dehydration reaction in a reactor in accordance with the above formula (17) and/or formula (18) and the low boiling point components containing water are removed from the reactor, whereby a tetraalkyl-dialkoxy-distannoxane and/or a dialkyltin dialkoxide can be continuously obtained from the bottom of the reactor.

When using a tetraalkyl-dialkoxy-distannoxane as a starting material and a hydroxy compound different from one corresponding to the alkoxy group of the above distannoxane as a reactant, a product is sometimes formed by the alkoxy exchange reaction presumably in accordance with the following reaction formula (19).

[Formula 19]

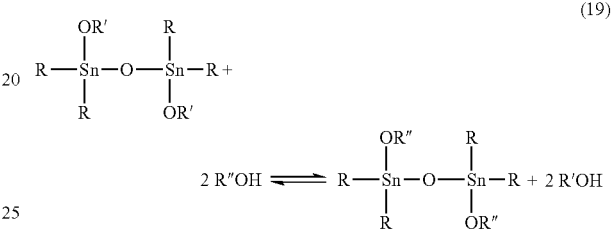

(19)

In the present invention, the type of the reactor used for dehydration reaction is not limited to any specific one. Any known tank reactor or column reactor can be used as long as the resultant low boiling point components containing water can be removed from the reactor by distillation, while the resultant high boiling point reaction mixture, containing the produced alkyltin alkoxide or alkyltin alkoxide mixture, can be taken out in the liquid state from the lower portion of the reactor. Known processes are used in which a reactor of a type that includes a stirring tank, multistage stirring tank, distillation column, multistage distillation column, multitubular reactor, continuous multistage distillation column, packed column, thin film evaporator, reactor with a support in its inside, forced circulation reactor, falling film evaporator, falling drop evaporator, trickle bed reactor or bubble column or in which a combination of the above described types of reactors can be used. From the viewpoint of allowing the dehydration equilibrium to efficiently shift to products, it is preferable to use a column reactor. And preferably the column reactor has a large gas-liquid contact area which allows the formed water to rapidly move to the gas phase. Particularly preferable is a continuous process that uses a multitubular reactor, a multistage distillation column and a packed column.

As the multistage distillation column, any multistage distillation column may be used as long as its number of theoretical plates is two or more and it enables continuous distillation. Any type of multistage distillation column can be used as long as it is normally used as a multistage distillation column, for example, tray column type ones which employ plates such as bubble cap trays, perforated trays, valve trays or counterflow trays, or packed column type ones in which various types of packings such as Raschig ring, Lessing ring, Pall ring, Berl saddle, Interlock saddle, Dickson packing, McMahon packing, Helipack, Sulzer packing or Mellapack are packed. Any packed column can be used as long as it is packed with the above described known filler. Packings having a dehydration performance may also be used.

For example, packings such as Molecular Sieves are preferably used. A plate column—packed column mixed type of column reactors which include both trays and packings are also preferably used. Preferably, such column reactors are provided with: lines for supplying the above described starting material and the above described reactant, respectively, or a line for supplying the mixed solution of the above described starting material and reactant; a line for drawing out the low boiling point reaction mixture containing water from the reactor; and a line for taking out the high boiling point reaction mixture from the reactor. Particularly preferably, the above described column reactors are such that the line for drawing out the low boiling point components containing water from the reactor is provided in such a position that enables the gas-phase components in the reactor to be drawn out from the reactor, while the line for taking out the resultant high boiling point reaction mixture from the reactor is provided in the lower portion of the reactor. In the continuous process, a starting material and a reactant are continuously or intermittently supplied to a reactor, where both the starting material and the reactant are subjected dehydration reaction in the liquid phase or the gas-liquid phase, and the resultant high boiling point reaction mixture, including the produced alkyltin alkoxide, is taken out in the liquid state from the lower portion of the reactor, while the resultant low boiling point components containing water is continuously drawn out in the gas state from the reactor. Thus, alkyltin alkoxides are produced.

The above described column reactors may also be provided separately with a line for supplying an inert gas and/or a gaseous and/or liquid reactant to the reactors from their lower portion or a line for letting part of or all of the produced high boiling point reaction mixture to circulate in the reactors again. The low boiling point components containing water which has been taken out from the reactors, may be purified by known means, such as a distillation column, to recycle the azeotrope and/or the accompanying reactant. In some cases, the raw materials used take the form of a slurry or a solid at ordinary temperature (20° C.) or they have a high viscosity; therefore, the lines are designed taking into consideration occurrence of clogging or the like or they may be provided with insulation, cooling or heating equipment.

When producing alkyltin alkoxides by the process of the present invention, only one reactor, which satisfies the requirements of the present invention, or two or more such reactors in combination may be used. It is also possible to use a reactor, which satisfies the requirements of the present invention, and other reactors in combination to produce alkyltin alkoxides. For example, processes are also part of the embodiments of the present invention in which first batch reaction is employed to allow a dialkyltin oxide and an alcohol to react with each other to produce only some alkyltin alkoxides and then a reactor, which satisfies the requirements of the present invention, is used to cause reaction in the reaction solution.

Concrete examples of reactors applicable to the present invention will be described with reference to the accompanying drawings; however, it is to be understood that reactors applicable to the present invention are not limited to these examples. Instrument systems such as flow instrument and thermometer and known process systems such as reboiler, pump, condenser and distillation column can also be added to the reactors, depending on the situation. Heating can be performed by known means, such as steam and heater, and cooling can also be performed by known means such as natural cooling, cooling water and brine.

FIG. 2 is a cross section of a column reactor seen from the front. The column reactor may be of a type that includes a packed column with a packing packed therein or a multistage distillation column, or of any other type. Here the column reactor will be described in terms of a column reactor including a packed column. A mixed solution of a starting material and a reactant is introduced from a supplying line 4 into a reactor 1, or a starting material is introduced from the supplying line 4 and a reactant from a supplying line 8 into the reactor 1. An inert gas is introduced from a gas supplying line 7 into the reactor 1. The introduced starting material and reactant are dispersed in the inside of the reactor. The above described mixed solution flows downward along a packing packed in the reactor while vaporizing water. The inside of the reactor is controlled to be under reduced pressure, atmospheric pressure or pressure, and the inert gas supplied from the gas supplying line 7 depending on the situation and/or low boiling point components including the gas of the reactant and water formed by the reaction is drawn out from the upper portion 2 of the reactor and discharged from a vent line 5. The reaction solution in which the concentration of alkyltin alkoxide, as a product, has been increased in the inside of the reactor is taken out from the lower portion 3 of the reactor and discharged form the take-out line 6. The packed column and the lines are heated or cooled, depending on the situation, by known means such as jacket or heater.

FIG. 3 is a cross section of a combined tank and column reactor seen from the front. The tank reactor may include a stirring tank, a circulation tank or any other tank. Here the tank reactor will be described in terms of a tank reactor including a stirring tank. The column reactor may be a packed column with a packing packed thereinto, a multistage distillation column, or any other column reactor. Here, the column reactor will be described in terms of a packed column with a packing packed thereinto. A reactant is introduced from a supplying line 15 to a stirring tank 9, while a starting material is introduced from a supplying line 16 to the stirring tank 9. The introduced starting material and reactant are dispersed in the stirring tank. The above described mixed solution is heated while vaporizing water. The inside of the stirring tank is controlled to be under reduced pressure, atmospheric pressure or pressure, and the inert gas supplied from the gas supplying line 18 depending on the situation and/or low boiling point components including the gas of the reactant and water formed by the reaction is drawn out from the upper portion 11 of the stirring tank and discharged from a vent line 17.

The reaction solution in which the concentration of alkyltin alkoxide, as a product, has been increased in the inside of the stirring tank is transferred the lower portion 12 of the stirring tank to a buffer tank 24 through a transfer line 19 and then from the buffer tank to a column reactor through a junction line 25. The solution having been introduced into the reactor 10 from the junction line 25, which contains a dialkyltin alkoxide, is dispersed by the packing in the inside of the reactor. The above described solution flows downward along a packing packed in the reactor while vaporizing water. The inside of the reactor is controlled to be under reduced pressure, atmospheric pressure or pressure, and the inert gas supplied from the gas supplying line 20 depending on the situation and/or low boiling point components including the gas of the reactant and water formed by the reaction is drawn out from the upper portion 13 of the reactor and discharged from a vent line 21. The reaction solution in which the concentration of dialkyltin alkoxide, as a product, has been increased in the inside of the reactor is taken out from the lower portion 14 of the reactor and discharged from the take-out line 23. The reactant may be replenished from a supplying line 22 depending on the situation. The stirring tank, the packed column and the lines are heated or cooled, depending on the situation, by known method such as jacket or heater.

For the reactors or lines, any materials can be used as long as they do not have a detrimental effect on the starting material or reactant used. SUS 304, SUS 316 or SUS 316L are inexpensive and preferably used.

The time spent in the dehydration reaction performed in the present invention (in the case of continuous process, the residence time of an alkyltin alkoxide) is not particularly limited, and usually it is 0.001 to 50 hours, preferably 0.01 to 10 hours and more preferably 0.1 to 2 hours.

The reaction temperature varies depending on the kind of the raw material compounds used, but usually it is in the range of 50 to 350° C. and preferably in the range of 60 to 160° C. To keep the reaction temperature constant, the above described reactors may be provided with known cooling equipment or heating equipment. The pressure under which the reaction is performed varies depending on the kind of the raw material compounds used or the reaction temperature, but the reaction may be performed under reduced pressure, atmospheric pressure or pressure. Usually it is in the range of 0.1 to $2.0 \times 10^7$ Pa. In the present invention, a reaction solvent is not necessarily used; however, to make the reaction operations easier, an appropriate inert solvent such as ethers, aliphatic hydrocarbons or aromatic hydrocarbons can be used as reaction solvents.

The reaction time and the reaction temperature will be described in more detail.

The present invention is characterized by continuously supplying a starting material, which is selected from the group consisting of a dialkyltin oxide, a tetraalkyl-dialkoxy-distannoxane and the mixture thereof, and a hydroxy compound as a reactant, to a reactor and taking out the low boiling point components from the reactor to continuously obtain a reaction solution, as a component in the bottom of the reactor, which contains an alkyltin alkoxide corresponding to the starting material and the reactant. According to the present invention, alkyltin alkoxides, as intended products, can be produced at very high production efficiency, unlike conventional processes. Further surprisingly, the present invention enables the dehydration reaction, which is an equilibrium reaction, to be promoted, and besides it enables the production of trialkyltin compounds, due to the pyrolytic reaction of alkyltin alkoxides, to be significantly decreased.

If the dehydration reaction is performed by the process of the present invention under the conditions described below, the amount of the tributyltin compound produced as a by-product during the dehydration reaction can be kept 1% by mole or less per 100% of tin atoms contained in the starting material. It goes without saying that when the starting material contains a tributyltin compound, the amount can sometimes be outside the above described range; therefore, such a tributyltin compound needs to be removed in advance or the amount of the tributyltin compound contained in the starting material needs to be adjusted so that it falls within the allowable range. Further, since the production of a tributyltin compound is promoted not only during the dehydration reaction, but by the pyrolytic reaction of an alkyltin alkoxide, when intending to inhibit the by-production of a tributyltin compound, it is preferable to decrease the residence time of an alkyltin alkoxide in pipes and decrease the temperature of the same. Equipment other than a dehydration reactor may be used to control the amount of the tributyltin compound produced.

When producing an alkyltin alkoxide from a tetraalkyl-dialkoxy-distannoxane represented by the chemical formula (1) and/or a dialkyltin oxide represented by the chemical formula (2), as a starting material, and an alcohol represented by the chemical formula (3), as a reactant, an alkyltin alkoxide represented by the chemical formula (22) and/or the chemical formula (16), which contains only a very small amount of tributyl compound, can be obtained by performing dehydration reaction at a dehydration rate defined by the following equation (4). A mixed solution of a dialkyltin oxide represented by the chemical formula (2) an alcohol represented by the chemical formula (3) may also be used; however, from the viewpoint of solubility or conveyance of the mixed solution, it is preferable to use a tetraalkyl-dialkoxy-distannoxane represented by the chemical formula (1) and an alcohol represented by the chemical formula (3).

[Expression 4]

$$\text{Dehydration rate} > \frac{60X + 10Y}{A^{-1} \cdot \exp\left(\frac{B}{R \cdot T}\right)} \quad (4)$$

wherein the dehydration rate means the amount of the water that is formed by the dehydration reaction and drawn out of the system per unit time $[\text{mol} \cdot \text{hr}^{-1}]$; X represents the total mole number [mol] of tin atoms contained in the alkyltin compound represented by the general formula (2) which is contained in the starting material; Y represents the total mole number [mol] of tin atoms contained in the alkyltin compound represented by the general formula (1) which is contained in the starting material; T represents a temperature [K] at which the dehydration reaction is performed; R represents a gas constant=8.314 $\text{J} \cdot \text{mol}^{-1} \cdot \text{K}^{-1}$; and A and B are coefficients depending on the kind of alkyltin compound, wherein the coefficients A and B in the above described equation (4) depend on the kind of alkyltin compound as the starting material and are obtained based on the set primary standard substance. When the starting material contains alkyltin compounds represented by the chemical formula (1), the above described coefficients A and B represent the frequency factor and the activation energy of the pyrolytic reaction of primary standard substance, which is an alkyltin compound arbitrarily selected from the alkyltin compounds represented by the chemical formula (1) and contained in the starting material, and are obtained from the following equation (5). When the starting material does not contain alkyltin compounds represented by the chemical formula (1), but contains alkyltin compounds represented by the chemical formula (2), the above described coefficients A and B represent the frequency factor and the activation energy of the pyrolytic reaction of primary standard substances, which is an alkyltin alkoxide arbitrarily selected from the alkyltin alkoxides represented by the following chemical formula (7) formed from the alkyltin compounds represented by the chemical formula (2) contained in the starting material and the reactant, and are obtained from the following equation (5).

[Expression 5]

$$k = A \cdot \exp\left(-\frac{B}{R \cdot T}\right) \quad (5)$$

wherein k represents a first-order rate constant $[\text{hr}^{-1}]$; A represents a frequency factor $[\text{hr}^{-1}]$; B represents an activation energy $[\text{J} \cdot \text{mol}^{-1}]$; R represents a gas constant=8.314 $\text{J} \cdot \text{mol}^{-1} \cdot \text{K}^{-1}$; and T represents a temperature [K] at which the pyrolytic reaction is performed. The above described k represents a first-order rate constant of the pyrolytic reaction which is obtained by the following equation (6):

[Expression 6]

$$k \cdot t = -\ln(1-X) \quad (6)$$

wherein k represents a first-order rate constant [hr$^{-1}$]; t represents a heating time; and X [hr] represents a reduction ratio [mol/mol] with respect to the initial concentration of a primary standard substance,

[Formula 20]

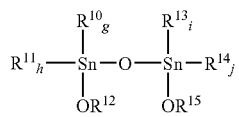

(7)

wherein $R^{10}$, $R^{11}$, $R^{13}$ and $R^{14}$ correspond to either $R^7$ or $R^8$ of the starting material; g, h, i and j correspond to either e or f of the starting material; at least one of $R^{12}$ and $R^{15}$ corresponds to $R^9$ of the reactant.

If the reaction is performed at a dehydration rate higher than that provided by the above described equation (4), an alkyltin alkoxide that includes a smaller amount of trialkyltin compound can be obtained. However, to obtain a much larger amount of alkyltin alkoxide represented by the chemical formula (16), it is preferable to perform the reaction at a dehydration rate higher than that provided by the following equation (20):

[Expression 7]

$$\text{Dehydration rate} > \frac{75X + 25Y}{A^{-1} \cdot \exp\left(\frac{B}{R \cdot T}\right)} \quad (20)$$

wherein X, Y, A, B, R and T each represent the same things as described in connection with the equation (4), A and B being obtained from the equations (5) and (6), like those of the equation (4).

The above described pyrolytic reaction is a reaction which includes the reaction shown by the following formula (21) as a representative and whereby the amount of tetraalkyl-dialkoxy-distannoxanes represented by the chemical formula (1) and/or the chemical formula (7) is decreased. Specifically, the change with time in the decreased amount of tetraalkyl-dialkoxy-distannoxanes, represented by the chemical formula (1) and/or the chemical formula (7), is measured by $^{119}$Sn-NMR spectroscopy while stirring the solution containing tetraalkyl-dialkoxy-distannoxanes represented by the chemical formula (1) and/or the chemical formula (7) in a nitrogen atmosphere and keeping the temperature of the solution constant, and the reaction rate is analyzed by the above described equations (6) and (5). In the following equation (21), tetraalkyl-dialkoxy-distannoxanes are described as monomers; however, it goes without saying that they may be dimers, aggregates, oligomers or polymers.

[Formula 21]

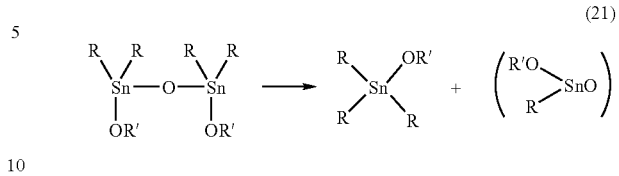

(21)

The heating temperature in the above described pyrolytic reaction is any temperature in the range of 100° C. to 200° C. (e.g. 120° C., 140° C. and 160° C.). In the above described pyrolytic reaction system, the content of the compounds represented by the chemical formula (1) and/or the chemical formula (7) is 95% or more. The above described pyrolytic reaction is performed, while applying heating, under the conditions that prevent the reaction from being affected by substances (e.g. oxygen or water) capable of promoting the decomposition of the compounds represented by the chemical formula (1) and/or the chemical formula (7). The amount of the compounds, which are represented by the chemical formula (1) and/or the chemical formula (7), decreased by heating due to the reaction represented by the above described formula (21) is measured with time by $^{119}$Sn-NMR spectroscopy. The products of the pyrolytic reaction cannot be defined clearly, but it can be said that they include a trialkyltin alkoxide.

The alkyltin alkoxides produced in accordance with the present invention and at a dehydration rate provided by the equation (4) or higher have a significantly low content of trialkyltin compounds and chlorine-containing compounds, because the production process does not use chlorine-containing compounds as the raw materials. Starting materials can sometimes include a chlorine-containing compound; however, according to the present invention, the amount of such chlorine-containing compound is not increased to above the amount of the starting material, in principle, by the reaction, and thus, alkyltin alkoxides of high purity can be obtained.

If the amount of the reactant used is in excess of that of the starting material, the chemical equilibrium advantageously shifts to products; however, when intending to increase the concentration of alkyltin alkoxide in the alkyltin alkoxide-containing solution taken out from the reactor, an excess of hydroxy compound remaining unreacted must be removed by distillation. Thus the energy efficiency is low. In contrast, if the amount of the reactant used is too low, a larger amount of starting material remaining unreacted must be recovered. Accordingly, the ratio of the starting material to the reactant is in the range of 3 to 200, in terms of the ratio of the total mole number of tin atoms contained in the starting material to the mole number of the reactant. And to increase the concentration of the dialkyltin alkoxide taken out from the bottom of the reactor, the ratio is preferably in the range of 3 to 100 and more preferably in the range of 3 to 10.

The present invention is characterized in that the water and alkyltin alkoxide produced by the reaction are rapidly taken out from the system. As aforementioned, the present inventors have presumed that in conventional batch processes, the formed water rapidly undergoes reverse reaction with the produced alkyltin alkoxide, whereby the productivity is impaired. The present invention provides a process which ensures increased productivity by allowing the free water formed in the reaction solution to rapidly shift to the gas phase and removing the same from the reactor while taking the formed alkyltin alkoxide out of the system. The inventors have presumed that the free water formed in the above described reaction shifts from the reaction solution to the gas phase due to the gas-liquid equilibrium in the system.

The production process of the present invention aims at inhibiting the reverse reaction, in which the equilibrium reactions represented by the formulae (13) and/or (14) shifts to the left (products), by increasing the specific surface area of the reaction solution to accelerate the shift of the formed water, which depends on the gas-liquid equilibrium, while taking out the produced alkyltin alkoxide from the system. Accordingly, in the above described tank- and/or column-reactor, to allow the formed water to rapidly shift to the gas phase, preferably the volume of the liquid components is kept ⅔ or less of the opening capacity of the reactor and more preferably ⅓ or less of the same.

The term "in the system" herein used means the inside of reactors, of piping or equipment on the periphery of reactors, or of equipment or piping of recovery systems. The term "high boiling point reaction mixture" means: a high boiling point substance-containing solution supplied to reactors; a high boiling point substance-containing reaction solution in reactors; a high boiling point substance-containing reaction solution discharged from reactors; or a concentrated solution containing an increased concentration of high boiling point substance by evaporating a part of the reactant. Some high boiling point reaction mixtures have high boiling point substances dissolved therein or some high boiling point reaction mixtures are in the form of a slurry of high boiling point substances. When a high boiling point reaction mixture is in the form of a slurry, the indissoluble part of the slurry is also included in the "high boiling point reaction mixture".

The term "high boiling point substances" herein used means organic substances having a boiling point as high as or higher than that of alkyltin alkoxides. For example, high-molecular-weight by-products produced by the reaction are also included in the high boiling point substances.

The term "low boiling point components, containing water" herein used means the water formed by the reaction and part of reactants, as organic substances having a boiling point lower than that of alkyltin alkoxides produced in the present invention. For example, low-molecular-weight by-products produced by the reaction are also included in the low boiling point substances. When inert gases or organic solvents are used, part of such organic solvents is also included in the low boiling point substances.

When producing an alkyltin alkoxide by allowing a starting material and a reactant to react with each other in accordance with the process of the present invention, the reaction rate is increased by removing from the reaction system the water formed with the progress of the reaction. In this process, the reaction is allowed to progress by supplying an inert gas to the system to efficiently decrease the partial pressure of the produced low boiling point components including water. Accordingly, preferably means is employed in which an inert gas that does not have an adverse effect on the reaction, such as nitrogen, argon, helium, carbon dioxide or lower hydrocarbon gas, is introduced into the system to allow such a gas to entrain the produced low boiling point components including water so that they are removed from the system, or in which the inside of the system is kept at a suitable pressure for removing the water formed in the system so that the formed water or the azeotropic components including water have a vapor pressure at the reaction temperature, in other words, the formed water or the azeotropic components including water can shift from the liquid phase to the gas phase.

Of the above described inert gases, carbon dioxide can sometimes react with the produced alkyltin alkoxide to form a carbon oxide-inserted alkyltin alkoxide or further form a small amount of carbonate ester from the carbon oxide-inserted alkyltin alkoxide. However, since it does not have a serious adverse effect on the reaction, it is also included on the inert gases. As shown in the reaction formulae (13) and/or (14), the chemical equilibrium is allowed to shift advantageously to products by increasing the concentration of the hydroxy compound as a reactant.

Specifically, in the inside of the above described reactor, the hydroxy compound as a reactant is consumed as an alkoxy group for an alkyltin alkoxide as the reaction progresses, and the concentration of the hydroxy compound are gradually decreased. Thus, the effect of removing the produced low boiling point components including water can sometimes be produced by supplying the reactant or the reactant in the gas state even from the lower part of the reactor to increase the concentration of the hydroxy compound as a reactant or by supplying the hydroxy compound in the gas state from the lower part of the reactor so that the gas entrains the low boiling point components including water to the outside of the system, like the cases in which inert gases are used.

It goes without saying that the hydroxy compound or the hydroxy compound in the gas state, an organic compound in the inert gas state, and/or the organic solvent that forms an azeotropic mixture with water or the organic solvent in the gas state may be supplied together with an inert gas from the lower part of the reactor. As the circulating inert gas or reactant gas, a gas containing the smallest possible amount of oxygen is preferably used. In this case, such a gas may be circulated through molecular sieves or a layer packed with ion exchange resin or deoxidizer, and the gas having been cooled to an extreme low temperature and in the dehydrated state can also be used. The water content in the circulating gas, in terms of dew point, is preferably −10° C. or less and more preferably −40° C. or less. When supplying an inert gas from the lower part of the reactor, the amount of the inert gas supplied is not particularly limited. It varies depending on the kind, structure or size of the reactor. When using a distillation column as a reactor, it is appropriately controlled so that violent flooding should not occur.

The alkyltin alkoxides produced by the process of the present invention can be used as they are, or they can be used in the diluted or concentrated form, or they can be used with other components added thereto.

Alkyltin alkoxides are known as catalysts used in the production of carbonate esters such as diallylcarbonate esters, alkylarylcarbonate esters and diarylcarbonate esters; isocyanates; and polycarbonates. The alkyltin alkoxides produced by the process of the present invention are of high purity and low cost, and thus making it possible to industrially produce carbonate esters such as diallylcarbonate esters, alkylarylcarbonate esters and diarylcarbonate esters; isocyanates; and polycarbonates more advantageously.

Specifically, the alkyltin alkoxides produced by the process of the present invention are characterized in that they include only a very small amount of tributyltin compounds and chlorine compounds. Such dialkyltin alkoxides are very useful as catalysts for production of carbonate esters such as diallylcarbonate esters, alkylarylcarbonate esters and diarylcarbonate esters; isocyanates; and polycarbonates, for synthesis of esters, for transesterification and for curing of silicon polymer or urethane.

Many restrictions are imposed on some of trialkyltin compounds because of their toxicity. And it is known that presence of chlorine-containing compounds causes corrosion of metal or deterioration of polymers. When traditional alkyltin alkoxides were used for the above described catalyst applications, the products obtained using such catalysts used to be contaminated with the above described harmful trialkyltin compounds or chlorine compounds. However, it has been unknown in which step the products have been contaminated with such compounds or from which compounds such contamination has arisen.

After directing tremendous research effort toward the solution of such problems, the present inventors have found that most of trialkyltin compounds or chlorine-containing compounds which contaminate the products are contained in the dialkyltin alkoxides used from the beginning. The alkyltin alkoxides produced by the process of the present invention are of high purity, and therefore containing only a very small amount of trialkylin compounds or chlorine-containing compounds, whereby the problems resulting from traditional alkyltin alkoxides can be solved.

For example, as processes for production of carbonate esters, there are known a phosgene process using phosgene and an oxidative carbonylation process using carbon monoxide. And it is known that these processes use chlorine-containing compounds as raw materials or catalysts, and the carbonate esters having been produced by the processes contain chlorine-containing compounds, causing serious adverse effects on the production of polycarbonates, which uses carbonate esters as raw materials (e.g. deactivation of polymerization catalysts, coloring or deterioration of polycarbonates). Further, when using such carbonate esters as additives for petrol or diesel fuel, they may cause corrosion of engines or piping.

The present inventors have already disclosed in WO 03/055840 and WO 04/014840 a process for production of carbonate esters and water alone from carbon dioxide and alcohols by using a dialkyltin alkoxide (in these patents, the term "dialkyltin alkoxide" is used in a wider sense to include dialkyltin alkoxide and tetraalkyltin-dialkoxy-distannoxane). These prior inventions are further improved by the present invention. And use of the process of the present invention makes it possible to effectively produce dialkyltin alkoxides at a very high speed and with a high purity, and hence carbonate esters containing a very small amount of tributyltin compound or chlorine compound. The resultant carbonate esters can be easily converted into diaryl carbonate esters with very small chlorine content by transesterification or disproportionation.

As a process for production of carbonate esters using an alkyltin alkoxide produced by the process of the present invention, those disclosed in WO 03/055840 and WO 04/014840, which are described above, are preferably used. A reaction solution including a dialkylcarbonate ester can be obtained by allowing a mixture containing an alkyltin alkoxide and carbon dioxide to react at a temperature ranging form 60° C. to 200° C., for 0.1 to 10 hours, under pressure ranging form 0.1 Mpa to 20 MPa. The reaction solution including a dialkylcarbonate ester is treated by a known process such as distillation process so that it is separated into components including dialkylcarbonate ester and tin-containing residue. The tin-containing residue includes: compounds represented by the chemical formula (1) or the chemical formula (2), which are used as reactants in the process of the present invention; and a component containing tin whose structure cannot be clarified by the current analytical method. Surprisingly, use of the process of the present invention also makes it possible to produce alkyltin alkoxides, which are the products the present invention aims at, from the tin-containing component whose structure has not been clarified yet.

Alkylarylcarbonate esters and diaryl carbonate esters can be obtained by allowing the above described dialkylcarbonate ester and an aromatic hydroxy compound to react by a known process.

As processes for production of diaryl carbonate esters, processes such as phosgene process, which uses phosgene, and oxidative carbonylation process, which uses carbon monoxide, are known. However, these processes use a chlorine-containing compound as their raw materials or catalysts, and it is known that the produced diarylcarbonate esters contain a chlorine compound and use of such diarylcarbonate esters has a serious effect on the production of polycarbonates using carbonate esters as raw materials (e.g. deactivation of polymerization catalysts, coloring or deterioration of polycarbonates). Further, when using such carbonate esters as additives for petrol or diesel fuel, they may cause corrosion of engines or piping. The present inventors have already disclosed in WO 03/055840 and WO 04/014840 a process for production of carbonate esters and water alone from carbon dioxide and alcohols by using a dialkyltin alkoxide. These prior inventions are further improved by the present invention. And use of the process of the present invention makes it possible to produce diaryl carbonate esters of high purity and with very small chlorine-compound content conveniently and efficiently.

Further, use of the diaryl carbonate esters obtained by the process of the present invention makes it possible to produce polycarbonates, isocyanates or polycarbonate diols. In this case, diphenyl carbonate is preferably used as a diaryl carbonate ester.

In the following, polycarbonates, isocyanates and polycarbonate diols obtained as above will be described.

First, polycarbonates will be described. Diaryl carbonate esters are known as materials for polycarbonates produced by melt process. However, conventional diaryl carbonate esters, which are produced using chlorine-containing compounds as raw materials, have a large amount of chlorine compound remaining therein, and when they are subjected to transesterification with bisphenol A, such chlorine compounds contribute to deactivation of catalysts. When using a large amount of catalyst as a possible approach for coping with this deactivation, the weathering resistance, hue, or physical properties of the resultant polycarbonates can sometimes be adversely affected. In such a case, a step is needed of removing the chlorine compound from the diaryl carbonate.

Methods for coping with the problem are known, for example, in which chlorine compounds are removed by subjecting chlorine compound-containing diaryl carbonate esters to alkali cleaning or distillation purification. However, these methods still have serious problems. Alkali cleaning may cause the disappearance of dehydration of diaryl carbonate esters, since the melting point of diaryl carbonate esters is relatively high and they are subjected to alkali cleaning in the molten state. Distillation purification has a serious problem of high cost. Since the chlorine compounds include various kinds of chlorine-containing compounds, from low boiling point components and high boiling point components, the purification cost, when using such diaryl carbonate esters for industrial application, is serious.

In the process for production of diphenyl carbonate from ethylene carbonate, which is produced using carbon dioxide as a raw material, first dimethyl carbonate is obtained from ethylene carbonate, then methyl phenyl carbonate is obtained, and finally diphenyl carbonate is obtained. In this process, dimethyl carbonate is an indispensable intermediate to produce diphenyl carbonate, due to the restriction by boiling point (in the system, the boiling point of methanol is the lowest, and to allow the equilibrium to shift, it is necessary to form an azeotrope having a minimum boiling point with methanol). Methyl phenyl carbonate, which is an inevitably derived intermediate, is likely to cause secondary reaction such as decarboxylation, and diphenyl carbonate, as a final product, is contaminated with a slight amount of a by-product such as anisole, which includes a methyl group, even after the purifying step. This contamination can sometimes decrease the polymerization rate during the production process of polycarbonates using diphenyl carbonate, cause variation in polymerization degree, or affect the hue of the product.

In contrast, the process of the present invention forms no by-products. It is difficult to specify the above described by-products having a methyl group, which are derived form the dimethyl carbonate. However, in the process for production of diaryl carbonate esters of the present invention, the intermediate is not dimethyl carbonate, but dialkyl carbonate esters having a long-chain alkyl group, which are derived from alcohol represented by the chemical formula (3); thus, diphenyl carbonate can be obtained which does not contain by-products having a methyl group, which have an adverse effect on the production of polycarbonates.

Examples of diaryl carbonate esters preferably used as the raw materials for polycarbonates are diaryl carbonate esters that contain the above described organic compounds having a methyl group (by-products) at 100 ppm or less and more preferably at 10 ppm or less.

In the following isocyanates will be described. Isocyanates can be produced by: first allowing a diaryl carbonate ester (particularly diphenyl carbonate) produced using an alkyltin alkoxide of the present invention and a polyamine compound to react with each other to obtain a polyaryl carbamate, such as hexamethylene diaryl carbamate; and then subjecting the polyaryl carbamate to pyrolytic reaction. Conventionally, no economical process for synthesis of isocyanates has been known but one which uses phosgene as a raw material. However, diaryl carbonate esters produced by the process of the present invention are very low-cost and contain a very small amount of chlorine compounds, thereby enabling advantageous production of isocyanates. Conventional isocyanates produced from chlorine-containing compounds such as phosgenes contain chlorine compounds. The primary use of isocyanates are the production of urethane, and catalysts used for urethane production are susceptible to deactivation or denaturation by chlorine. The isocyanates produced by the process of the present invention, however, do not substantially contain chlorine, and therefore not causing the above described problem.

In the following polycarbonate diols will be described. Polycarbonate diols of high purity can be produced using diaryl carbonate esters which are produced using the alkyltin alkoxides of the present invention.

Polycarbonates, isocyanates and polycarbonate diols produced using diaryl carbonate esters which are produced by the process of the present invention are industrially very valuable, because they are of high purity compared with those produced by conventional processes, they can be produced conveniently (accordingly at low cost), and they form no by-product.

Isocyanates can be produced using the above described dialkyl carbonate esters and/or the above described diaryl carbonate esters by any know process.

Diaryl carbonate esters are known as materials for polycarbonates produced by melt process. However, conventional diaryl carbonate esters, which are produced using chlorine-containing compounds as raw materials, have a large amount of chlorine compound remaining therein, and when they are subjected to transesterification with bisphenol A, such chlorine compounds contribute to deactivation of catalysts. When using a large amount of catalyst as a possible approach for coping with this deactivation, the weathering resistance, hue, or physical properties of the resultant polycarbonates can sometimes be adversely affected. In such a case, a step is needed of removing the chlorine compound from the diaryl carbonate. Methods for coping with the problem are known, for example, in which chlorine compounds are removed by subjecting chlorine compound-containing diaryl carbonate esters to alkali cleaning or distillation purification.

However, these methods still have serious problems. Alkali cleaning may cause the disappearance of dehydration of diaryl carbonate esters, since the melting point of diaryl carbonate esters is relatively high and they are subjected to alkali cleaning in the molten state. Distillation purification has a serious problem of high cost. Since the chlorine compounds include various kinds of chlorine-containing compounds, from low boiling point components and high boiling point components, the purification cost, when using such diaryl carbonate esters for industrial application, is serious. Diaryl carbonate esters produced using dialkyltin alkoxides produced by the process of the present invention are low-cost and contain a very small amount of chlorine compounds, thereby enabling advantageous production of isocyanates.

Thus, the production process which uses the alkyltin alkoxides produced by the present invention enables carbonate esters, isocyanates and polycarbonates to be industrially produced at low cost and with high purity, compared with those produced by conventional processes.

EXAMPLES

The present invention will now be described in more detail with reference to the following Examples, which should not be construed as limiting the scope of the present invention.

Analysis Methods

1) NMR Analysis

Apparatus: JNM-A400 FT-NMR system (manufactured by JEOL Ltd., Japan)

(1) Preparation of $^1$H-NMR, $^{13}$C-NMR and $^{119}$Sn-NMR Analysis Samples

About 0.3 g of a tin compound was weighed out, and then charged with about 0.7 g of deuterated chloroform (manufactured by Aldrich Chemical Co., 99.8%) and, as a $^{119}$Sn-NMR internal reference, about 0.5 g of tetramethyltin (manufactured by Wako Pure Chemical Industries Ltd., Wako first grade). The resulting solution was uniformly mixed for use as an NMR analysis sample.

2) Water Analysis

Apparatus: CA-05 Trace Moisture Meter, manufactured by Mitsubishi Chemicals Corporation, Japan.

(1) Quantitative Analysis

A syringe was used for collecting 0.12 ml of the analysis sample and weighed. The sample was then charged as-is into the moisture meter to assay the water. The syringe was again weighed, whereby the sample injected amount was calculated to determine the moisture content in the sample.

3) Gas Chromatography Analysis of a Carbonic Ester

Apparatus: GC-2010 system (manufactured by Shimadzu Corporation, Japan).

(1) Analysis Sample Solution Preparation

About 0.5 ml of dehydrated dimethylformamide or acetonitrile were charged into 0.4 g of a reaction solution. The resulting solution was further charged with about 0.04 g of toluene or diphenyl ether as an internal reference for use as the gas chromatography analysis sample solution.

(2) Gas Chromatography Analysis Conditions
Column: DB-1 (manufactured by J & W Scientific, U.S.A.)
Liquid phase: 100% dimethyl polysiloxane
Column length: 30 m
Column inner diameter: 0.25 mm
Film thickness: 1 μm
Column temperature: the temperature was elevated from 50° C. to 300° C. at a rate of 10° C./min.
Injection temperature: 300° C.
Detector temperature: 300° C.
Detection method: FID (3) Quantitative Analysis Quantitative analysis was carried out on the analysis sample solutions based on a calibration curve obtained from analysis of a standard sample of each standard substance.

4) Calculation of the Dialkyltin Alkoxide Yield

The dialkyltin alkoxide yield was calculated from the generated mole % of the number of moles of tin atoms of the obtained respective dialkyltin alkoxides (compounds represented by chemical formula (7) and/or chemical formula (16)) with respect to the number of moles of tin atoms of the starting material (compounds represented by chemical formula (1) and/or chemical formula (2)).

5) Calculation of the Aromatic Carbonic Ester Yield

The aromatic carbonic ester yield is shown by the weight % in the reaction solution, or was determined from the generated mole % of the obtained alkylaryl carbonate and diaryl carbonate with respect to the number of moles of the supplied material (dialkyl carbonate).

6) Number Average Molecular Weight of the Aromatic Polycarbonate

The number average molecular weight of the aromatic polycarbonate was measured by gel permeation chromatography (GPC).

Example 1

Preparation of a Mixed Solution of the Starting Material 1,1,3,3-tetrabutyl-1,3-bis(2-ethyl-butyloxy) distannoxane and the Reactant 2-ethyl-1-butanol A 1-liter recovery flask was charged with 24.9 g (0.1 mol) of dibutyltin oxide (manufactured by Aldrich Chemical Co., U.S.A., 98%) and 208 g (2.0 mol) of 2-ethyl-1-butanol (manufactured by Aldrich Chemical Co., U.S.A., 98%), whereby the flask contained the resulting white slurry mixture. The flask was attached to an evaporator (manufactured by Shibata Scientific Technology Ltd., R-144) connected to a thermoregulatory-equipped oil bath (manufactured by Masuda Corporation, Japan, OBH-24), a vacuum pump (manufactured by ULVAC Inc., Japan, G-50A), and a vacuum controller (manufactured by Okano Works Ltd., Japan, VC-10S). The oil bath temperature was set at 140° C. The flask was immersed in the oil bath, whereupon rotation of the evaporator was started. Rotation was continued for about 30 minutes while stirring and heating under atmospheric pressure with the evaporator purge valve open. The evaporator purge valve was then closed, and the pressure in the system was gradually lowered to about 60 kPa using the vacuum pump and the vacuum controller. This state was maintained for 1 hour, after which the flask was removed from the oil bath. The reaction solution had turned into a transparent liquid. The purge valve was gradually opened to return the system pressure to atmospheric pressure. The distillate was 9.9 g, transparent and had separated into 2 layers. Analysis of the distillate showed a water content of about 1 g. The flask was then removed from the oil bath and the purge valve was gradually opened to return the system pressure to atmospheric pressure. The flask yielded 218 g of reaction solution. Results of $^{119}$Sn, $^1$H and $^{13}$C-NMR analysis showed that, using dibutyltin oxide as a reference, the reaction solution contained an 11% yield of dibutyl-bis(2-ethyl-butyloxy)tin and about an 88% yield of 1,1,3,3-tetrabutyl-1,3-bis(2-ethyl-butyloxy)-distannoxane.

Obtaining Dibutyltin Dialkoxide Using a Column Reactor

Dibutyltin alkoxide was produced in a column reactor 1 such as that illustrated in FIG. 2. A 15 mm inner diameter and 850 mm total length (750 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (Tokyo Tokushu Kanaami K.K., Japan). The temperature of a lower flange portion of the tube reactor and the portion extending to about 60 mm from the flange was controlled using a heater set to 160°, while the temperature from the heating device upper portion to the upper flange of the tube reactor was controlled using a heater set to 140°.

Nitrogen gas was fed from the gas supply line 7 at 0.04 NL/min, and a feed pump was used to start feeding from the supply line 4 the mixed solution of the starting material and the reactant prepared as described above at 20 g/Hr. The holding time in the reactor was about 16 minutes. Low boiling point substances, including water, began to be extracted in gaseous form from the gas vent line 5 and high boiling point components began to flow out from the extraction line 6. Continuous feeding and continuous extraction operation was continued in the same state for 2 hours. Analysis of the liquid extracted from the extraction line 6 showed that, using dibutyltin oxide as a reference, the liquid contained a dibutyltin alkoxide consisting of dibutyl-bis(2-ethyl-butyloxy)tin in about a 94% yield and about 6% of 1,1,3,3-tetrabutyl-1,3-bis (2-ethyl-butyloxy)-distannoxane. Tributyltin(2-ethyl-butyloxide) had a yield of 0.2%. Upon cooling of the gas phase extracted from the vent line, a two-layer transparent liquid was obtained, in which moisture was present. The dehydration rate in the column reactor was 0.0033 mol/Hr, which was greater than the value 0.00025 mol/Hr calculated from expression (16).

Example 2

Preparation of the Starting Material 1,1,3,3-tetrabutyl-1,3-bis(2-ethyl-butyloxy)-distannoxane)

A 500 ml recovery flask was charged with 59.8 g (0.15 mol) of dibutyltin oxide (manufactured by Aldrich Chemical Co., U.S.A., 98%) and 122 g (1.2 mol) of 2-ethyl-1-butanol (manufactured by Aldrich Chemical Co., U.S.A., 98%), whereby the flask contained the resulting white slurry mixture. The flask was attached to an evaporator (manufactured by Shibata Scientific Technology Ltd., Japan, R-144) connected to a thermoregulator-equipped oil bath (manufactured by Masuda Corporation, Japan, OBH-24), a vacuum pump (manufactured by ULVAC Inc., Japan, G-50A), and a vacuum controller (manufactured by Okano Works Ltd., Japan, VC-10S). The oil bath temperature was set at 140° C. The flask was immersed in the oil bath, whereupon rotation of the evaporator was started. Rotation was continued for about 30 minutes while stirring and heating under atmospheric pressure with the evaporator purge valve open. The evaporator purge valve was then closed, and the pressure in the system was gradually lowered to about 70 kPa using the vacuum pump and the vacuum controller. This state was maintained for 1 hour, after which the flask was removed from the oil bath. The reactant had turned a transparent liquid. The purge valve was gradually opened to return the system pressure to atmospheric pressure. The distillate was 3.6 g, transparent and had separated into 2 layers. Analysis of the distillate showed a water content of about 2.2 g. The flask was then removed from the oil bath and the purge valve was gradually opened to return the system pressure to atmospheric pressure. The flask yielded 175 g of reaction solution. Results of $^{119}$Sn, $^{1}$H and $^{13}$C-NMR analysis showed that, using dibutyltin oxide as a reference, the reaction solution contained about an 99% yield of 1,1,3,3-tetrabutyl-1,3-bis(2-ethyl-butyloxy)-distannoxane.

Obtaining Dibutyltin Dialkoxide Using a Column Reactor

Dibutyltin alkoxide was produced in a column reactor 1 such as that illustrated in FIG. 2. A 15 mm inner diameter and 1,635 mm total length (1,450 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 160°, while the temperature from the heating device upper portion to the upper flange of the tube reactor was controlled using a heater set to 140°.

Nitrogen gas was fed from the gas supply line 7 at 0.04 NL/min, and a feed pump was used to start feeding from the supply line 4 a mixed solution of the starting material and the reactant prepared as described above at 20 g/Hr. The holding time in the reactor was about 32 minutes. Low boiling point substances, including water, began to be extracted in gaseous form from the extraction vent line 5 and high boiling point components began to flow out from the extraction line 6. Continuous feeding and continuous extraction operation was continued in this state for 2 hours. Analysis of the generated product extracted from the extraction line 6 showed that, using dibutyltin oxide as a reference, the generated product contained a dibutyltin alkoxide consisting of about a 94% yield of dibutyl-bis(2-ethyl-butyloxy)tin and about 6% of 1,1,3,3-tetrabutyl-1,3-bis(2-ethyl-butyloxy)-distannoxane. Tributyltin(2-ethyl-butyloxide) had a yield of 0.4%. Upon cooling of the gas phase extracted from the extraction vent line 5, a two-layer transparent liquid was obtained, in which moisture was present. The dehydration rate in the column reactor was 0.0033 mol/Hr, which was greater than the value 0.0005 mol/Hr calculated from expression (16).

Example 3

Synthesis of 1,1,3,3-tetrabutyl-1,3-bis(2-ethylhexyloxy)-distannoxane)

A 2-liter three-necked flask equipped with a moisture quantitative receiver that was connected to a thermometer, a three-way stopcock and a Dimroth condenser was charged with 199.8 g (0.80 mol) of dibutyltin oxide (manufactured by Aldrich Chemical Co., U.S.A., 98%), 1,045 g (8.0 mol) of 2-ethyl-1-hexanol (manufactured by Aldrich Chemical Co., U.S.A., 99.6% dehydrated) and 500 g of toluene (manufactured by Wako Pure Chemical Industries Ltd., Japan, for organic synthesis) whereby the flask contained the resulting white slurry mixture. The flask was immersed in an oil bath (manufactured by Fine, Japan, FWB-240) set to 130° C. After 30 minutes of heating under stirring, the temperature of the mixture was 119° C., and recovery of the water and the toluene in the moisture quantitative receiver began.

This state was maintained for about 3 hours, after which about 7.2 mL of water was recovered in the moisture quantitative receiver. The oil bath temperature was then lowered to 90° C., and once the mixture temperature had dropped, the moisture quantitative receiver was removed. The flask was connected to a connection pipe provided with a branch pipe, a Liebig condenser, a low-pressure connection pipe and two distillate recovery vessels. The pressure in the system was lowered to 29 kPa, and after toluene had been distilled off from the flask, the pressure in the system was further lowered to 0.6 kPa to distill off excess 2-ethyl-hexanol. The liquid amount recovered through distillation was 1,420 g, and 295.6 g of generated product was yielded in the flask. Results of $^{119}$Sn, $^{1}$H and $^{13}$C-NMR analysis showed that the generated product was at least 95% pure 1,1,3,3-tetrabutyl-1,3-bis(2-ethylhexyloxy)-distannoxane.

Obtaining Dibutyltin Dialkoxide Using a Column Reactor

Dibutyltin alkoxide was produced in a column reactor 1 such as that illustrated in FIG. 2. A 15 mm inner diameter and 850 mm total length (750 mm effective length) tube reactor made from SUS 316, which was furnished with a supply line 4 for injecting starting material, a supply line 8 for injecting reactant and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 160°, while the temperature from the heating device upper portion to the upper flange of the tube reactor was controlled using a heater set to 140°.

Nitrogen gas was fed from the supply line 7 at 0.04 NL/min, and a feed pump was used to start feeding the starting material prepared as described above at 3 g/Hr from the supply line 4, and feeding the reactant 2-ethyl-1-hexanol (manufactured by Aldrich Chemical Co., U.S.A., anhydrous 99.6%) at 17 g/Hr from the supply line 8. The holding time in the reactor was 15 minutes. Low boiling point substances, including water, began to be extracted in gaseous form from the extraction vent line 5 and high boiling point components began to flow out from the extraction line 6. Continuous feeding and continuous extraction operation was continued in this state for 2 hours. Analysis of the liquid extracted from the extraction line 6 showed that, using dibutyltin oxide as a reference, the liquid contained a dibutyltin alkoxide consisting of about a 45% yield of dibutyl-bis(2-ethyl-hexyloxy)tin and about 55% of 1,1,3,3-tetrabutyl-1,3-bis(2-ethyl-hexyloxy)-distannoxane. Tributyltin(2-ethyl-butyloxide) had a yield of 0.3%. Upon cooling of the gas phase extracted from the vent line, a two-layer transparent liquid was obtained, in which moisture was present. The dehydration rate in the column reactor was 0.0018 mol/Hr, which was greater than the value 0.000058 mol/Hr calculated from expression (16).

Example 4

Obtaining Dibutyltin Dialkoxide Using a Column Reactor

Dibutyltin alkoxide was produced in a column reactor 1 such as that illustrated in FIG. 2. A 15 mm inner diameter and 850 mm total length (750 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 160°, while the temperature from the heating device upper portion to the upper flange of the tube reactor was controlled using a heater set to 140°.

Nitrogen gas was fed from the nitrogen supply line 7 at 0.04 NL/min, and a feed pump was used to start feeding a slurry solution consisting of 19.9 g (0.08 mol) of the starting material dibutyltin oxide (manufactured by Aldrich Chemical Co., U.S.A., 98%) and 817 g (8 mol) of the reactant 2-ethyl-1-butanol (manufactured by Aldrich Chemical Co., U.S.A., 98%) at 8 g/Hr from the supply line 4. The holding time in the reactor was 35 minutes. Low boiling point substances, including water, began to be extracted in gaseous form from the extraction vent line 5 and high boiling point components began to flow out from the extraction line 6.

Continuous feeding and continuous extraction operation was continued in this state for 5 hours. Analysis of the generated product extracted from the extraction line 6 showed that, using dibutyltin oxide as a reference, the generated product contained a dibutyltin alkoxide consisting of about a 61% yield of dibutyl-bis(2-ethyl-butyloxy)tin and about 38% of 1,1,3,3-tetrabutyl-1,3-bis(2-ethyl-butyloxy)-distannoxane. Tributyltin(2-ethyl-butyloxide) had a yield of 0.1%. Upon cooling of the gas phase extracted from the vent line 5, a two-layer transparent liquid was obtained, in which moisture was present. The dehydration rate in the column reactor was 0.00062 mol/Hr, which was greater than the value 0.00005 mol/Hr calculated from expression (16).

Example 5

Obtaining Dibutyltin Dialkoxide Using a Column Reactor

Dibutyltin alkoxide was produced in a column reactor 1 such as that illustrated in FIG. 2. A 15 mm inner diameter and 850 mm total length (750 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 170°, while the temperature from the heating device upper portion to the upper flange of the tube reactor was controlled using a heater set to 150°.

Nitrogen gas was fed from the gas supply line 7 at 0.04 NL/min, and a feed pump was used to start feeding a mixed solution of the starting material 1,1,3,3-tetrabutyl-1,3-bis(2-ethyl-butyloxy)-distannoxane and the reactant 2-ethyl-1-butanol that was prepared in the same manner as that used in Example 1 at 8 g/Hr from the supply line 4. Subsequently, 2-ethyl-1-butanol (manufactured by Aldrich Chemical Co., U.S.A., 98%) was fed at 1 g/min from the gas supply line 7. The holding time in the reactor was 30 minutes. Low boiling point substances, including water, began to be extracted in gaseous form from the extraction vent line 5 and high boiling point components began to flow out from the extraction line 6.

Continuous feeding and continuous extraction operation was continued in this state for 2 hours. Analysis of the liquid extracted from the extraction line 6 showed that, using dibutyltin oxide as a reference, the generated product contained a dibutyltin alkoxide consisting of about a 48% yield of dibutyl-bis(2-ethyl-butyloxy)tin and about 52% of 1,1,3,3-tetrabutyl-1,3-bis(2-ethyl-butyloxy)-distannoxane. Tributyltin (2-ethyl-butyloxide) had a yield of 0.4%. Upon cooling of the gas phase extracted from the vent line, a two-layer transparent liquid was obtained, in which moisture was present.

Example 6

Obtaining Dibutyltin Dialkoxide Using a Combination of a Tank Reactor and a Column Reactor Dialkyltin alkoxide was produced using the combination of a tank reactor and a column reactor such as that illustrated in FIG. 3.

Employed were a baffled 1-liter stirring tank 9 made from SUS 304, comprising a supply line 15 for injecting reactant, a supply line 16 for injecting starting material and an extraction vent line 17 equipped with a distillation column on a stirring tank upper portion 11, a gas supply line 18 and a transfer line 19 on a stirring tank lower portion 12, a stirring device, temperature-control equipment, and the necessary instrumentation and valves for the operation of each line, and a column reactor 10 in which Helipack No. 3 (manufactured by Tokyo Tokushu Kanaami K.K., Japan) was packed into a 15 mm inner diameter and 1,635 mm total length (1,450 mm effective length) tube reactor made from SUS 316, which was furnished with temperature-control equipment and the necessary instrumentation and valves for the operation of each line, connected to a buffer tank 24, a relay line 25 for transferal from the buffer tank 24 to the column reactor, a supply line 22 for injecting reactant and a relay line 25 which both were connected to the reactor upper portion 13, an extraction vent line 21 equipped with a distillation column, a gas supply line 20 on a reactor lower portion 14 and an extraction line 23.

After the interior of the stirring tank 9 was purged with nitrogen, 390 g (3.0 mol) of reactant 2-ethyl-1-hexanol (manufactured by Aldrich Chemical Co., U.S.A., anhydrous 99.6%) were introduced from the supply line 15, and 199.8 g (0.80 mol) of starting material dibutyltin oxide (manufactured by Aldrich Chemical Co., U.S.A., 98%) were introduced from the supply line 16. Nitrogen gas was fed from the gas supply line 18 at 0.02 NL/min. The reactor was heated under stirring until the reaction solution reached 160° C., and the gas emerging from the extraction vent line 17 was extracted. The reaction was allowed to proceed in this state for 20 minutes, after which the reaction solution was continuously extracted at about 40 mL/min from the transfer line 19 while simultaneously continuously feeding the starting material and the reactant from the supply line 16 and supply line 15 at a rate such that the mole ratio was 1:3.75 so that the reactor interior liquid surface level was steady, whereby stable operation was started while continuously extracting gas emerging from the extraction vent line 17.

The reaction solution was transferred to the buffer tank 24 via the transfer line 19. Analysis of the buffer tank 24 liquid after 2 hours showed that, using dibutyltin oxide as a reference, the liquid contained primarily-generated dibutyltin alkoxide consisting of about a 5% yield of dibutyl-bis(2-ethyl-hexyloxy)tin and about 95% of 1,1,3,3-tetrabutyl-1,3-bis(2-ethyl-hexyloxy)-distannoxane. The dehydration rate in the tank reactor was 1.26 mol/Hr, which was greater than the value 0.13 mol/Hr calculated from expression (16).

(Next, the dibutyl-bis(2-ethyl-hexyloxy)tin yield in the reactor 10 was increased by taking the primary generated dibutyltin alkoxide that had accumulated in the buffer tank as the starting material)

The temperature of a lower flange portion of the reactor 10 and the portion extending to about 60 mm from the flange was controlled using a heater set to 160°, while the temperature from the heating device upper portion to the upper flange of the tube reactor was controlled using a heater set to 140°.

Nitrogen gas was fed from the gas supply line 20 at 0.04 NL/min, and a feed pump was used to start feeding the primary generated dibutyltin alkoxide prepared as described above as starting material at 5 g/Hr from the buffer tank 24 via the relay line 25, and the reactant 2-ethyl-1-hexanol (manufactured by Aldrich Chemical Co., U.S.A., anhydrous 99.6%) at 15 g/Hr from the supply line 22. The holding time in the reactor was 35 minutes. Low boiling point substances, including water, began to be extracted in gaseous form from the extraction vent line 21 and high boiling point components began to flow out from the extraction line 23.

Continuous feeding and continuous extraction operation was continued in this state for 2 hours. Analysis of the liquid extracted from the extraction line 23 showed that, using dibutyltin oxide as a reference, the liquid contained a dibutyltin alkoxide consisting of about a 75% yield of dibutyl-bis(2-ethyl-hexyloxy)tin and about 24% of 1,1,3,3-tetrabutyl-1,3-bis(2-ethyl-hexyloxy)-distannoxane. Tributyltin(2-ethyl-hexyloxide) had a yield of 0.9%. Upon cooling of the gas phase extracted from the vent line, a two-layer transparent liquid was obtained, in which moisture was present. The dehydration rate in the column reactor was 0.021 mol/Hr, which was greater than the value 0.00025 mol/Hr calculated from expression (16).

Example 7

Obtaining Dibutyltin Dialkoxide Using a Column Reactor

Dibutyltin alkoxide was produced in a column reactor 1 such as that illustrated in FIG. 2. A 15 mm inner diameter and 1,635 mm total length (1,450 mm effective length) tube reactor made from SUS 316, which was furnished with a supply line 4 and an extraction vent line 5 on a reactor upper portion 2, and a reactant secondary supply line 7 and an extraction line 6 on a reactor lower portion 3, was packed with Dickson packing 3 mm (Tokyo Tokushu Kanaami K.K., Japan). The temperature of a lower flange portion of the tube reactor and the portion extending to about 60 mm from the flange was controlled using a heater set to 170°, while the temperature from the heating device upper portion to the upper flange of the tube reactor was controlled using a heater set to 150°.

Nitrogen gas was fed from the gas supply line 7 at 0.04 NL/min, and a feed pump was used to start feeding a mixed solution of the starting material 1,1,3,3-tetrabutyl-1,3-bis(2-ethyl-butyloxy)-distannoxane and the reactant 2-ethyl-1-butanol that was prepared in the same manner as that used in Example 1 at 15 g/Hr from the supply line 4. The holding time in the reactor was 50 minutes. Low boiling point substances, including water, began to be extracted in gaseous form from the extraction vent line 5 and high boiling point components began to flow out from the extraction line 6.

Continuous feeding and continuous extraction operation was continued in this state for 4 hours. Analysis of the liquid extracted from the extraction line 6 showed that, using dibutyltin oxide as a reference, the liquid contained a dibutyltin alkoxide consisting of about a 63% yield of dibutyl-bis(2-ethyl-butyloxy)tin and about 36% of 1,1,3,3-tetrabutyl-1,3-bis(2-ethyl-butyloxy)-distannoxane. Tributyltin(2-ethyl-butyloxide) had a yield of 0.3%. Upon cooling of the gas phase extracted from the vent line, a two-layer transparent liquid was obtained, in which moisture was present. The dehydration rate in the column reactor was 0.0016 mol/Hr, which was greater than the value 0.00026 mol/Hr calculated from expression (16).

Example 8

Preparation of the starting material 1,1,3,3-tetraoctyl-1,3-di(butyloxy)-distannoxane A 2-liter recovery flask was charged with 217 g (0.6 mol) of dioctyltin oxide (manufactured by Wako Pure chemical Industries Ltd., Japan, 95%) and 445 g (6 mol) of 1-butanol (manufactured by Wako Pure chemical Industries Ltd., Japan, special grade), whereby the flask contained the resulting white slurry mixture. The flask was attached to an evaporator (manufactured by Shibata Scientific Technology Ltd., R-144) connected to a thermoregulator-equipped oil bath (manufactured by Masuda Corporation, Japan, OBH-24).

The oil bath temperature was set at 127° C. The flask was immersed in the oil bath, and rotation of the evaporator was started. Rotation was continued for about 150 minutes while stirring and heating under atmospheric pressure with the evaporator purge valve open. The flask was then removed from the oil bath and allowed to cool. The flask yielded 437 g of a viscous reaction solution. Results of $^{119}$Sn, $^1$H and $^{13}$C-NMR analysis showed that, using dioctyltin oxide as a reference, the reaction solution contained a 96% yield of 1,1,3,3-tetraoctyl-1,3-di(butyloxy)-distannoxane, and did not contain any dioctyl-di(butyloxy)tin.

Obtaining Dioctyltin Dialkoxide Using a Column Reactor

Dioctyltin alkoxide was produced in a column reactor 1 such as that illustrated in FIG. 2. A 15 mm inner diameter and 850 mm total length (750 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 150°, while the temperature from the heating device upper portion to the upper flange of the tube reactor was controlled using a heater set to 140°.

Carbon dioxide gas was fed from the gas supply line 7 at 80 mL/min, and a feed pump was used to start feeding the reaction solution obtained as described above (mixed solution consisting of the starting material 1,1,3,3-tetraoctyl-1,3-di(butyloxy)-distannoxane and the reactant 1-butanol) from the supply line 4 at 10 g/Hr. The holding time in the reactor was 37 minutes. The internal pressure of the reactor was measured at about 0.2 MPa-G using a pressure gauge. Low boiling point substances, including water, began to be extracted in gaseous form from the extraction vent line 5 and high boiling point components began to flow out from the extraction line 6.

Continuous feeding and continuous extraction operation was continued in this state for 4 hours. Analysis of the liquid extracted from the extraction line 6 showed that, using dioctyltin oxide as a reference, the liquid contained a dioctyltin alkoxide consisting of about a 43% yield of dioctyl-di(butyloxy)tin and 1,1,3,3-tetraoctyl-1,3-di(butyloxy)-distannoxane. Trioctyltinbutoxide had a yield of 0.1%. Upon cooling of the gas phase extracted from the vent line, a two-layer transparent liquid was obtained, in which moisture was present. The dehydration rate in the column reactor was 0.0017 mol/Hr, which was greater than the value 0.00025 mol/Hr calculated from expression (16).

Example 9

Preparation of the starting material 1,1,3,3-tetrabutyl-1,3-di(butyloxy)-distannoxane A 1-liter recovery flask was charged with 50 g (0.2 mol) of dibutyltin oxide (manufactured by Aldrich Chemical Co., U.S.A., 98%) and 178 g (2.4 mol) of 1-butanol (manufactured by Wako Pure chemical Industries Ltd., Japan, special grade), whereby the flask contained the resulting white slurry mixture. The flask was attached to an evaporator (manufactured by Shibata Scientific Technology Ltd., Japan, R-144) connected to a thermoregulator-equipped oil bath (manufactured by Masuda Corporation, Japan, OBH-24).

The oil bath temperature was set at 127° C. The flask was immersed in the oil bath, and rotation of the evaporator was started. Rotation was continued for about 2 hours while stirring and heating under atmospheric pressure with the evaporator purge valve open. The flask was then removed from the oil bath and allowed to cool. The flask yielded 212 g of a viscous reaction solution. Results of $^{119}$Sn, $^{1}$H and $^{13}$C-NMR analysis showed that, using dibutyltin oxide as a reference, the reaction solution contained a 98% yield of 1,1,3,3-tetrabutyl-1,3-di(butyloxy)-distannoxane, and did not contain any dibutyl-di(butyloxy)tin.

Obtaining Dibutyltin Dialkoxide Using a Column Reactor

Dibutyltin alkoxide was produced in a column reactor 1 such as that illustrated in FIG. 2. A 15 mm inner diameter and 850 mm total length (750 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 150°, while the temperature from the heating device upper portion to the upper flange of the tube reactor was controlled using a heater set to 140°.

Carbon dioxide gas was fed from the gas supply line 7 at 80 mL/min, and a feed pump was used to start feeding the reaction solution obtained as described above (mixed solution consisting of the starting material 1,1,3,3-tetrabutyl-1,3-di(butyloxy)-distannoxane and the reactant 1-butanol) from supply line 4 at 10 g/Hr. The holding time in the reactor was 37 minutes. The internal pressure of the reactor was measured at about 0.2 MPa-G using a pressure gauge. Low boiling point substances, including water, began to be extracted in gaseous form from the extraction vent line 5 and high boiling point components began to flow out from the extraction line 6.

Continuous feeding and continuous extraction operation was continued in this state for 4 hours. Analysis of the liquid extracted from the extraction line 6 showed that, using dibutyltin oxide as a reference, the liquid contained a dibutyltin alkoxide consisting of about a 90% yield of dibutyl-di(butyloxy)tin and 9% of 1,1,3,3-tetrabutyl-1,3-di(butyloxy)-distannoxane. Tributyltin butoxide had a yield of 0.06%. Upon cooling of the gas phase extracted from the vent line, a two-layer transparent liquid was obtained, in which moisture was present. The dehydration rate in the column reactor was 0.0033 mol/Hr, which was greater than the value 0.00025 mol/Hr calculated from expression (16).

Example 10

Preparation of the Starting Material 1,1,3,3-tetrabutyl-1,3-bis(2-methyl-1-propyloxy)-distannoxane A 1-liter recovery flask was charged with 50 g (0.2 mol) of dibutyltin oxide (manufactured by Aldrich Chemical Co., U.S.A., 98%) and 178 g (2.4 mol) of 2-methyl-1-propanol (manufactured by Wako Pure chemical Industries Ltd., Japan, special grade), whereby the flask contained a resulting white slurry mixture. The flask was attached to an evaporator (manufactured by Shibata Scientific Technology Ltd., Japan, R-144) connected to a thermoregulator-equipped oil bath (manufactured by Masuda Corporation, Japan, OBH-24).

The oil bath temperature was set at 118° C. The flask was immersed in the oil bath, and rotation of the evaporator was started. Rotation was continued for about 2 hours while stirring and heating under atmospheric pressure with the evaporator purge valve open. The flask was then removed from the oil bath and allowed to cool. The flask yielded 196 g of a viscous reaction solution. Results of $^{119}$Sn, $^{1}$H and $^{13}$C-NMR analysis showed that, using dibutyltin oxide as a reference, the reaction solution contained a 76% yield of 1,1,3,3-tetrabutyl-1,3-bis(2-methyl-1-propyloxy)-distannoxane, and did not contain any dibutyl-bis(2-methyl-1-propyloxy)tin.

Obtaining Dibutyltin Dialkoxide Using a Column Reactor

Dibutyltin alkoxide was produced in a column reactor 1 such as that illustrated in FIG. 2. A 15 mm inner diameter and 1,635 mm total length (1,450 mm effective length) tube reactor made from SUS 316, which was furnished with a supply line 4 and an extraction vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 150°, while the temperature from the heating device upper portion to the upper flange of the tube reactor was controlled using a heater set to 140°.

Carbon dioxide gas was fed from the gas supply line 7 at 80 mL/min, and a feed pump was used to start feeding the reaction solution obtained as described above (mixed solution consisting of the starting material 1,1,3,3-tetrabutyl-1,3-bis (2-methyl-1-propyloxy)-distannoxane and the reactant 2-methyl-1-propanol) from supply line 4 at 10 g/Hr. The holding time in the reactor was 22 minutes. The internal pressure of the reactor was measured at about 0.2 MPa-G using a pressure gauge. Low boiling point substances, including water, began to be extracted in gaseous form from the extraction vent line 5 and high boiling point components began to flow out from the extraction line 6.

Continuous feeding and continuous extraction operation was continued in this state for 4 hours. Analysis of the liquid extracted from the extraction line 6 showed that, using dibutyltin oxide as a reference, the liquid contained a dibutyltin alkoxide consisting of about a 97% yield of dibutyl-bis(2-methyl-1-propyloxy)tin and about 3% of 1,1,3,3-tetrabutyl-1,3-bis(2-methyl-1-propyloxy)-distannoxane. Tributyltin butyloxide had a yield of 0.02%. Upon cooling of the gas phase extracted from the vent line, a liquid was obtained, in which moisture was present. The dehydration rate in the column reactor was 0.0038 mol/Hr, which was greater than the value 0.00051 mol/Hr calculated from expression (16).

Example 11

Step 1: (Preparation of the Starting Material 1,1,3,3-tetrabutyl-1,3-bis(2-methyl-1-propyloxy)-distannoxane)

A 1-liter recovery flask was charged with 50 g (0.2 mol) of dibutyltin oxide (manufactured by Aldrich Chemical Co., U.S.A., 98%) and 178 g (2.4 mol) of 2-methyl-1-propanol (manufactured by Wako Pure Chemical Industries Ltd., Japan, special grade), whereby the flask contained the resulting white slurry mixture. The flask was attached to an evaporator (manufactured by Shibata Scientific Technology Ltd., R-144) connected to a thermoregulator-equipped oil bath (manufactured by Masuda Corporation, Japan, OBH-24).

The oil bath temperature was set at 118° C. The flask was immersed in the oil bath, and rotation of the evaporator was started. Rotation was continued for about 2 hours while stirring and heating under atmospheric pressure with the evaporator purge valve open. The flask was then removed from the oil bath and allowed to cool. The flask yielded 196 g of a viscous reaction solution. Results of $^{119}$Sn, $^1$H and $^{13}$C-NMR analysis showed that, using dibutyltin oxide as a reference, the reaction solution contained a 76% yield of 1,1,3,3-tetrabutyl-1,3-bis(2-methyl-1-propyloxy)-distannoxane using a dibutyltin oxide standard, and did not contain any dibutyl-bis (2-methyl-1-propyloxy)tin.

Step 2: (Obtaining Dibutyltin Dialkoxide using a Column Reactor)

Dibutyltin alkoxide was produced in a column reactor 1 such as that illustrated in FIG. 2. A 15 mm inner diameter and 1,635 mm total length (1,450 mm effective length) tube reactor made from SUS 316, which was furnished with a supply line 4 and a distillation vent line 5 on a reactor upper portion 2, and a gas supply line 7 and an extraction line 6 on a reactor lower portion 3, was packed with Helipack No. 3 (manufactured by Tokyo Tokushu Kanaami K.K., Japan). The temperature of a lower flange portion of the tube reactor and the portion extending to about 60 mm from the flange was controlled using a heater set to 150°, while the temperature from the heating device upper portion to the upper flange of the tube reactor was controlled using a heater set to 140°.

Carbon dioxide gas was fed from the gas supply line 7 at 80 mL/min, and a feed pump was used to start feeding the above-obtained reaction solution (mixed solution consisting of the starting material 1,1,3,3-tetrabutyl-1,3-bis(2-methyl-1-propyloxy)-distannoxane and the reactant 2-methyl-1-propanol) from supply line 4 at 10 g/Hr. The holding time in the reactor was 22 minutes. The internal pressure of the reactor was measured at about 0.2 MPa-G using a pressure gauge. Low boiling point substances, including water, began to be distilled off in gaseous form from the gas vent line 5 and the high boiling point components began to flow out from the extraction line 6.

Continuous feeding and continuous extraction operation of the liquid prepared in step 1 was continued in this state until the liquid ran out. The liquid extracted from the extraction line 6 was collected in a 1-liter relay tank made from SUS. Analysis of the collected liquid showed that, using dibutyltin oxide as a reference, the liquid contained a dibutyltin alkoxide consisting of a yield of about 97% of dibutyl-bis(2-methyl-1-propyloxy)tin and about 3% of 1,1,3,3-tetrabutyl-1,3-bis(2-methyl-1-propyloxy)-distannoxane. Tributyltin(2-methyl-1-propyloxide) had a yield of 0.03%. Upon cooling of the gas phase extracted from the vent line, moisture was removed using a multistage distillation column for recovery of 2-methyl-1-propanol. The dehydration rate in the column reactor was 0.0168 mol/Hr, which was greater than the value 0.000648 mol/Hr calculated from expression (16).

Step 3: (Obtaining a Carbonic Ester from Dialkyltin Alkoxide)

The reaction solution collected in the relay tank in Step 2 was fed at 3 g/min into thin film distillation equipment (manufactured by Shibata Scientific Technology Ltd., Japan, E-420) set to 130° C. and about 65 Pa using a feed pump (manufactured by Shimadzu Corporation, Japan, LC-10AT) to remove the volatile components. The non-volatile components were cooled and recovered, whereby about 74 g of recovered liquid was yielded. The recovered liquid was charged into a 200 mL autoclave (manufactured by Toyo Koatsu Co., Ltd., Japan) and the lid was closed. The autoclave interior was purged with nitrogen gas, and then the secondary pressure of a carbon dioxide cylinder connected to the autoclave via SUS tubing and a valve was set to 4 MPa. The valve was then opened, and carbon dioxide gas was introduced into the autoclave.

After stirring for 10 minutes the valve was closed. The temperature was then raised to 120° C. under stirring. At this time, the internal pressure of the autoclave was adjusted using a back pressure valve so that the pressure was maintained at 4 MPa. The reaction was allowed to proceed in this state for 4 hours, after which the internal pressure of the autoclave was returned to atmospheric pressure by gently purging the carbon dioxide from the purge line. The liquid in the autoclave was quickly extracted from an extraction line attached to the bottom of the autoclave, whereby a transparent reaction solution was obtained. Di(2-methyl-propyl) carbonate was obtained in a 40% yield using dibutyltin oxide as a reference. The transparent reaction solution was fed at 3 g/min into thin film distillation equipment (manufactured by Shibata Scientific Technology Ltd., Japan, E-420) set to 130° C. and about 65 Pa using a feed pump (manufactured by Shimadzu Corporation, Japan, LC-10AT) to remove volatile components including di(2-methyl-propyl) carbonate. The non-volatile components were cooled and recovered, whereby about 62 g of recovered liquid was yielded. The volatile components including di(2-methyl-propyl) carbonate were cooled to form a liquid, in which tributyltin(2-methyl-1-propyl oxide) was not detected. Chlorine was also not detected from the results of chlorine analysis.

$^{119}$Sn, $^{1}$H and $^{13}$C-NMR analysis of the recovered liquid showed that the liquid contained 1,1,3,3-tetrabutyl-1,3-bis(2-methyl-1-propyloxy)-distannoxane, and did not contain dibutyl-bis(2-methyl-1-propyloxy)tin.

Step 4: (Obtaining Dialkyltin Alkoxide after Carbonic Ester Production using the Recovered Liquid as a Starting Material)

The recovered liquid recovered in Step 3 was charged with the 2-methyl-1-propanol recovered by dehydration in the multistage distillation column in Step 1 as a reaction solution and 2-methyl-1-propanol (manufactured by Wako Pure Chemical Industries Ltd., special grade) for any shortfall, such that, on a molar basis, the propanols were about ten times of tin atoms contained in the organic tin compound, such as 1,1,3,3-tetrabutyl-1,3-bis(2-methyl-1-propyloxy)-distannoxane, contained in the liquid recovered in step-3, to thereby prepare a mixed solution of the starting material and the reactant. Operation was carried out in the same manner as that in Step 2, except that the above-described mixed solution was used for the liquid supplied from supply line 4. Continuous feeding and continuous extraction operation was continued until the mixed solution ran out.

The liquid extracted from the extraction line 6 was collected in a 1-liter relay tank made from SUS. Analysis of the collected liquid showed that, using dibutyltin oxide as a reference, the liquid contained a dibutyltin alkoxide consisting of a yield of about 97% dibutyl-bis(2-methyl-1-propyloxy)tin and about 3% of 1,1,3,3-tetrabutyl-1,3-bis(2-methyl-1-propyloxy)-distannoxane. Upon cooling of the gas phase extracted from the vent line, moisture was removed using a multistage distillation column for recovery of 2-methyl-1-propanol.

Next, Step 3 and Step 4 were repeated 3 times, wherein the solution in the relay tank obtained by the third rendition of Step 4 contained a dibutyltin alkoxide consisting of a yield of about 95% dibutyl-bis(2-methyl-1-propyloxy)tin and about 2% of 1,1,3,3-tetrabutyl-1,3-bis(2-methyl-1-propyloxy)-distannoxane using dibutyltin oxide as a reference. The dehydration rate in the column reactor was greater than the value calculated from expression (16). Tributyltin(2-methyl-1-propyloxide) had a yield of 0.05%.

Comparative Example 1

Continuous Extraction Method of Only the Low Boiling Point Constituents

A 1-liter recovery flask was charged with 50 g (0.2 mol) of a starting material dibutyltin oxide (manufactured by Aldrich Chemical Co., U.S.A., 98%) and 178 g (2.4 mol) of a reactant 2-methyl-1-propanol (manufactured by Wako Pure Chemical Industries Ltd., Japan, special grade), whereby the flask contained the resulting white slurry mixture. The flask was attached to an evaporator (manufactured by Shibata Scientific Technology Ltd., R-144) connected to a thermoregulator-equipped oil bath (manufactured by Masuda Corporation, Japan, OBH-24). The oil bath temperature was set at 118° C. The flask was immersed in the oil bath, and rotation of the evaporator was started. Rotation was continued for about 8 hours while stirring and heating under atmospheric pressure with the evaporator purge valve open. The flask was then removed from the oil bath and allowed to cool. The flask yielded 139 g of a viscous reaction solution. Results of $^{119}$Sn, $^{1}$H and $^{13}$C-NMR analysis using dibutyltin oxide as a reference showed that the reaction solution contained a 78% yield of 1,1,3,3-tetrabutyl-1,3-bis(2-methyl-propyloxy)-distannoxane, and did not contain any dibutyl-bis(2-methyl-1-propyloxy)tin.

Comparative Example 2

Continuous Distillation Method of Only the Low Boiling Point Constituents

A 1-liter recovery flask equipped with a condenser and a Dean-Stark trap was charged with a starting material of 25 g (0.1 mol) of dibutyltin oxide (manufactured by Aldrich Chemical Co., U.S.A.) and a reactant of 390 g (3.0 mol) of 2-ethyl-1-hexanol (manufactured by Aldrich Chemical Co., U.S.A., 99.6% anhydrous) and 300 mL of toluene (manufactured by Wako Pure Chemical Industries Ltd., Japan, special grade). The resulting mixture was refluxed under heating for 12 hours in an oil bath in which the temperature was maintained at 120° C. while stirring with a stirrer. The Dean-Stark trap yielded 0.8 mL of water. Using dibutyltin oxide as a reference, the flask yielded about a 95% yield of 1,1,3,3-tetrabutyl-1,3-bis(2-ethyl-hexyloxy)-distannoxane, and did not yield any dibutyl-bis(2-ethyl-hexyloxy)tin.

Comparative Example 3

Preparation of the Starting Material 1,1,3,3-tetrabutyl-1,3-bis(2-methyl-1-propyloxy)-distannoxane Using the same method as that of Comparative Example 1, 139 g of a liquid containing 78% of starting material 1,1,3,3-tetrabutyl-1,3-bis(2-methyl-1-propyloxy)-distannoxane using dibutyltin oxide as a reference was obtained from dibutyltin oxide and 2-methyl-1-propanol.

Continuous Extraction of Only the Low Boiling Point Constituents Using a Tank Reactor A 500 mL autoclave (manufactured by Toyo Koatsu Co., Ltd., Japan) made from SUS and equipped with a thermoregulator, a stirring apparatus, a nitrogen line and a purge line, was charged with the above-described liquid and 74 g (1 mol) of reactant 2-methyl-1-propanol (manufactured by Wako Pure Chemical Industries Ltd., Japan, special grade), and the lid was closed. After the autoclave interior was purged with nitrogen gas, stirring was started. The autoclave contents were heated at a temperature set to 125° C. under stirring with the purge valve open. Gaseous components that were generated as a result of the rise in temperature were removed by distillation from the purge line for 2 hours. Distillation of the low boiling point components was checked to see whether it had substantially stopped, and the autoclave was left to cool. Analysis of the reaction solution in the autoclave interior using $^{119}$Sn, $^{1}$H and $^{13}$C-NMR showed that, using dibutyltin oxide as a reference, the reaction solution contained 79% of 1,1,3,3-tetrabutyl-1,3-bis(2-methyl-1-propyloxy)-distannoxane from the dibutyltin oxide and 2-methyl-1-propanol. No dibutyl-bis(2-methyl-1-propyloxy)tin was yielded.

Comparative Example 4

Continuous Distillation Method of Only the Low Boiling Point Constituents

A 1-liter two-necked flask equipped with a condenser and a Dean-Stark trap was charged with 129 g (0.5 mol) of starting material dibutyltin oxide (manufactured by Aldrich Chemical Co., U.S.A.) and 510 g (5.0 mol) of reactant 2-ethyl-1-butanol (manufactured by Aldrich Chemical Co., U.S.A., 98%). Distillation was carried out while stirring with a stirrer by heating for 6 hours in an oil bath in which the temperature was maintained at 160° C., wherein the generated water and 2-ethyl-1-butanol were reacted while being distilled off. After being allowed to cool, using dibutyltin oxide as a reference, the flask contained a yield of about 8% dibutyl-bis(2-ethyl-butyloxy)tin, 80% 1,1,3,3-tetrabutyl-1,3-bis(2-ethyl-butyloxy)-distannoxane and 6% tributyltin(2-ethyl-butyloxide). The dehydration rate in the reactor was 0.045 mol/Hr, which was lower than the value 0.273 mol/Hr calculated from expression (16).

Comparative Example 5

Continuous Extraction Method of Only the Low Boiling Point Constituents, Reacted Under High-Temperature A 1-liter two-necked flask equipped with a Liebig condenser and a sampling port was charged with 129 g (0.5 mol) of starting material dibutyltin oxide (manufactured by Aldrich Chemical Co., U.S.A.) and 651 g (5.0 mol) of reactant 2-ethyl-1-hexanol (manufactured by Aldrich Chemical Co., U.S.A., 99.6% anhydrous). Distillation was carried out while stirring with a stirrer by heating for 2 hours in an oil bath in which the temperature was maintained at 190° C., wherein the generated water and 2-ethyl-1-hexanol were reacted while being distilled off. After being allowed to cool, using dibutyltin oxide as a reference, the flask contained a yield of about 40% dibutyl-bis(2-ethyl-hexyloxy)tin, 1% 1,1,3,3-tetrabutyl-1,3-bis(2-ethyl-hexyloxy)-distannoxane and 29% tributyltin(2-ethyl-hexyloxide). The dehydration rate in the reactor was 0.175 mol/Hr, which was lower than the value 3.44 mol/Hr calculated from expression (16).

Comparative Example 6

Synthesis of a Carbonic Ester from a Dibutyltin Alkoxide Containing a Tributyltin Compound and a Chlorine-Containing Compound Nitrogen gas (0.3 L/min) was flowed through a 100 mL recovery flask equipped with a three-way stopcock. The flask was charged using a gas-tight syringe (manufactured by Hamilton Company, 1050TLL) with 23.80 g (0.063 mol) of dibutyltin dibutoxide (manufactured by Azmax co., tributyltin compound content of 1.5 mol %, chlorine atom content of 7,600 ppm) and 26.44° g (0.30 mol) of 3-methyl-1-butanol (manufactured by Aldrich Chemical Co., U.S.A., >99%. The flask was then shaken, to thereby uniformly mix the resulting solution. This mixed solution was transferred using a syringe to a 150 mL pressure vessel made from SUS316L (manufactured by Swagelok Company, 316L-50DF4-150) equipped with a valve. The valve was closed and the vessel was sealed. A 200 mL high-pressure vessel (manufactured by Toyo Koatsu Co., Ltd., Japan, FC Series Autoclave System) equipped with a magnetic induction stirrer, a mantle heater, a thermometer, a pressure gauge, two gas purge valves and a liquid sampling valve was connected to a nitrogen gas cylinder equipped with a pressure regulator via SUS316 tubing. The nitrogen gas cylinder pressure was set to 0.5 MPa using the pressure regulator. The high-pressure vessel gas purge valve was opened, and nitrogen was introduced until the pressure in the vessel reached 0.5 MPa. A separate gas valve was opened, whereby the pressure in the vessel returned to atmospheric pressure. This operation was repeated 3 times, whereby the vessel interior was purged with nitrogen. The mixed solution-containing pressure vessel was weighed. After connecting to the high-pressure vessel liquid sampling valve, the pressure in the pressure vessel was raised to 0.5 MPa using nitrogen. The liquid sampling valve was slowly opened, whereby the mixed solution was introduced into the high-pressure vessel. The mixed solution amount introduced into the high-pressure vessel was determined from the change of the pressure vessel weight. Heating of the autoclave was started, the stirrer was operated at a revolution of 450 rpm, and the mixed solution was heated at 120° C. A carbon dioxide cylinder (manufactured by Showa Tansan Co., Ltd., purity of 99.99 vol %) equipped with a pressure regulator was then connected to a gas purge valve of the high-pressure vessel. The carbon dioxide cylinder secondary pressure was set to 4.5 MPa by the pressure regulator. The gas purge valve was opened, whereby carbon dioxide gas was introduced into the high-pressure vessel. The pressure was adjusted to 4.0 MPa. After heating and stirring for 2 hours, the heater was removed from the vessel, and the vessel was left to cool until the vessel internal temperature reached room temperature. The gas purge valve were opened, whereby carbon dioxide gas was removed until the vessel internal pressure reached 0.05 MPa. The liquid sampling valve was connected to a 100 mL three-necked flask equipped with a three-way stopcock using Teflon (registered trademark) tubing. The valve was opened and the mixed solution was transferred to the flask. Calculation by gravimetry of the flask showed that 22.07 g of mixed solution had been collected. Next, the flask was connected to a connection pipe provided with a branch pipe, a thermometer, a Liebig condenser, a low-pressure connection pipe and two distillate recovery vessels. The flask was immersed in an oil bath to raise the mixed solution temperature to 120° C. Using a vacuum pump and a vacuum controller, the pressure was gradually lowered to about 32 kPa. This state was maintained for about 1.5 hours, whereby 11.51 g of a fraction 1 having a steam temperature of 96° C. was obtained. Pressure in the system was subsequently further lowered to 0.15 to 0.06 kPa. This state was maintained for about 1 hour, whereby 2.30 g of a fraction 2 having a steam temperature of from 64 to 80° C. was obtained. The results of GC-FID analysis for fraction 2 showed a content of 0.20 g of di-3-methylbutyl carbonate. In addition, the results of chlorine analysis showed a chlorine atom content of 70 ppm. The results of $^{119}$Sn-NMR analysis showed that a tributyltin compound was yielded at 0.7% by weight.

Comparative Example 7

Preparation of a Carbonic Ester from Dibutyltin Alkoxide Containing a Large Quantity of Tributyltin Compound and Chlorine-Containing Compound A high-pressure vessel was charged with 23.56 g (0.079 mol) of dibutyltin dimethoxide (manufactured by Aldrich Chemical Co., U.S.A., tributyltin compound content of 3.5 mol %) and 33.06 g (0.38 mol) of 3-methyl-1-butanol (manufactured by Aldrich Chemical Co., U.S.A., ≧99% in the same manner as in Comparative Example 6. Heating and stirring were also carried out in the same manner. After the mixed solution temperature had been lowered and carbon dioxide gas removed in the same manner, 37.51 g of mixed solution was collected in the 100 mL three-necked flask equipped with a three-way stopcock. Next, the flask was connected to a connection pipe provided with a branch pipe, a thermometer, a Liebig condenser, a low-pressure connection pipe and two distillate recovery vessels. The flask was immersed in an oil bath to raise the mixed solution temperature to 120° C. Using a vacuum pump and a vacuum controller, the pressure was gradually lowered to 97 to 13 kPa. This state was maintained for about 1.5 hours, whereby 16.85 g of a fraction 1 having a steam temperature of from 54 to 98° C. was obtained. Pressure in the system was subsequently further lowered to 0.06 to 0.2 kPa. This state was maintained for about 1 hour, whereby 1.71 g of a fraction 2 having a steam temperature of from 79 to 81° C. was obtained. The results of GC-FID analysis for fraction 2 showed a content of 1.61 g of di-3-methylbutyl carbonate. In addition, it was confirmed from $^{119}$Sn-NMR analysis that 1.2% by weight of a tributyltin compound was mixed in the carbonic acid ester.

Example 12

Preparation of the Starting Material 1,1,3,3-tetrabutyl-1,3-di(butyloxy)-distannoxane A 2,000 mL recovery flask was charged with 542 g (2.18 mol) of dibutyltin oxide (manufactured by Aldrich Chemical Co., U.S.A.) and 1,400 g (18.9 mol) of 1-butanol (manufactured by Wako Pure Chemical Industries Ltd., Japan), whereby the flask contained the resulting white slurry mixture. The flask was attached to an evaporator (manufactured by Shibata Scientific Technology Ltd., R-144) connected to a thermoregulator-equipped oil bath (manufactured by Masuda Corporation, Japan, OBH-24), a vacuum pump (manufactured by ULVAC Inc., Japan, G-50A), and a vacuum controller (manufactured by Okano Works Ltd., Japan, VC-10S). The evaporator purge valve outlet was connected to a nitrogen gas line flowing at atmospheric pressure. The evaporator purge valve was closed to thereby lower the pressure in the system. The purge valve was then gradually opened, and nitrogen was flowed into the system to return the system to atmospheric pressure. The oil bath temperature was set at 126° C. The flask was immersed in the oil bath, and rotation of the evaporator was started. Rotation was continued for about 30 minutes while stirring and heating under atmospheric pressure with the evaporator purge valve open, whereby the reaction solution came to the boil, to thereby start distillation of the low boiling point constituents. This state was maintained for 6 hours, after which the purge valve was closed, whereby the system internal pressure was slowly lowered. The remaining low boiling point constituents were distilled off when the system internal pressure was around 76 to 54 kPa. Once the low boiling point constituents stopped being distilled off, the flask was removed from the oil bath. The reaction solution had tuned transparent. The distilled off liquid was 1,255 g, transparent and had separated into 2 layers. Analysis of the distilled off liquid showed that it contained about 19.6 g of water. The flask was then removed from the oil bath and the purge valve was slowly closed to return the system internal pressure to atmospheric pressure. The flask yielded 686 g of the reaction solution. Results of $^{119}$Sn, $^1$H and $^{13}$C-NMR analysis showed that, using dibutyltin oxide as a reference, the generated product 1,1,3,3-tetrabutyl-1,3-di(butyloxy)-distannoxane was obtained in a 99% yield. The same procedure was repeated 6 times, whereby a total of 4,120 g of 1,1,3,3-tetrabutyl-1,3-di(butyloxy)-distannoxane was obtained.

Obtaining Dibutyltin Dialkoxide using a Column Reactor

Dibutyltin alkoxide was produced in a column reactor 31 such as that illustrated in FIG. 4. A 50 mm inner diameter and 4,000 mm total length column reactor 31 made from SUS 316, which was furnished with a supply line 26, a supply line 27, a heat exchanger 28, a low boiling point component recovery line 34, a condenser 35, a gas-liquid separator 36, a back pressure valve 37, a vent line 38, and a liquid-phase recovery line 39 on a reactor upper portion 32, and a gas supply line 29, a heat exchanger 30 and an extraction line 40 on a reactor lower portion 33, was packed with Goodroll Type A (Tokyo Tokushu Kanaami K.K., Japan). The temperature of the reactor was adjusted using a heater set to 140.0.

From the gas supply line 29, 1-butanol (manufactured by Wako Pure Chemical Industries Ltd., Japan, industrial product) was fed at 399 g/Hr and carbon dioxide was fed at 3 NL/Hr. All of the 1-butanol was vaporized by the heat exchanger 30 and fed to the reactor lower portion 33. A feed pump was used to start feeding the starting material 1,1,3,3-tetrabutyl-1,3-di(butyloxy)-distannoxane from supply line 26 at 210 g/Hr and the reaction solution 1-butanol (manufactured by Wako Pure Chemical Industries Ltd., Japan, industrial product) from supply line 27 at 951 g/Hr. The holding time in the reactor was 30 minutes. The liquid temperature inside the reactor was 140° C., and the pressure of the back pressure valve 37 was adjusted to 0.096 MPa-G. Continuous supply was continued in this state for 10 hours, after which the system reached a steady state. Low boiling point components flowed from the reactor upper portion 32 and through the low boiling point component recovery line for liquefaction at the condenser 35, and were thereby recovered from the liquid-phase recovery line 39 at 753 g/Hr. Furthermore, from the reactor lower portion 33, a dibutyltin alkoxide-containing component was recovered at 807 g/Hr from the extraction line 40. Analysis of the recovered liquid showed that, using dibutyltin oxide as a reference, the liquid contained dibutyltin alkoxide consisting of a yield of about 41.3% dibutyl-di(butyloxy)tin and 58.7% of 1,1,3,3-tetrabutyl-1,3-di(butyloxy)-distannoxane. Tributyltin butoxide had a yield of 0.04%. Meanwhile, the liquid recovered from the liquid-phase recovery line 39 was transparent and contained 2,500 ppm of moisture. The dehydration rate in the column reactor was 0.144 mol/Hr, which was greater than the value 0.0015 mol/Hr calculated from expression (16).

Example 13

Obtaining Dibutyltin Dialkoxide Using a Column Reactor

Dibutyltin alkoxide was produced in a column reactor 31 such as that illustrated in FIG. 4. A 50 mm inner diameter and 4,000 mm total length column reactor 31 made from SUS 316, which was furnished with a supply line 26, a supply line 27, a heat exchanger 28, a low boiling point component recovery line 34, a condenser 35, a gas-liquid separator 36, a back pressure valve 37, a vent line 38, and a liquid-phase recovery line 39 on a reactor upper portion 32, and a gas supply line 29, a heat exchanger 30 and an extraction line 40 on a reactor lower portion 33, was packed with Metal Gauze CY (Sulzer Chemtech Ltd., Switzerland). The temperature of the reactor was adjusted using a heater set to 140° C.

From the gas supply line 29, 1-butanol (manufactured by Wako Pure Chemical Industries Ltd., Japan, industrial product) was fed at 566 g/Hr and carbon dioxide was fed at 3 NL/Hr. All of the 1-butanol was vaporized by the heat exchanger 30 and fed to the reactor lower portion 33. A feed pump was used to start supplying the starting material 1,1,3,3-tetrabutyl-1,3-di(butyloxy)-distannoxane prepared in the same manner as in Example 12 from supply line 26 at 280 g/Hr and the reaction solution 1-butanol (manufactured by Wako Pure Chemical Industries Ltd., Japan, industrial product) from supply line 27 at 1,330 g/Hr. The holding time in the reactor was 13 minutes. The liquid temperature inside the reactor was 140° C., and the pressure of the back pressure valve 37 was adjusted to 0.096 MPa-G. Continuous supply was continued in this state for 10 hours, after which the system reached a steady state. Low boiling point components flowed from the reactor upper portion 32 and through the low boiling point component recovery line for liquefaction at the condenser 35, and were thereby recovered from the liquid-phase recovery line 39 at 1,006 g/Hr. Furthermore, from the reactor lower portion 33 a dibutyltin alkoxide-containing component was recovered at 1,170 g/Hr from the extraction line 40. Analysis of the liquid recovered from the generated product extraction line 40 showed that, using dibutyltin oxide as a reference, the liquid contained a dibutyltin alkoxide consisting of a yield of about 37.5% dibutyl-di(butyloxy)tin and 62.4% of 1,1,3,3-tetrabutyl-1,3-di(butyloxy)-distannoxane. Tributyltin butoxide had a yield of 0.022%. Meanwhile, the liquid recovered from the liquid-phase recovery line 39 was transparent and contained 2,200 ppm of moisture. The dehydration rate in the column reactor was 0.39 mol/Hr, which was greater than the value 0.0015 mol/Hr calculated from expression (16).

Example 14

Obtaining Dibutyltin Dialkoxide Using a Column Reactor

Dibutyltin alkoxide was produced in a column reactor 46 such as that illustrated in FIG. 5. A column reactor 46 was equipped with a supply line 41, a supply line 42, a heat exchanger 43, a low boiling point component recovery line 49, a condenser 50, a low boiling point component storage tank 51, a back pressure valve 52, a vent line 53, and a liquid-phase recovery line 54 in a reactor upper portion 47, and a circulation line 44 for circulating reaction solution that has accumulated at a reactor lower portion, a reboiler 45 and an extraction line 55 on a reactor lower portion 48 and 50 mm inner diameter and 3,500 mm total length downcomer-equipped sieve trays made from SUS 316. Each sieve tray possessed about 9 g of hold-up. The trays were installed in 50 mm intervals. The temperature of the column reactor was adjusted using a heater set to 140°.

A feed pump was used to start feeding the starting material 1,1,3,3-tetrabutyl-1,3-di(butyloxy)-distannoxane prepared in the same manner as in Example 12 from supply line 41 at 280 g/Hr and the reactant 1-butanol (manufactured by Wako Pure Chemical Industries Ltd., Japan, industrial product) from supply line 42 at 1,400 g/Hr. The holding time in the reactor was 24 minutes. Reaction solution which accumulated in the reactor lower portion was circulated at 6,000 g/Hr by the circulation line 44 and the reboiler 45 while heating at a temperature of about 140° C. The liquid temperature inside the reactor was 140° C., and the pressure of the back pressure valve 52 was adjusted to 0.096 MPa-G. Continuous supply was continued in this state for 10 hours, after which the system reached a steady state. Low boiling point components were flowed from the reactor upper portion 47 and through the low boiling point component recovery line 49 for liquefaction at the condenser 50, and were thereby recovered from the liquid-phase recovery line 54 at 1,010 g/Hr. Furthermore, from the reactor lower portion 48, a dibutyltin alkoxide-containing component was recovered at 670 g/Hr from the extraction line 55. Analysis of the recovered liquid showed that, using dibutyltin oxide as a reference, the liquid contained a dibutyltin alkoxide consisting of a yield of about 44.4% dibutyl-di(butyloxy)tin and 55.0% of 1,1,3,3-tetrabutyl-1,3-di(butyloxy)-distannoxane. Tributyltin butoxide had a yield of 0.05%. Meanwhile, the liquid recovered from the liquid-phase recovery line 54 was transparent and contained 2,300 ppm of moisture. The dehydration rate in the column reactor was 0.20 mol/Hr, which was greater than the value 0.0015 mol/Hr calculated from expression (16).

Example 15

Obtaining Dibutyltin Dialkoxide Using a Column Reactor

Dibutyltin alkoxide was produced in a column reactor 46 such as that illustrated in FIG. 5. A 50 mm inner diameter and 4,000 mm total length column reactor 46 made from SUS 316, which was furnished with a supply line 41, a supply line 42, a heat exchanger 43, a low boiling point component recovery line 49, a condenser 50, a low boiling point component storage tank 51, a back pressure valve 52, a vent line 53 and a liquid-phase recovery line 54 on a reactor upper portion 47, and a circulation line 44 for circulating reaction solution that has accumulated at a reactor lower portion, a reboiler 45 and an extraction line 55 on a reactor lower portion 48, was packed with Mellapak 750Y (Sulzer Chemtech Ltd., Switzerland). The temperature of the reactor was adjusted using a heater set to 140° C.

A feed pump was used to start feeding the starting material 1,1,3,3-tetrabutyl-1,3-di(butyloxy)-distannoxane prepared in the same manner as in Example 12 from supply line 41 at 280 g/Hr and the reactant 1-butanol (manufactured by Wako Pure Chemical Industries Ltd., Japan, industrial product) from supply line 42 at 1,330 g/Hr. The holding time in the reactor was 13 minutes. Reaction solution which accumulated in the reactor lower portion was circulated at 6,000 g/Hr by the circulation line 44 and the reboiler 45 while heating at a temperature of about 140° C. The liquid temperature inside the reactor was 140° C., and the pressure of the back pressure valve 52 was adjusted to 0.096 MPa-G. Continuous supply was continued in this state for 10 hours, after which the system reached a steady state. Low boiling point components flowed from the reactor upper portion 47 and through the low boiling point component recovery line 49 for liquefaction at the condenser 50, and were thereby recovered from the liquid-phase recovery line 54 at 1,006 g/Hr. Furthermore, from the reactor lower portion 48, a dibutyltin alkoxide-containing component was recovered at 604 g/Hr from the extraction line 55. Analysis of the liquid recovered from the extraction line 55 showed that, using dibutyltin oxide as a reference, the liquid contained a dibutyltin alkoxide consisting of a yield of about 46.3% dibutyl-di(butyloxy)tin and 53.6% of 1,1,3,3-tetrabutyl-1,3-di(butyloxy)-distannoxane. Tributyltin butoxide had a yield of 0.022%. Meanwhile, the liquid recovered from the liquid-phase recovery line 54 was transparent and contained 2,200 ppm of moisture. The dehydration rate in the column reactor was 0.21 mol/Hr, which was greater than the value 0.00081 mol/Hr calculated from expression (16).

Example 16

Obtaining Dibutyltin Dialkoxide Using a Column Reactor

Dibutyltin alkoxide was produced in a column reactor 61 such as that illustrated in FIG. 6. A 50 mm inner diameter and 4,000 mm total length column reactor 61 made from SUS 316, which was furnished with a supply line 56, a supply line 57, a heat exchanger 58, a low boiling point component recovery line 65, a condenser 66, a low boiling point component storage tank 67, a back pressure valve 68, a vent line 69 and a liquid-phase recovery line 70 on a reactor upper portion 63, a low boiling point component recovery line 71, a condenser 72, a low boiling point component storage tank 73, a gas line 74 and a liquid-phase recovery line 75 on a reactor middle portion 62, and a circulation line 59 for circulating reaction solution that has accumulated at a reactor lower portion, a reboiler 60 and an extraction line 76 on a reactor lower portion 64, was packed with Mellapak 750Y (Sulzer Chemtech Ltd., Switzerland). The temperature of the reactor was adjusted using a heater set to 140° C.

A feed pump was used to start feeding the starting material 1,1,3,3-tetrabutyl-1,3-di(butyloxy)-distannoxane prepared in the same manner as in Example 12 from supply line 56 at 280 g/Hr and the reactant 1-butanol (manufactured by Wako Pure Chemical Industries Ltd., Japan, industrial product) from supply line 57 at 1,332 g/Hr. The holding time in the reactor was 13 minutes. Reaction solution which accumulated in the reactor lower portion was circulated at 6,000 g/Hr by the circulation line 59 and the reboiler 60 while heating at a temperature of about 140° C. The liquid temperature inside the reactor was 140° C., and the pressure of the back pressure valve 68 was adjusted to 0.096 MPa-G. Continuous supply was continued in this state for 10 hours, after which the system reached a steady state. Low boiling point components flowed from the reactor upper portion 63 and through the low boiling point component recovery line 65 for liquefaction at the condenser 66, and were thereby recovered from the liquid-phase recovery line 70 at 512 g/Hr. Low boiling point components were also recovered at 496 g/Hr from the reaction middle portion 62 via the liquid-phase recovery line 75. Furthermore, from the reactor lower portion 64, a dibutyltin alkoxide-containing component was recovered at 603 g/Hr from the extraction line 76. Analysis of the liquid recovered from the extraction line 76 showed that, using dibutyltin oxide as a reference, the liquid contained a dibutyltin alkoxide consisting of a yield of about 47.5% dibutyl-di(butyloxy)tin and 52.4% of 1,1,3,3-tetrabutyl-1,3-di(butyloxy)-distannoxane. Tributyltin butoxide had a yield of 0.021%. Meanwhile, the liquid recovered from the liquid-phase recovery lines 70 and 75 was transparent and contained 2,200 ppm of moisture. The dehydration rate in the column reactor was 0.21 mol/Hr, which was greater than the value 0.00081 mol/Hr calculated from expression (16).

Example 17

Obtaining Dibutyltin Dialkoxide Using a Column Reactor

Dibutyltin alkoxide was produced in a column reactor 82 such as that illustrated in FIG. 7. A 50 mm inner diameter and 4,000 mm total length column reactor 82 made from SUS 316, which was furnished with a low boiling point component recovery line 86, a condenser 87, a low boiling point component storage tank 88, a back pressure valve 89, a vent line 90 and a liquid-phase recovery line 91 on a reactor upper portion 84, a supply line 77, a supply line 78 and a heat exchanger 79 on a reactor middle portion 83, and a circulation line 80 for circulating reaction solution that has accumulated at a reactor lower portion, a reboiler 81 and an extraction line 92 on a reactor lower portion 85, was packed with Mellapak 750Y (Sulzer Chemtech Ltd., Switzerland). The temperature of the reactor was adjusted using a heater set to 140° C.

A feed pump was used to start feeding the starting material 1,1,3,3-tetrabutyl-1,3-di(butyloxy)-distannoxane prepared in the same manner as in Example 12 from supply line 77 at 280 g/Hr and the reactant 1-butanol (manufactured by Wako Pure Chemical Industries Ltd., Japan, industrial product) from supply line 78 at 1,330 g/Hr. The holding time in the reactor was 6 minutes. Reaction solution which accumulated in the reactor lower portion was circulated at 6,000 g/Hr by the circulation line 80 and the reboiler 81 while heating at a temperature of about 140° C. The liquid temperature inside the reactor was 140° C., and the pressure of the back pressure valve 89 was adjusted to 0.096 MPa-G. Continuous supply was continued in this state for 10 hours, after which the system reached a steady state. Low boiling point components flowed from the reactor upper portion 84 and through the low boiling point component recovery line 86 for liquefaction at the condenser 87, and were thereby recovered from the liquid-phase recovery line 91 at 1,031 g/Hr. Furthermore, from the reactor lower portion 85, a dibutyltin alkoxide-containing component was recovered at 602 g/Hr from the extraction line 92. Analysis of the recovered liquid showed that, using dibutyltin oxide as a reference, the liquid contained a dibutyltin alkoxide consisting of a yield of about 47.0% dibutyl-di(butyloxy)tin and 52.9% of 1,1,3,3-tetrabutyl-1,3-di(butyloxy)-distannoxane. Tributyltin butoxide had a yield of 0.012%. Meanwhile, the liquid recovered from the liquid-phase recovery line 91 was transparent and contained 2,200 ppm of moisture. The dehydration rate in the column reactor was 0.21 mol/Hr, which was greater than the value 0.00037 mol/Hr calculated from expression (16).

Example 18

Obtaining Dibutyltin Dialkoxide Using a Column Reactor

Dibutyltin alkoxide was produced in a column reactor 99 such as that illustrated in FIG. 8. A 50 mm inner diameter and 4,000 mm total length column reactor 99 made from SUS 316, which was furnished with a low boiling point component recovery line 103, a condenser 104, a low boiling point component storage tank 105, a back pressure valve 106, a vent line 107, and a liquid-phase recovery line 108 on a reactor upper portion 101, a supply line 93, a supply line 94 and a heat exchanger 95 on a reactor middle portion 100, and an organic solvent supply line 96, a circulation line 97 for circulating accumulated reaction solution, a reboiler 98 and an extraction line 109 on a reactor lower portion 102, was packed with Mellapak 750Y (Sulzer Chemtech Ltd., Switzerland). The temperature of the reactor was adjusted using a heater set to 140° C.

A feed pump was used to start feeding the starting material 1,1,3,3-tetrabutyl-1,3-di(butyloxy)-distannoxane prepared in the same manner as in Example 12 from supply line 93 at 280 g/Hr and the reactant 1-butanol (manufactured by Wako Pure Chemical Industries Ltd., Japan, industrial product) from supply line 94 at 1,330 g/Hr. The holding time in the reactor was 6 minutes. A pump was used to supply hexane (manufactured by Wako Pure Chemical Industries Ltd., Japan, dehydration grade) at 300 g/Hr from the organic solvent supply line 96 to the reactor lower portion 102, wherein accumulated reaction solution was circulated at 6,000 g/Hr by the circulation line 97 and the reboiler 98 while heating at a temperature of about 140° C. The liquid temperature inside the reactor was 140° C., and the pressure of the back pressure valve 106 was adjusted to 0.12 MPa-G. Continuous supply was continued in this state for 10 hours, after which the system reached a steady state. Low boiling point components flowed from the reactor upper portion 101 and through the low boiling point component recovery line 103 for liquefaction at the condenser 104, and were thereby recovered from the liquid-phase recovery line 108 at 1,088 g/Hr. Furthermore, from the reactor lower portion 102, a dibutyltin alkoxide-containing component was recovered at 821 g/Hr from the extraction line 109. Analysis of the recovered liquid showed that using dibutyltin oxide as a reference, the liquid contained a dibutyltin alkoxide consisting of a yield of about 54.0% dibutyl-di(butyloxy)tin and 46.0% of 1,1,3,3-tetrabutyl-1,3-di(butyloxy)-distannoxane. Tributyltin butoxide had a yield of 0.013%. Meanwhile, the liquid recovered from the liquid-phase recovery line 108 was transparent and contained 2,500 ppm of moisture. The dehydration rate in the column reactor was 0.24 mol/Hr, which was greater than the value 0.00037 mol/Hr calculated from expression (16).

Example 19

Obtaining Dibutyltin Dialkoxide Using a Horizontal Thin-Film Distillation Apparatus Dibutyltin alkoxide was produced in a horizontal thin-film distillation apparatus 113 (manufactured by Nitinan Engineering Co., Ltd., Japan, PFD1) such as that illustrated in FIG. 9. A 50 mm inner diameter and 1,100 mm total length a horizontal thin-film distillation apparatus 113 made from SUS 316A was furnished with a supply line 110, a supply line 111, a heat exchanger 112, a low boiling point component recovery line 116, a condenser 117, a low boiling point component storage tank 118, a vent line 119, and a liquid-phase recovery line 120 on a reactor upper portion 114, and an extraction line 121 on a reactor lower portion 115. The temperature of the reactor was adjusted using a heater set to 120° C.

A feed pump was used to start feeding the starting material 1,1,3,3-tetrabutyl-1,3-di(butyloxy)-distannoxane prepared in the same manner as in Example 12 from supply line 110 at 4,600 g/Hr and the reactant 1-butanol (manufactured by Wako Pure Chemical Industries Ltd., Japan, industrial product) from alcohol supply line 111 at 22,000 g/Hr. The holding time in the reactor was 6 minutes. The liquid temperature inside the reactor was adjusted to 120° C. Continuous supply was continued in this state for 2 hours, after which the pressure in the system reached a steady state. Low boiling point components flowed through the low boiling point component recovery line 116 for liquefaction at the condenser 117, and were thereby recovered from the liquid-phase recovery line 120 at 18,000 g/Hr. Furthermore, from the reactor lower portion 115, a dibutyltin alkoxide-containing component was recovered at 8,600 g/Hr from the extraction line 121. Analysis of the recovered liquid showed that, using dibutyltin oxide as a reference, the liquid contained a dibutyltin alkoxide consisting of a yield of about 34.2% dibutyl-di(butyloxy)tin and 65.7% of 1,1,3,3-tetrabutyl-1,3-di(butyloxy)-distannoxane. Tributyltin butoxide had a yield of 0.015%. Meanwhile, the liquid recovered from the liquid-phase recovery line 120 was transparent and contained 2,000 ppm of moisture. The dehydration rate in the reactor was 2.5 mol/Hr, which was greater than the value 0.0061 mol/Hr calculated from expression (16).

Example 20

Step 1: (Preparation of the Starting Material 1,1,3,3-tetrabutyl-1,3-di(butyloxy)-distannoxane)

A 3,000 mL recovery flask was charged with 759 g (3.05 mol) of dibutyltin oxide (manufactured by Aldrich Chemical Co., U.S.A.) and 1,960 g (26.5 mol) of 1-butanol (manufactured by Wako Pure Chemical Industries Ltd., Japan), whereby the flask contained the resulting white slurry mixture. The flask was attached to an evaporator (manufactured by Shibata Scientific Technology Ltd., R-144) connected to a thermoregulator-equipped oil bath (manufactured by Masuda Corporation, Japan, OBH-24), a vacuum pump (manufactured by ULVAC Inc., Japan, G-50A), and a vacuum controller (manufactured by Okano Works Ltd., Japan, VC-10S). The evaporator purge valve outlet was connected to a nitrogen gas line flowing at atmospheric pressure. The evaporator purge valve was closed to thereby lower the pressure in the system. The purge valve was then gradually opened, and nitrogen was flowed into the system to return the system to atmospheric pressure. The oil bath temperature was set at 127° C. The flask was immersed in the oil bath, and rotation of the evaporator was started. Rotation was continued for about 40 minutes while stirring and heating under atmospheric pressure with the evaporator purge valve open, whereby the reaction solution came to the boil, to thereby start distillation of the low boiling point constituents. This state was maintained for 7 hours, after which the purge valve was closed, whereby the system internal pressure was slowly lowered. The remaining low boiling point constituents were distilled off when the system internal pressure was around 76 to 54 kPa. Once low boiling point constituents stopped being distilled off, the flask was removed from the oil bath. The reaction solution had tuned transparent. The distilled off liquid was 1,737 g, transparent and had separated into 2 layers. Analysis of the distilled off liquid showed that it contained about 27.6 g of water. The flask was then removed from the oil bath and the purge valve was slowly closed to return the system internal pressure to atmospheric pressure. The flask yielded 958 g of the reaction solution. Results of $^{119}$Sn, $^1$H and $^{13}$C-NMR analysis showed that, using dibutyltin oxide as a reference, the generated product 1,1,3,3-tetrabutyl-1,3-di(butyloxy)-distannoxane was obtained in a 99% yield. The same procedures were repeated 6 times, whereby a total of 5,748 g of 1,1,3,3-tetrabutyl-1,3-di(butyloxy)-distannoxane was obtained.

Step 2: (Obtaining Dibutyltin Dialkoxide Using a Column Reactor)

Dibutyltin alkoxide was produced in a column reactor such as that illustrated in FIG. 4. A 50 mm inner diameter and 4,000 mm total length column reactor 31 made from SUS 316, which was furnished with a supply line 26, a supply line 27, a heat exchanger 28, a low boiling point component recovery line 34, a condenser 35, a gas-liquid separator 36, a back pressure valve 37, a vent line 38, and a liquid-phase recovery line 39 on a reactor upper portion 32, and a gas supply line 29, a heat exchanger 30 and an extraction line 40 on a reactor lower portion 33, was packed with Goodroll Type A (Tokyo Tokushu Kanaami K.K., Japan). The temperature of the reactor was adjusted using a heater set to 140° C. From the gas supply line 29, 1-butanol (manufactured by Wako Pure Chemical Industries Ltd., Japan, industrial product) was fed at 399 g/Hr and carbon dioxide was fed at 3 NL/Hr. All of the 1-butanol was vaporized by the heat exchanger 30 and fed to the reactor lower portion 33. A feed pump was used to start feeding the starting material 1,1,3,3-tetrabutyl-1,3-di(butyloxy)-distannoxane from supply line 26 at 210 g/Hr and the reaction solution 1-butanol (manufactured by Wako Pure Chemical Industries Ltd., Japan, industrial product) from supply line 27 at 951 g/Hr. The holding time in the reactor was 30 minutes.

Step 3: (Obtaining a Carbonic Ester from Dialkyltin Alkoxide)

A feed pump was used to feed the reaction solution obtained in Step 2 at 807 g/Hr into thin film distillation equipment (manufactured by Kobelco Eco-Solutions Co., Ltd., Japan) set to 80° C. and about 6.5 kPa to remove volatile components. The non-volatile components were cooled and recovered, whereby 241 g/Hr were fed into a 990 mL autoclave (manufactured by Toyo Koatsu Co., Ltd., Japan). Once the secondary pressure of a carbon dioxide cylinder connected to the autoclave via SUS tubing and a valve had been set to 4 MPa, the valve was opened, whereby carbon dioxide was fed into the autoclave at 28 g/Hr using a mass flow controller (manufactured by Oval Corporation, Japan). The temperature was raised to 120° C. The holding time in the autoclave was about 1 hour. The liquid that had reacted with the carbon dioxide was transferred to a gaseous carbon dioxide removal tank and the pressure was returned to atmospheric pressure. A feed pump was then used to feed the reaction solution at 267 g/Hr into thin film distillation equipment (manufactured by Kobelco Eco-Solutions Co., Ltd., Japan) set to 130° C. and about 1.3 kPa to remove volatile components, including dibutyl carbonate, and the non-volatile components were cooled and recovered. This dibutyl carbonate-containing volatile component was fed at 202 g/Hr into the middle stage of a 50 mm inner diameter 2,000 mm column length continuous multistage distillation column that was packed with Dickson packing (6 mm inner diameter), whereby distillation separation was carried out. The cooled liquid was a mixture of 1-butanol and dibutyl carbonate, 98% of which was dibutyl carbonate. No tributyltin butyloxy was detected in this mixed solution, nor was chlorine detected from the results of chlorine analysis. However, $^{119}$Sn, $^1$H and $^{13}$C-NMR analysis of the non-volatile component did show that 1,1,3,3-tetrabutyl-1,3-di(butyloxy)-distannoxane was present, while dibutyl-di(butyloxy)tin was not.

The 1,1,3,3-tetrabutyl-1,3-di(butyloxy)-distannoxane contained in the non-volatile component recovered in Step 3 was returned using a feed pump to the column reactor 31, and Step 2 was repeated.

The liquid temperature inside the Step 2 reactor was adjusted to 140° C., and the pressure of the back pressure valve 37 was adjusted to 0.096 MPa-G. Continuous supply was continued in this state for 10 hours, after which the system reached a steady state. Low boiling point components flowed from the reactor upper portion 32 and through the low boiling point component recovery line 34 for liquefaction at the condenser 35, and were thereby recovered from the liquid-phase recovery line 39 at 753 g/Hr. Furthermore, from the reactor lower portion 33, a dibutyltin alkoxide-containing component was recovered at 807 g/Hr from the extraction line 40. Analysis of the recovered liquid showed that using dibutyltin oxide as a reference, the liquid contained a dibutyltin alkoxide consisting of a yield of 41.3% dibutyl-di(butyloxy) tin and 58.7% of 1,1,3,3-tetrabutyl-1,3-di(butyloxy)-distannoxane. Tributyltin butoxide had a yield of 0.04%. Meanwhile, the liquid recovered from the liquid-phase recovery line 39 was transparent and contained 2,500 ppm of moisture. The dehydration rate in the column reactor was 0.144 mol/Hr, which was greater than the value 0.0015 mol/Hr calculated from expression (16). In addition, the yield of the dibutyl carbonate obtained from Step 3 was about 30 g/Hr. The obtained dibutyl carbonate did not contain any chlorine compounds or tributyl compounds.

Example 21

Production of Diphenyl Carbonate from Dibutyl Carbonate Obtained Using the Production Process of Example 20

Catalyst Preparation

Phenol (80 g) and 32 g of lead monoxide were heated for 12 hours at 180° C., and the generated water was distilled off along with the phenol, to thereby prepare a catalyst A.

Production of Butylphenyl Carbonate

Butylphenyl carbonate was produced using the dibutyl carbonate obtained in Example 20 by using an apparatus such as that illustrated in FIG. 10. The reaction was carried out by using a feed pump to continuously feed a mixed solution of dibutyl carbonate, phenol and catalyst A (adjusted so that the weight ratio in the mixture between dibutyl carbonate and phenol was 65/35, and the lead concentration was about 1% by weight) from a supply line 122 via a heat exchanger 123 at 270 g/Hr to the middle stage of a 50 mm inner diameter 2,000 mm column length continuous multistage distillation column 124 that had its sieve trays of the plates 40 packed. The heat required for the reaction and distillation was fed through circulatory heating of the column lower portion via a circulation line 131 and a reboiler 130. The liquid temperature of the continuous multistage distillation column 124 column lower portion was adjusted to 231° C., and the pressure at the column top was adjusted to about 200 kPa by means of a back pressure valve 128. The reflux ratio was set at about 2. The low boiling point components distilled off from the column top of the continuous multistage distillation column 124 flowed through the low boiling point component recovery line 125 for condensing at the condenser 126, then flowed through the low boiling point component storage tank 127, and were thereby continuously extracted at about 67 g/Hr from the line 129. From the column lower portion, high boiling point components flowed through the high boiling point component line 131, and were thereby continuously extracted at the extraction line 132 at about 203 g/Hr. The composition of the liquid extracted from the liquid-phase recovery line 129 was about 27% by weight of 1-butanol, about 72% by weight of phenol and about 1% by weight of dibutyl carbonate. The composition of the liquid distilled off from the extraction line 132 was 330 ppm of 1-butanol, about 11% by weight of phenol, about 65% by weight of dibutyl carbonate, about 21% by weight of butylphenyl carbonate, and about 1% by weight of diphenyl carbonate, and had a Pb concentration of about 1% by weight.

Production of Diphenyl Carbonate from a Disproportionate Reaction of Butylphenyl Carbonate Diphenyl carbonate was produced using an apparatus such as that illustrated in FIG. 11. The reaction was carried out by using a feed pump to continuously feed butylphenyl carbonate from a supply line 133 via a preheater 134 at about 203 g/Hr to the middle stage of a 5 cm diameter 2 m column length continuous multistage distillation column 135 that has its sieve trays of the plates 40 packed. The heat required for the reaction and distillation was fed through circulatory heating of the column lower portion via a circulation line 142 and a reboiler 141. The liquid temperature of the continuous multistage distillation column 135 column lower portion was adjusted to 237° C., and the pressure at the column top was adjusted to about 27 kPa by means of a pressure control valve 139. The reflux ratio was set at about 2. Low boiling point components distilled off from the column top of the continuous multistage distillation column 135 flowed through the low boiling point component recovery line 136 for condensing at the condenser 137, then flowed through the low boiling point component storage tank 138 and were continuously extracted at about 172 g/Hr from the liquid-phase recovery line 140. From the column lower portion, high boiling point components were continuously distilled off at about 31 g/Hr via the extraction line 143. The composition of the liquid distilled off from the liquid-phase recovery line 140 was 390 ppm of 1-butanol, about 13% by weight of phenol, about 86% by weight of dibutyl carbonate and about 1% by weight of butylphenyl carbonate. The composition of the liquid extracted from the extraction line 143 was 500 ppm of dibutyl carbonate, about 26% by weight of butylphenol carbonate, and about 65% by weight of diphenyl carbonate, and had a Pb concentration of about 8% by weight.

Next, the diphenyl carbonate was purified using an apparatus such as that illustrated in FIG. 12. Liquid was continuously fed at 315 g/Hr from an extraction line 143 via a supply line 144 and a heat exchanger 145 to the middle stage of a 5 cm diameter 2 m column length continuous multistage distillation column 146 packed with Dickson packing (6 mm inner diameter), whereby distillation separation was carried out. The heat required for the distillation separation was fed through circulatory heating of the column lower portion via a circulation line 153 and a reboiler 152. The liquid temperature of the continuous multistage distillation column 146 column lower portion was adjusted to 210° C., and the pressure at the column top was adjusted to about 1.5 kPa by means of a pressure control valve 150. The reflux ratio was set at about 1. Low boiling point components distilled off from the column top of the continuous multistage distillation column 146 flowed through a low boiling point component recovery line 147, condensed at the condenser 148, then flowed through the low boiling point component storage tank 149 and were continuously extracted at about 288 g/Hr from the liquid-phase recovery line 151. From the column bottom, the low boiling point components were continuously extracted out of the system at about 27 g/Hr from the extraction line 154. The composition of the liquid extracted from the liquid-phase recovery line 151 was about 200 ppm of dibutyl carbonate, about 29% by weight of butylphenyl carbonate and about 71% by weight of diphenyl carbonate. The liquid continuously extracted from the liquid-phase recovery line 155 was fed at 288 g/Hr via a transfer line 155 and a heat exchanger 156 to the middle stage of a 5 cm diameter 4 m column length continuous multistage distillation column 157 packed with Dickson packing (6 mm inner diameter), whereby distillation separation was carried out. The heat required for the distillation separation was fed through circulatory heating of the column lower portion via a circulation line 164 and a reboiler 163. The liquid temperature of the continuous multistage distillation column 157 column lower portion was adjusted to 198° C., and the pressure at the column top was adjusted to about 6 kPa by means of a pressure control valve 161. The reflux ratio was set at about 6. Low boiling point components distilled off from the column top of the continuous multistage distillation column 157 flowed through the low boiling point component recovery line 158, were condensed at the condenser 159, then flowed through the low boiling point component storage tank 160 and were continuously extracted at about 90 g/Hr from the liquid-phase recovery line 162. From the column bottom, the low boiling point components were continuously extracted out of the system at about 198 g/Hr from the extraction line 165. The composition of the liquid extracted from the liquid-phase recovery line 162 was about 700 ppm of dibutyl carbonate, about 93% by weight of butylphenyl carbonate and about 7% by weight of diphenyl carbonate. The composition of the liquid extracted from the extraction line 165 comprised less than the measurable limits of butylphenyl carbonate and 99% by weight of diphenyl carbonate. The chlorine concentration in the reaction solution was below measurable limits.

Example 22

Production of Hexamethylene Diisocyanate from the Diphenyl Carbonate Obtained from Example 21

A 500 mL flask equipped with a stirring apparatus, a thermometer and a dropping funnel was charged with 161 g (0.75 mol) of the diphenyl carbonate obtained in Example 21 and 142 g (1.5 mol) of phenol (manufactured by Aldrich Chemical Co., U.S.A., pre-distilled). After purging with dry nitrogen, the flask was immersed in a 50° C. water bath, and stirring was started. Once the solid content in the flask was confirmed to have dissolved, the water bath temperature was set to 45° C. The dropping funnel contained 35 g (0.3 mol) of 1,6-hexamethylene diamine (manufactured by Aldrich Chemical Co., pre-distilled) kept at a temperature of between 45 to 50° C. Dropping was started into the flask from this dropping funnel. While adjusting the dropping rate so that the liquid temperature in the flask remained between 50 to 60° C., dropping was carried out over about 20 minutes. Once dropping was finished, the water bath set temperature was adjusted so that the liquid temperature in the flask was 50° C., and stirring was continued for 1 hour. The results of high performance liquid chromatography and gel permeation chromatography showed that the 1,6-hexamethylene diamine rate of reaction was 100%, whereby 1,6-hexamethylene phenyl dicarbamate was generated with a yield of 99.6% and a selectivity of 99.6%. Urea compounds had a yield of about 0.4%.

The reaction solution produced in this manner was fed via a preheater into the middle stage of a 2 inch diameter 4 m column length continuous multistage distillation column packed with Dickson packing (6 mm inner diameter), wherein excess phenol was extracted in gaseous form from the distillation column upper portion, and the high boiling point components were continuously extracted from the distillation column lower portion. The column lower portion was subjected to circulatory heating at 130° C. by a reboiler, and the column top portion pressure was adjusted to about 20 kPa.

Thermal decomposition was carried out by feeding the solution extracted from the column bottom via a transfer line and a pump into an area about 1 m from the bottom of a 2 inch diameter 4 m column length continuous multistage distillation column packed with Dickson packing (6 mm inner diameter). The column lower portion was subjected to circulatory heating at 220° C. by a reboiler, and the column top portion pressure was adjusted to about 2.6 kPa. A hexamethylene diisocyanate-containing component was extracted in gaseous form from an area about 2 m from the upper portion of the column, and phenol was extracted in gaseous form from the upper portion of the column. The hexamethylene diisocyanate-containing component was fed into the middle stage of a 2 inch diameter 4 m column length continuous multistage distillation column packed with Dickson packing (6 mm inner diameter), whereby the hexamethylene diisocyanate was purified. The column lower portion was subjected to circulatory heating at 120° C. by a reboiler, and the column top portion pressure was adjusted to about 0.13 kPa. The components extracted from the column top portion were obtained having a 99.9% hexamethylene diisocyanate purity. In addition, the components extracted from the column bottom had a main component of diphenyl carbonate.

Comparative Example 8

Obtaining Hexamethylene Diisocyanate from a Chlorine Compound-Containing Diphenyl Carbonate A 500 mL flask equipped with a stirring apparatus, a thermometer and a dropping funnel was charged with 161 g (0.75 mol) of diphenyl carbonate (manufactured by Bayer, Germany, hydrolyzable chlorine compound content of 15 ppm) and 142 g (1.5 mol) of phenol (manufactured by Aldrich Chemical Co., U.S.A., pre-distilled). After purging with dry nitrogen, the flask was immersed in a 50° C. water bath, and stirring was started.

Once the solid content in the flask was confirmed to have dissolved, the water bath temperature was set to 45° C. The dropping funnel contained 35 g (0.3 mol) of 1,6-hexamethylene diamine (manufactured by Aldrich Chemical Co., pre-distilled) kept at a temperature of between 45 to 50° C. Dropping was started into the flask from this dropping funnel. While adjusting the dropping rate so that the liquid temperature in the flask remained between 50 to 60° C., dropping was carried out over about 20 minutes. Once the dropping was finished, the water bath set temperature was adjusted that the liquid temperature in the flask was 50° C., and stirring was continued for 1 hour.

The results of high performance liquid chromatography and gel permeation chromatography showed that the 1,6-hexamethylene diamine rate of reaction was 99%, whereby 1,6-hexamethylene phenyl dicarbamate was generated with a yield of 99% and a selectivity of 99.6%. Urea compounds had a yield of about 0.5%.

The reaction solution produced in this manner was fed via a waste heat boiler into the middle stage of a 2 inch diameter 4 m column length continuous multistage distillation column packed with Dickson packing (6 mm inner diameter), wherein excess phenol was extracted in gaseous form from the distillation column upper portion, and high boiling point components were continuously extracted from the distillation column lower portion. The column lower portion was subjected to circulatory heating at 130° C. by a reboiler, and the column top portion pressure was adjusted to about 20 kPa. Thermal decomposition was carried out by feeding the liquid extracted from the column bottom via a transfer line and a pump into an area about 1 m from the bottom of a 2 inch diameter 4 m column length continuous multistage distillation column packed with Dickson packing (6 mm inner diameter). The column lower portion was subjected to circulatory heating at 220° C. by a reboiler, and the column top portion pressure was adjusted to about 2.6 kPa.

A hexamethylene diisocyanate-containing component was extracted in gaseous form from an area about 2 m from the upper portion of the column, and phenol was extracted in gaseous form from the upper portion of the column. The hexamethylene diisocyanate-containing component was fed into the middle stage of a 2 inch diameter 4 m column length continuous multistage distillation column packed with Dickson packing (6 mm inner diameter), whereby the hexamethylene diisocyanate was purified. The column lower portion was subjected to circulatory heating at 120° C. by a reboiler, and the column top portion pressure was adjusted to about 130 Pa.

The components extracted from the column top portion were obtained having a 99.3% hexamethylene diisocyanate purity. In addition, the components distilled off from the column bottom had a main component of diphenyl carbonate. The obtained hexamethylene diisocyanate contained 5 ppm of a hydrolyzable chlorine compound.

Example 23

Production of Polycarbonate from the Diphenyl Carbonate Obtained from Example 21

A vacuum reactor equipped with a stirring apparatus was charged with 23.5 g of the diphenyl carbonate (NMR analysis did not detect any impurities, including methyl groups (excluding methyl groups on alkyl group ends), and 22.8 g of bisphenol A. While purging with nitrogen gas, the resulting mixture was polymerized at 8 kPa for 30 minutes and at 4 kPa for 90 minutes, after which the temperature was raised to 270° C. and polymerization was carried out at 0.07 kPa for 1 hour. The obtained aromatic polycarbonate was colorless and transparent, of good quality, and had a number average molecular weight of 10,500.

Comparative Example 9

Obtaining Polycarbonate from a Chlorine Compound-Containing Diphenyl Carbonate

A vacuum reactor equipped with a stirring apparatus was charged with 23.5 g of diphenyl carbonate (manufactured by Bayer, Germany, chlorine compound content of 15 ppm), and 22.8 g of bisphenol A. While purging with nitrogen gas, the resulting mixture was polymerized at 8 kPa for 30 minutes and at 4 kPa for 90 minutes, after which the temperature was raised to 270° C. and polymerization was carried out at 0.07 kPa for 1 hour. A polymer was not obtained. A non-completely reacted product which contained an oligomer having a number average molecular weight of 800 or less was obtained.

Comparative Example 10

Synthesis of a Carbonic Ester from a Dibutyltin Alkoxide Containing a Large Quantity of a Tributyltin Compound A high-pressure vessel was charged with 120 g of the dibutyltin(2-ethyl-hexyloxide) (tributyltin(2-ethyl-hexyloxide content of 29 mol %)) obtained in Comparative Example 5 in the same manner as in Comparative Example 6. Heating and stirring were also carried out in the same manner. After the mixed solution temperature had been lowered and carbon dioxide gas removed in the same manner, 100 g of mixed solution were collected in a 200 mL three-necked flask equipped with a three-way stopcock. Next, the flask was connected to a connection pipe provided with a branch pipe, a thermometer, a Liebig condenser, a low-pressure connection pipe and two distillate recovery vessels. The flask was immersed in an oil bath to raise the mixed solution temperature to 130° C. Using a vacuum pump and a vacuum controller, the pressure was gradually lowered to 0.13 kPa, whereby 18 g of a fraction having a steam temperature of about 125° C. was obtained. The results of GC-FID analysis for the fraction showed a content of 55% by weight of di-2-ethylhexyl carbonate. In addition, it was confirmed from $^{119}$Sn-NMR analysis that about 44% by weight of a tributyltin compound was mixed in the carbonic acid ester.

Comparative Example 11

Catalyst Preparation

Phenol (40 g) and 8 g of lead monoxide were heated for 10 hours at 180° C., and the generated water was distilled off along with the phenol, to thereby prepare a catalyst A.

Production of Diphenyl Carbonate

A 1,000 mL autoclave (manufactured by Toyo Koatsu Co., Ltd., Japan) was charged with 110 g of (3-methyl-1-butyl) carbonate obtained in the same manner as that in Comparative Example 7, 490 g of pre-distilled and purified phenol (manufactured by Aldrich Chemical Co., U.S.A., and catalyst A (in an amount such that the lead concentration was 0.4% by weight of the contents in the autoclave), and the cover was shut.

The autoclave interior was purged with nitrogen gas, after which the valve was closed and stirring was started. The temperature inside the autoclave was raised to 230° C. Nitrogen was introduced at the lower portion of the autoclave at 50 mL/min. The autoclave upper portion valve was operated so that the total pressure in the autoclave was in a range of between 100 to 200 kPa, and low boiling point constituents were distilled off for 4 hours. After 4 hours, the introduction of nitrogen was stopped, and the autoclave was allowed to cool.

Analysis of the contents showed that about 0.28 mol of di(3-methyl-1-butyl), 0.21 mol of 3-methyl-1-butyl(phenyl) carbonate, and 0.026 mol of diphenyl carbonate had been obtained.

The reaction solution was transferred to a 1,000 mL 3-necked flask equipped with a condenser, which was connected to a vacuum controller and a vacuum pump, and a Dean-Stark trap. A stirrer was added for stirring. The flask was immersed in an oil bath set to 150° C., and stirring was started. Pressure was gradually lowered to about 100 kPa. Unreacted phenol and (3-methyl-1-butyl) carbonate were distilled off in this state, to thereby yield a reaction solution consisting mainly of 3-methyl-1-butyl(phenyl) carbonate and diphenyl carbonate.

Next, the vacuum level was adjusted to 50 kPa, and stirring and the reaction were continued with the oil bath temperature at 220° C. The reaction was continued for 6 hours while distilling off di(3-methyl-1-butyl) carbonate, and then stopped. Analysis of the reaction solution showed that about 0.26 mol (56 g) of diphenyl carbonate had been generated.

The flask was then connected to a glass pipe having about a 25 mm inner diameter and a 500 mm column length filled with Helipack No. 2, a connection pipe provided with a branch pipe, a thermometer, a Liebig condenser, a low-pressure connection pipe and two distillate recovery vessels. The flask was immersed in an oil bath to raise the mixed solution temperature to 185° C. Using a vacuum pump and a vacuum controller, the pressure was then gradually lowered to distill off low boiling point components, after which the pressure in the system was lowered to about 2 kPa. About 50 g of a fraction having a steam temperature of 175° C. was obtained. The results of GC-FID analysis for the fraction showed a diphenyl carbonate content of 98% by weight. In addition, it was confirmed from $^{119}$Sn-NMR analysis that 1.5% by weight of a tributyltin compound was contained in the diphenyl carbonate.

Comparative Example 12

Obtaining Hexamethylene Diisocyanate from Diphenyl Carbonate Comprising Tributyltin Compound-Containing Impurities A 500 mL flask equipped with a stirring apparatus, a thermometer and a dropping funnel was charged with 160 g (0.75 mol) of diphenyl carbonate obtained in the same manner as that in Comparative Example 11, and 142 g (1.5 mol) of phenol (manufactured by Aldrich Chemical Co., U.S.A., pre-distilled). After purging with dry nitrogen, the flask was immersed in a 50° C. water bath, and stirring was started.

Once the solid content in the flask was confirmed to have dissolved, the water bath temperature was set to 45° C. The dropping funnel contained 35 g (0.3 mol) of 1,6-hexamethylene diamine (manufactured by Aldrich Chemical Co., pre-distilled) kept at a temperature of between 45 to 50° C. Dropping was started into the flask from this dropping funnel. While adjusting the dropping rate so that the liquid temperature in the flask remained between 50 to 60° C., dropping was carried out over about 20 minutes. Once the dropping was finished, the water bath set temperature was adjusted that the solution temperature in the flask was 50° C., and stirring was continued for 1 hour.

The results of high performance liquid chromatography and gel permeation chromatography showed that the 1,6-hexamethylene diamine rate of reaction was 99%, whereby 1,6-hexamethylene phenyl dicarbamate was generated with a yield of 99% and a selectivity of 99.6%. Urea compounds had a yield of about 0.5%.

The reaction solution produced in the above manner was fed via a waste heat boiler into the middle stage of a 2 inch diameter 4 m column length continuous multistage distillation column packed with Dickson packing (6 mm inner diameter), wherein excess phenol was extracted in gaseous form from the distillation column upper portion, and high boiling point components were continuously extracted from the distillation column lower portion. The column lower portion was subjected to circulatory heating at 130° C. by a reboiler, and the column top portion pressure was adjusted to about 20 kPa. Thermal decomposition was carried out by feeding the solution distilled off from the column bottom via a transfer line and a pump into an area about 1 m from the bottom of a 2 inch diameter 4 m column length continuous multistage distillation column packed with Dickson packing (6 mm inner diameter). The column lower portion was subjected to circulatory heating at 220° C. by a reboiler, and the column top portion pressure was adjusted to about 2.6 kPa.

A hexamethylene diisocyanate-containing component was extracted in gaseous form from an area about 2 m from the upper portion of the column, and phenol was extracted in gaseous form from the upper portion of the column. The hexamethylene diisocyanate-containing component was fed into the middle stage of a 2 inch diameter 4 m column length continuous multistage distillation column packed with Dickson packing (6 mm inner diameter), whereby the hexamethylene diisocyanate was purified. The column lower portion was subjected to circulatory heating at 120° C. by a reboiler, and the column top portion pressure was adjusted to about 130 Pa.

The component extracted from the column top portion was colored brown, and obtained having a 95% hexamethylene diisocyanate purity. In addition, the component extracted from the column bottom had a main component of diphenyl carbonate.

Comparative Example 13

Obtaining Polycarbonate from Diphenyl Carbonate Comprising Tributyltin Compound-Containing Impurities A vacuum reactor equipped with a stirring apparatus was charged with 24.5 g of diphenyl carbonate (tributyltin compound content of about 1.5% by weight) obtained in the same manner as that in Comparative Example 11, and 23.2 g of bisphenol A. While purging with nitrogen gas, the resulting mixture was polymerized at 8 kPa for 30 minutes and at 4 kPa for 90 minutes, after which the temperature was raised to 270° C. and polymerization was carried out at 0.07 kPa for 1 hour. The obtained aromatic polycarbonate was brown and had a number average molecular weight of 9,000.

Comparative Example 14

Production of Diphenyl Carbonate from Dimethyl Carbonate

Catalyst Preparation

Titanium tetrabutoxide (340 g (1 mol), manufactured by Tokyo Kasei Kogyo Co., Ltd., Japan) and 1,882 g (20 mol) of phenol were heated for 6 hours at 180° C., and the generated 1-butanol was distilled off along with the phenol, to thereby prepare a catalyst B.

Production of Diphenyl Carbonate

Diphenyl carbonate was produced by using an apparatus such as that illustrated in FIG. 13. The reaction was carried out by continuously feeding in liquid form a mixed solution of dimethyl carbonate, phenol and methylphenyl carbonate at 312 g/Hr from a supply line 166 via a heat exchanger 167 and a supply line 168 to the top 173 of a 50 mm inner diameter 2,000 mm column length continuous multistage distillation column 172 that was equipped with the sieve trays of plates 40. The respective components of the above-described mixture were employed such that the composition of the liquid in the supply line 168 during operation was 50.1% by weight of dimethyl carbonate, 44.6% by weight of phenol, and 5.0% by weight of methylphenyl carbonate. At the bottom 174 of the continuous multistage distillation column, dimethyl carbonate was introduced from the gas supply line 169 into the heat exchanger 170, whereby dimethyl carbonate that had been changed into gas form was fed at 550 g/Hr via the gas supply line 171. Catalyst B was fed from the catalyst introduction line 213 in an amount such that the Ti concentration in the transfer line 178 was 0.046% by weight. The temperature of the continuous multistage distillation column 172 column bottom was 203° C., and the pressure at the column top was 0.65 MPa-G. Gas distilled off from the column top 173 flowed through the low boiling point component recovery line 175 for liquefaction at the condenser 176, and was then extracted at 551 g/Hr from the liquid-phase recovery line 177. Reaction mixture extracted from the column bottom 174 at 311 g/Hr was introduced into the evaporator 179 via a transfer line 178. Here, a concentrate was formed containing the catalyst and an aromatic carbonic ester. A part of this concentrate was circulated to the evaporator 179 from the transfer line 180 and the circulation line 181 via the reboiler 182 and the circulation line 183. The rest of the concentrate was again fed to the multistage distillation column 172 from the evaporator 179 via the transfer line 180, the transfer line 184 and the supply line 166 at 10 g/Hr. A part of the concentrate formed at the evaporator 179 was extracted out of the system from the extraction line 185 at 0.5 g/Hr. Catalyst B was fed from the catalyst introduction line 213 so that the Ti concentration in a transfer line 178 was maintained at 0.046% by weight. Meanwhile, distillate from the evaporator 179 flowed through the low boiling point component recovery line 186 for liquefaction at the condenser 187. The resulting liquid flowed through the transfer line 188 and the transfer line 189 for reaction in the multistage distillation column 193 consisting of a 50 mm inner diameter and 1,000 mm column length plate column that was equipped with the sieve plates of plates 20. The composition of the liquid in the transfer line 189 was 42.1% by weight of dimethyl carbonate, 24.5% by weight of phenol, 28.1% by weight of methylphenyl carbonate and 4.5% by weight of diphenyl carbonate. The catalyst was fed from a catalyst introduction line 212 such that the Ti concentration in a transfer line 201 was 0.046% by weight. The temperature of the continuous multistage distillation column 193 column bottom was 198° C., and the pressure at the column top was 38 kPa. Gas distilled off from the column top 194 flowed through the low boiling point component recovery line 196 for liquefaction at the condenser 197. A part of the resulting concentrate was returned to the column top 194 from the transfer line 199. The rest of the concentrate was recirculated to the multistage distillation column 173 from the transfer line 198 and the transfer line 200 via the heat exchanger 167 and the supply line 168. After this recirculation operation was started, phenol was newly supplied from the supply line 166 so that the composition in the supply line 168 was the same. A part of the reaction mixture of the multistage distillation column bottom 195 was recirculated to the column bottom 195 from the circulation line 190 via a reboiler 191 and a circulation line 192. The rest of the reaction mixture was fed to the evaporator 202 from the transfer line 201 at 690 g/Hr. At the evaporator 202, a concentrate was formed containing the catalyst and an aromatic carbonic ester. A part of this concentrate was circulated to the evaporator 202 from the transfer line 203 and the circulation line 204 via the reboiler 205 and the circulation line 206. The rest of the concentrate was again fed to the multistage distillation column 193 from the evaporator 202 via the transfer line 203, the transfer line 207 and the transfer line 189 at 20 g/Hr. A part of the vapor concentrate formed at the evaporator 202 was extracted out of the system from an extraction line 208 at 1 g/Hr. Catalyst B was fed from the catalyst introduction line 212 so that the Ti concentration in the transfer line 201 was maintained at 0.046% by weight.

The gas distilled off from the evaporator 202 was extracted at 682 g/Hr from the liquid-phase recovery line 211 via the low boiling point constituent recovery line 209 and the condenser 210. The recovered liquid composition was 98% diphenyl carbonate. $^1$H-NMR analysis showed that the methyl group impurities were 90 ppm.

Comparative Example 15

Obtaining Hexamethylene Diisocyanate from Diphenyl Carbonate Containing Methyl Group Impurities A 500 mL flask equipped with a stirring apparatus, a thermometer and a dropping funnel was charged with 161 g (0.75 mol) of the diphenyl carbonate obtained in Comparative Example 14 (methylphenyl carbonate content of 90 ppm) and 142 g (1.5 mol) of phenol (manufactured by Aldrich Chemical Co., U.S.A., pre-distilled). After purging with dry nitrogen, the flask was immersed in a 50° C. water bath, and stirring was started.

Once the solid content in the flask was confirmed to have dissolved, the water bath temperature was set to 45° C. The dropping funnel contained 35 g (0.3 mol) of 1,6-hexamethylene diamine (manufactured by Aldrich Chemical Co., pre-distilled) kept at a temperature of between 45 to 50° C. Dropping was started into the flask from this dropping funnel. While adjusting the dropping rate so that the liquid temperature in the flask remained between 50 to 60° C., dropping was carried out over about 20 minutes. Once dropping was finished, the water bath set temperature was adjusted so that the liquid temperature in the flask was 50° C., and stirring was continued for 1 hour.

The results of high performance liquid chromatography and gel permeation chromatography showed that the 1,6-hexamethylene diamine rate of reaction was 99%, whereby 1,6-hexamethylene phenyl dicarbamate was generated with a yield of 99% and a selectivity of 99.6%. Urea compounds had a yield of about 0.5%.

The reaction solution produced in this manner was fed via a waste heat boiler into the middle stage of a 2 inch diameter 4 m column length continuous multistage distillation column packed with Dickson packing (6 mm inner diameter), wherein excess phenol was extracted in gaseous form from the distillation column upper portion, and high boiling point components were continuously extracted from the distillation column lower portion. The column lower portion was subjected to circulatory heating at 130° C. by a reboiler, and the column top portion pressure was adjusted to about 20 kPa. Thermal decomposition was carried out by feeding the liquid extracted from the column bottom via a transfer line and a pump into an area about 1 m from the bottom of a 2 inch diameter 4 m column length continuous multistage distillation column packed with Dickson packing (6 mm inner diameter). The column lower portion was subjected to circulatory heating at 220° C. by a reboiler, and the column top portion pressure was adjusted to about 2.6 kPa.

A hexamethylene diisocyanate-containing component was extracted in gaseous form from an area about 2 m from the upper portion of the column, and phenol was extracted in gaseous form from the upper portion of the column. The hexamethylene diisocyanate-containing component was fed into the middle stage of a 2 inch diameter 4 m column length continuous multistage distillation column packed with Dickson packing (6 mm inner diameter), whereby the hexamethylene diisocyanate was purified. The column lower portion was subjected to circulatory heating at 120° C. by a reboiler, and the column top portion pressure was adjusted to about 130 Pa.

The component extracted from the column top portion was colored brown, and obtained having a 98% hexamethylene diisocyanate purity. In addition, the component extracted from the column bottom had a main component of diphenyl carbonate.

Comparative Example 16

Obtaining Polycarbonate from Diphenyl Carbonate Containing Methyl Group Impurities A vacuum reactor equipped with a stirring apparatus was charged with 23.5 g of the diphenyl carbonate (methylphenyl carbonate content of 90 ppm), and 22.8 g of bisphenol A. While purging with nitrogen gas, the resulting mixture was polymerized at 8 kPa for 30 minutes and at 4 kPa for 90 minutes, after which the temperature was raised to 270° C. and polymerization was carried out at 0.07 kPa for 1 hour. The obtained aromatic polycarbonate was colorless and transparent, of good quality, and had a number average molecular weight of 9,500.

Comparative Example 17

Obtaining Dibutyltin Dialkoxide Using a Horizontal Thin-Film Distillation Apparatus Dibutyltin alkoxide was produced in a horizontal thin-film distillation apparatus (manufactured by Nitinan Engineering Co., Ltd., Japan, PFD1) such as that illustrated in FIG. 9. A 50 mm inner diameter and 1,100 mm total length horizontal thin-film distillation apparatus 113 made from SUS 316 was furnished with a tin alkoxide supply line 110, an alcohol supply line 111, a heat exchanger 112, a low boiling point component recovery line 116, a condenser 117, a low boiling point component storage tank 118, a vent line 119, and a liquid-phase recovery line 120 on a reactor upper portion 114, and a generated product extraction line 121 on a reactor lower portion 115. The temperature of the reactor was adjusted using a heater set to 120° C., and the internal pressure was adjusted to 54 kPa using a vacuum pump and a vacuum controller.

A feed pump was used to start feeding the starting material 1,1,3,3-tetrabutyl-1,3-di(butyloxy)-distannoxane prepared in the same manner as in Example 12 from supply line 110 at 4,600 g/Hr and the reactant 1-butanol (manufactured by Wako Pure Chemical Industries Ltd., Japan, dehydrated grade, water content 50 ppm) from alcohol supply line 111 at 22,000 g/Hr. The holding time in the reactor was 10 minutes. The liquid temperature inside the reactor was adjusted to 100° C. Continuous supply was continued in this state for 1 hour, after which the pressure in the system reached a steady state. Low boiling point components were recovered from the reactor upper portion 114 at 21,000 g/Hr. Furthermore, a dibutyltin alkoxide-containing component was recovered from the reactor lower portion 115 at 5,600 g/Hr. Analysis of the liquid recovered from the extraction line 121 showed that the liquid did not contain any dibutyl-di(butyloxy)tin, and that all of the unreacted 1,1,3,3-tetrabutyl-1,3-di(butyloxy)-distannoxane had been recovered. The liquid recovered from the liquid-phase recovery line 120 was transparent and contained 50 ppm of moisture. A dehydration reaction had not occurred.

Example 24

Obtaining Dibutyltin Dialkoxide Using a Column Reactor

Dibutyltin alkoxide was produced in a column reactor 219 such as that illustrated in FIG. 14. A 50 mm inner diameter 4,000 mm total length column reactor 219 made from SUS 316, which was furnished with a low boiling point component recovery line 223, a condenser 224, a separator 225, a back pressure valve 226, a vent line 227, an organic layer circulation line 228, and a water layer recovery line 229 on a reactor upper portion 221, a supply line 214, a supply line 215 and a heat exchanger 216 on a reactor middle portion 220, and a circulation line 217 for circulating reaction solution that has accumulated at a reactor lower portion, a reboiler 218 and an extraction line 230 on a reactor lower portion 222, was packed with Mellapak 750Y (Sulzer Chemtech Ltd., Switzerland). The temperature of the reactor was adjusted using a heater set to 140° C.

A feed pump was used to start feeding the starting material 1,1,3,3-tetrabutyl-1,3-di(butyloxy)-distannoxane prepared in the same manner as in Example 12 from supply line 214 at 280 g/Hr and the reactant 1-butanol (manufactured by Wako Pure Chemical Industries Ltd., Japan, industrial product) from supply line 215 at 1,330 g/Hr. The holding time in the reactor was 6 minutes. Reaction solution which accumulated in the reactor lower portion was circulated at 6,000 g/Hr by the circulation line 217 and the reboiler 218 while heating at a temperature of about 141° C. Low boiling point components flowed from the reactor upper portion 221 and through the low boiling point component recovery line 223 for liquefaction at the condenser 224, and were thereby recovered at 2,000 g/Hr. The organic layer and the water later were slowly separated at the separator 225. The organic layer in the separator 225, i.e. 1-butanol, was returned to the reactor upper portion 221 at 1,994 g/Hr via the organic layer circulation line 228, and the lower layer, which contained a high concentration of water, was recovered at 6 g/Hr from the water layer recovery line 229. From the reactor lower portion 222, the dibutyltin alkoxide-containing component was recovered at 1,604 g/Hr from the extraction line 230. The liquid temperature inside the reactor was 140° C., and the pressure of the back pressure valve 226 was adjusted to 0.096 MPa-G. Continuous supply was continued in this state for 10 hours, after which the system reached a steady state. Analysis of the liquid recovered from the extraction line 230 showed that, using dibutyltin oxide as a reference, the liquid contained a dibutyltin alkoxide consisting of a yield of about 74.2% of dibutyl-di(butyloxy)tin and 25.7% of 1,1,3,3-tetrabutyl-1,3-di(butyloxy)-distannoxane. Tributyltin butoxide had a yield of 0.015%. Meanwhile, the liquid recovered from the water layer recovery line 229 was transparent and had a 90% by weight moisture content. The dehydration rate in the column reactor was 0.33 mol/Hr, which was greater than the value 0.00037 mol/Hr calculated from expression (16).

Figure 1:
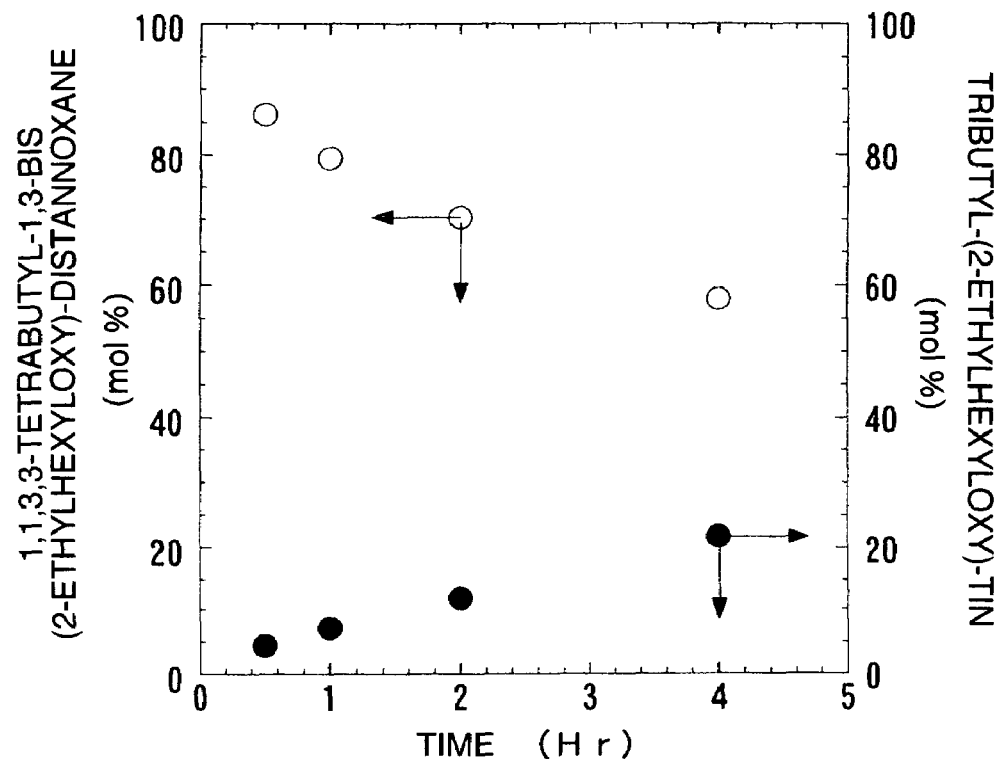
FIG. 1 is a view showing the production of tributyl-(2-ethylhexyloxy)-tin when heating (at 180° C.) 1,1,3,3-tetrabutyl-1,3-bis(2-ethylhexyloxy)-distannoxane.
Figure 2:
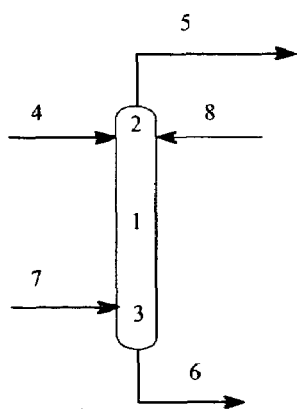
FIG. 2 is a schematic view of one example of column reactors in accordance with the present invention.
Figure 3:
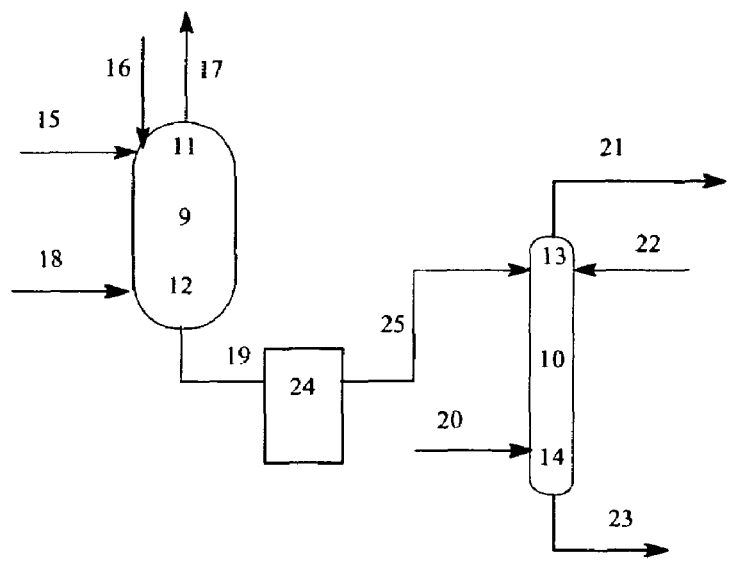
FIG. 3 is a schematic view of one example of combined tank and column reactors in accordance with the present invention.
Figure 4:
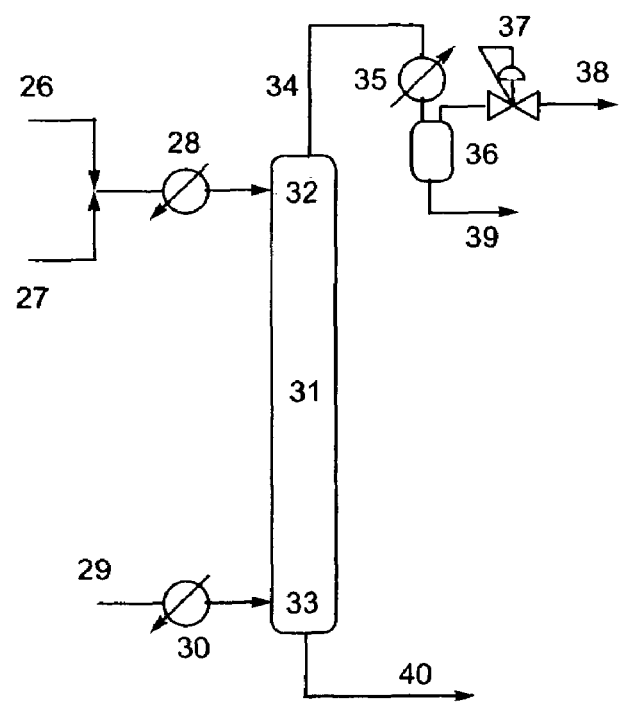
FIG. 4 is a schematic view of another example of column reactors in accordance with the present invention.
Figure 5:
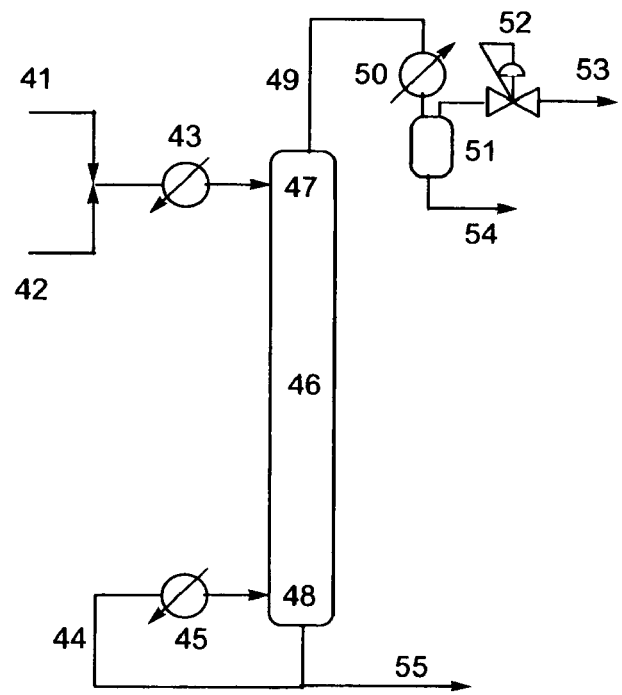
FIG. 5 is a schematic view of still another example of column reactors in accordance with the present invention.
Figure 6:
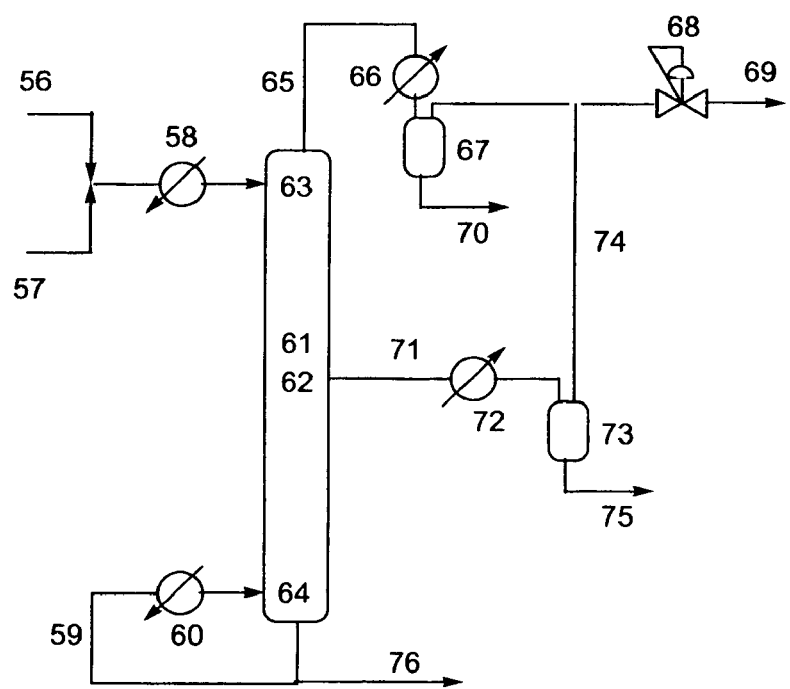
FIG. 6 is a schematic view of still another example of column reactors in accordance with the present invention.
Figure 7:
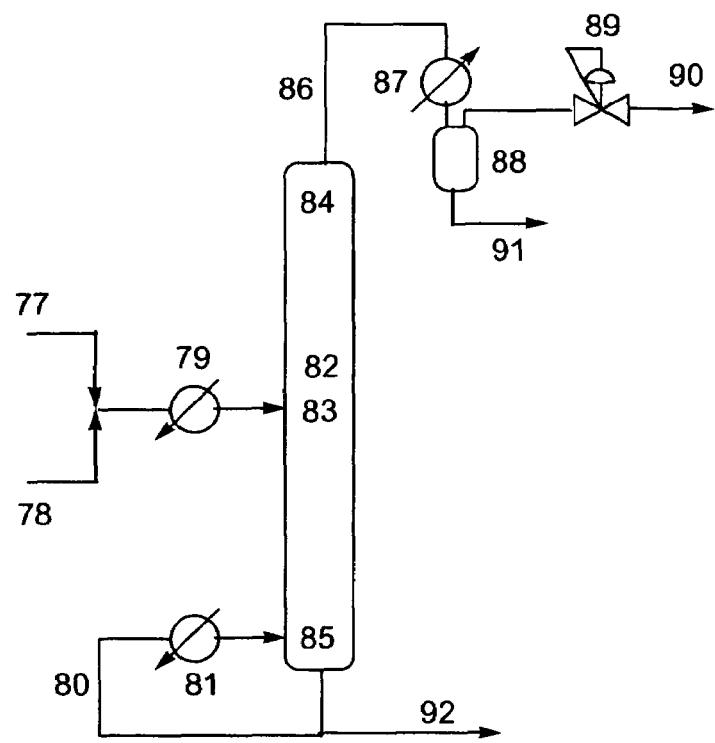
FIG. 7 is a schematic view of another example of column reactors in accordance with the present invention.
Figure 8:
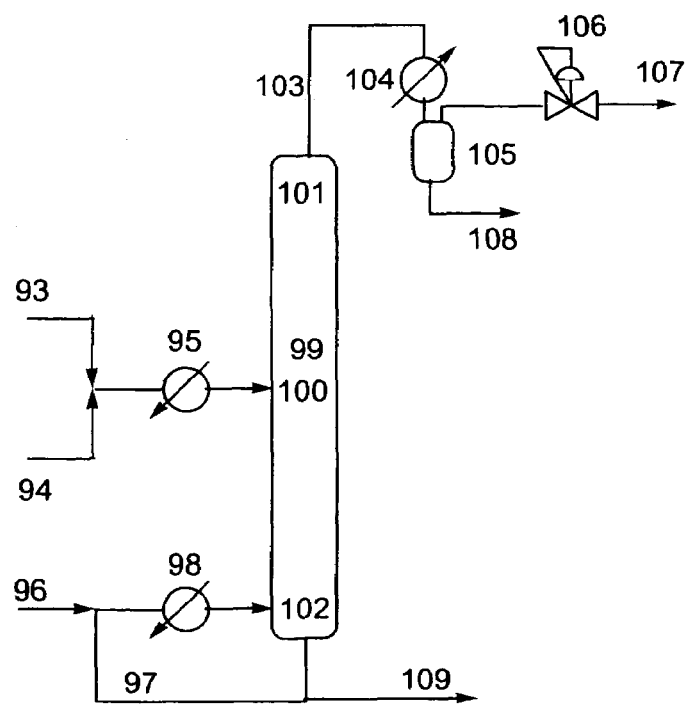
FIG. 8 is a schematic view of still another example of column reactors in accordance with the present invention.
Figure 9:
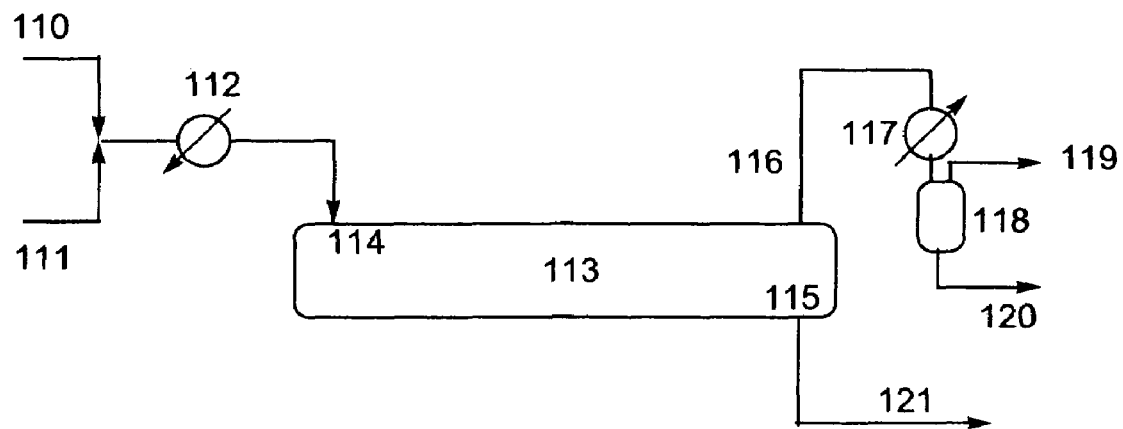
FIG. 9 is a schematic view of one example of horizontal thin film distillation equipment in accordance with the present invention.
Figure 10:
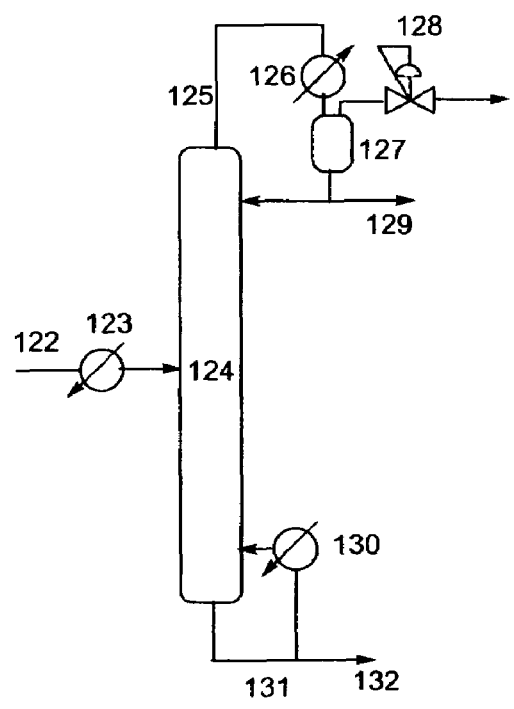
FIG. 10 is a schematic view of one example of continuous multistage distillation columns in accordance with the present invention.
Figure 11:
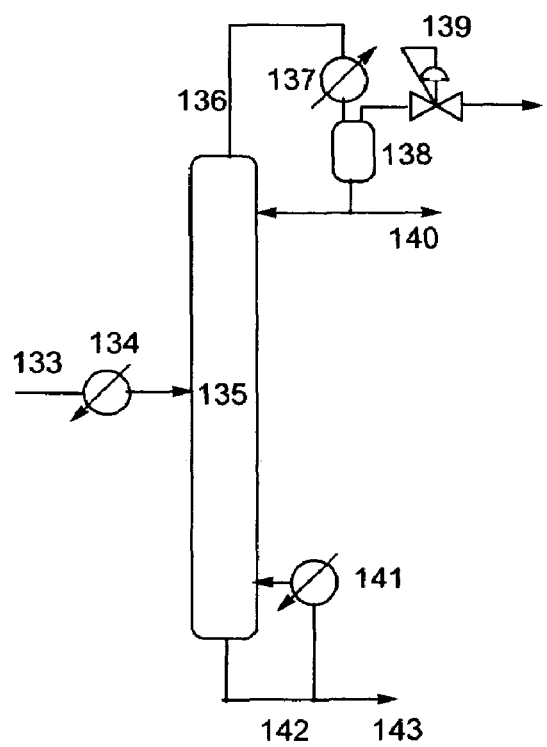
FIG. 11 is a schematic view of another example of continuous multistage distillation columns in accordance with the present invention.
Figure 12:
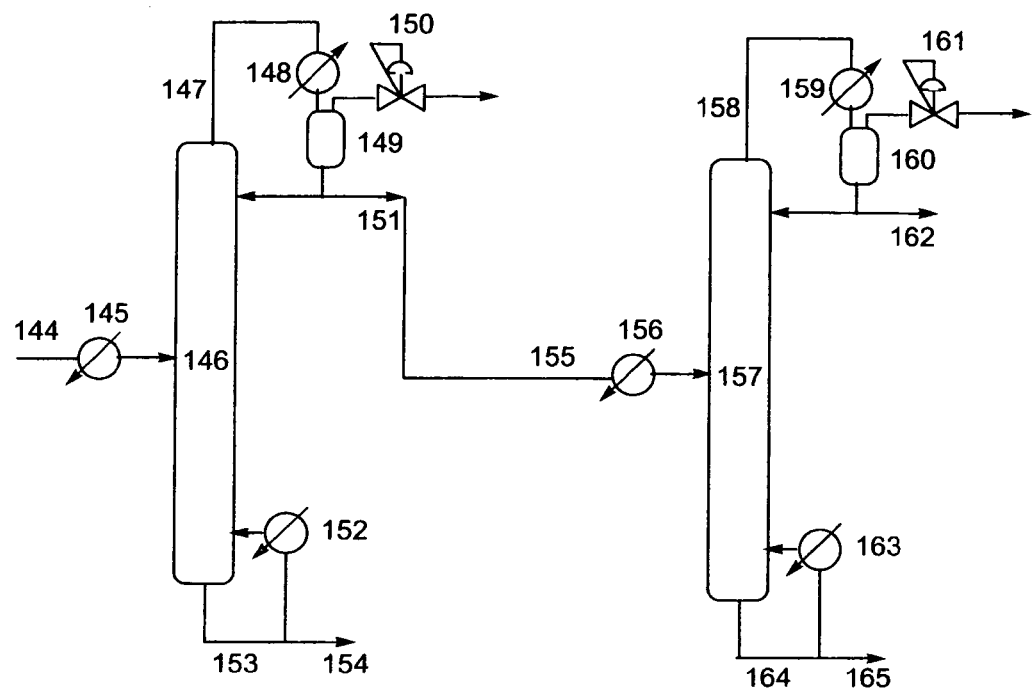
FIG. 12 is a schematic view of still another example of continuous multistage distillation columns in accordance with the present invention.
Figure 13:
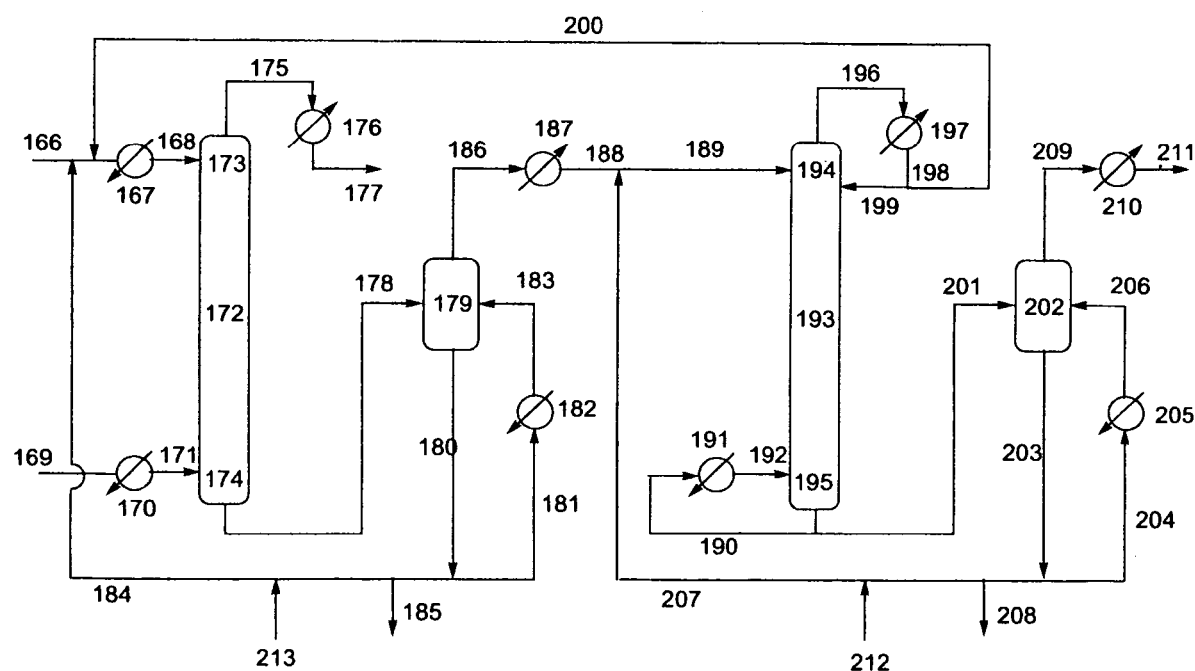
FIG. 13 is a schematic view of still another example of continuous multistage distillation columns in accordance with the present invention.
Figure 14:
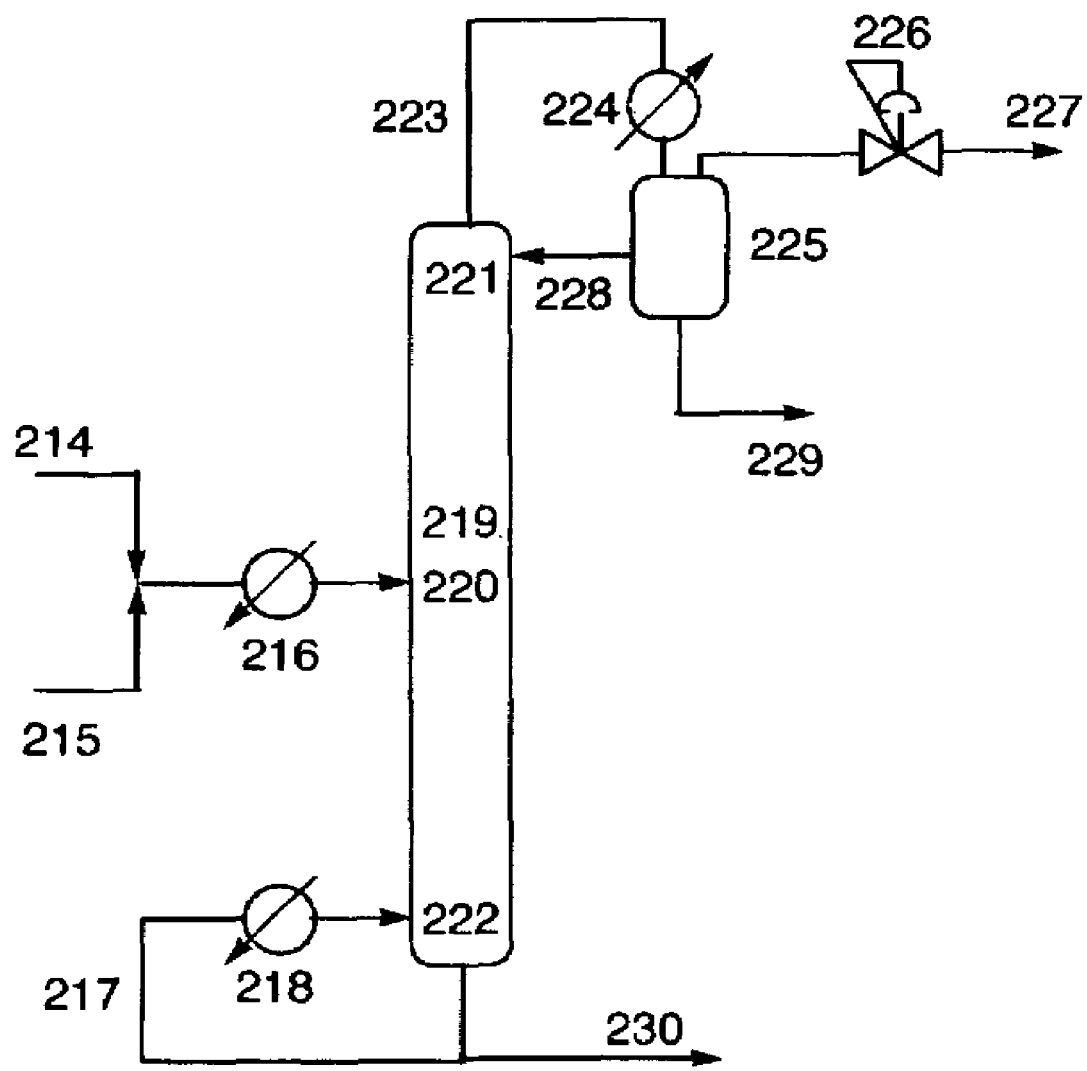
FIG. 14 is a schematic view of another example of column reactors in accordance with the present invention.

The invention claimed is:

1. A process for production of alkyltin alkoxides, comprising subjecting at least one alkyltin compound, as a starting material, which is selected from the group consisting of organotin compounds each having a tin-oxygen-tin bond and a hydroxy compound, as a reactant, to dehydration reaction to produce an alkyltin alkoxide corresponding to the starting material and the reactant, wherein the starting material and the reactant are continuously supplied to a reactor; low boiling point components containing water are taken out from the reactor; and a reaction solution, as a component in the bottom of the reactor, which contains the alkyltin alkoxide is continuously taken out from the reactor.

2. The process according to claim 1, wherein the at least one alkyltin compound, as a starting material, is a tetraalkyl-dialkoxy-1,3-distannoxane and/or a dialkyltin oxide generally existing in the form of a polymer resulting from polymerization via a tin-oxygen-tin bond.

3. The process according to claim 2, wherein the tetraalkyl-dialkoxy-1,3-distannoxane is a tetraalkyl-dialkoxy-1,3-distannoxane represented by the following chemical formula (1):

[Formula 1]

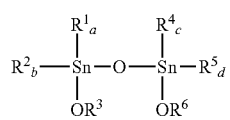

wherein $R^1$, $R^2$, $R^4$ and $R^5$ each independently represent an alkyl group, aralkyl group or aryl group; $R^3$ and $R^6$ each represent an alkyl group or aralkyl group; a and b are integers of 0 to 2, a+b being 2; and c and d are integers of 0 to 2, c+d being 2.

4. The process according to claim 2, wherein the dialkyltin oxide is a polymer of a dialkyltin oxide represented by the following chemical formula (2):

[Formula 2]

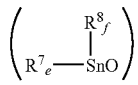
(2)

wherein $R^7$ and $R^8$ each independently represent an alkyl group, aralkyl group or aryl group; and e and f are integers of 0 to 2, e+f being 2.

5. The process according to claim 2, wherein the starting material is any one selected from a monomer, a dimer (aggregate of the same monomer or aggregate of different monomers), an oligomer or a polymer.

6. The process according to claim 1, wherein the hydroxy compound is an alcohol represented by the following chemical formula (3):

[Formula 3]

$$R^9OH \quad (3)$$

wherein $R^9$ represents an n-butyl group, a 2-methylpropyl group, a linear or branched alkyl group with 5 to 12 carbon atoms, a cycloalkyl group with 5 to 12 carbon atoms, a linear or branched alkenyl group with 2 to 12 carbon atoms, a substituted or unsubstituted aryl with 6 to 19 carbon atoms, or an aralkyl group with 7 to 20 carbon atoms that contains an alkyl selected from the group consisting of a linear or branched alkyl with 1 to 14 carbon atoms and a cycloalkyl with 5 to 14 carbon atoms.

7. The process according to claim 6, wherein the alcohol is selected from the group consisting of 1-butanol, 2-methyl-1-propanol and an alkyl alcohol with 5 to 8 carbon atoms.

8. The process according to claim 1, comprising continuously supplying the starting material and the reactant to a reactor to allow them to undergo a dehydration reaction in a liquid phase or in a gas-liquid phase in the reactor; and at the same time, taking out a high boiling point reaction mixture, in the form of a liquid, that contains the produced alkyltin alkoxide or alkyltin alkoxide mixture from the bottom of the reactor, while continuously removing, from the reactor, the produced low boiling point reaction mixture containing water in the form of a gas by distillation.

9. The process according to claim 1, wherein the reactor comprises: lines for supplying the starting material and the reactant, respectively, or a line for supplying the mixed solution of the starting material and the reactant; a line for removing the low boiling point reaction mixture containing water; and a line for taking out the high boiling point reaction mixture.

10. The process according to claim 9, wherein the line for removing the low boiling point reaction mixture containing water is in a position where gas-phase components are removed, while the line for taking out the high boiling point reaction mixture is in a lower position where the liquid-phase component is taken out.

11. The process according to claim 1, wherein the reactor is a tank reactor or a column reactor.

12. The process according to claim 1, wherein the reactor is a type that comprises a stirring tank, a multistage stirring tank, a distillation column, a multistage distillation column, a continuous multistage distillation column, a packed column, a thin film evaporator, a reactor with a support in its inside, a forced circulation reactor, a falling film evaporator, a falling drop evaporator, a trickle bed reactor or a bubble column.

13. The process according to claim 1, wherein an inert gas and/or a gaseous reactant and/or a gaseous inert organic compound and/or an organic solvent that forms an azeotropic mixture with water are supplied to the reactor.

14. The process according to claim 13, wherein the inert gas is selected from nitrogen, carbon dioxide and argon.

15. The process according to claim 1, wherein the dehydration reaction is performed at a temperature in a range of 60° C. to 160° C.

16. The process according to claim 1, wherein a ratio of the total mole number of tin atoms contained in the starting material to the mole number of the reactant, as the ratio of the starting material to the reactant, is in a range of 3 to 100.

17. The process according to claim 4, wherein the dehydration reaction is performed at a dehydration rate represented by the following expression (4):

[Expression 1]

$$\text{Dehydration rate} > \frac{60X + 10Y}{A^{-1} \cdot \exp\left(\frac{B}{R \cdot T}\right)} \quad (4)$$

wherein the dehydration rate means the amount of the water that is formed by the dehydration reaction and drawn out of the system per unit time [mol·hr$^{-1}$]; X represents the total mole number [mol] of tin atoms contained in the alkyltin compound represented by the general formula (2) which is contained in the starting material; Y represents the total mole number [mol] of tin atoms contained in the alkyltin compound represented by the general formula (1) which is contained in the starting material; T represents a temperature [K] at which the dehydration reaction is performed; R represents a gas constant=8.314 J·mol$^{-1}$·K$^{-1}$; and A and B are coefficients depending on the kind of alkyltin compound, wherein coefficients A and B in the expression (4) depend on the kind of alkyltin compound as the starting material and are obtained based on the set primary standard substance; when the starting material contains an alkyltin compound represented by the chemical formula (1), the coefficients A and B represent a frequency factor and an activation energy of a pyrolytic reaction of the primary standard substance which is an alkyltin compound arbitrarily selected from the alkyltin compounds represented by the chemical formula (1) and contained in the starting material, and are obtained from the following equation (5); and when the starting material does not contain an alkyltin compound represented by the chemical formula (1), but contains an alkyltin compound represented by the chemical formula (2), the coefficients A and B represent a frequency factor and an activation energy of a pyrolytic reaction of the primary standard substance which is an alkyltin alkoxide arbitrarily selected from the alkyltin alkoxides represented by the following chemical formula (7) formed from the alkyltin compounds represented by the chemical formula (2) contained in the starting material and the reactant, and are obtained from the following equation (5),

[Expression 2]

$$k = A \cdot \exp\left(-\frac{B}{R \cdot T}\right) \quad (5)$$

wherein k represents a first-order rate constant [hr$^{-1}$]; A represents a frequency factor [hr$^{-1}$]; B represents an activation energy [J·mol$^{-1}$]; R represents a gas constant=8.314 J·mol$^{-1}$·K$^{-1}$; T represents a temperature [K] at which the pyrolitic reaction is performed, and the k represents a first-order rate constant of the pyrolitic reaction which is obtained by the following equation (6):

[Expression 3]

$$k \cdot t = -\ln(1-X) \quad (6)$$

wherein k represents a first-order rate constant [hr$^{-1}$]; t represents a heating time; and X [Hr] represents a reduction ratio [mol/mol] with respect to the initial concentration of a primary standard substance,

[Formula 9]

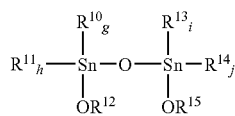

(7)

wherein R$^{10}$, R$^{11}$, R$^{13}$ and R$^{14}$ correspond to either R$^7$ or R$^8$ of the starting material; g, h, i and j correspond to either e or f of the starting material; at least one of R$^{12}$ and R$^{15}$ corresponds to R$^9$ of the reactant; g and h are integers of 0 to 2, g+h=2; and i and j are integers of 0 to 2, i+j=2.

18. A process for production of a carbonate ester characterised by producing a dialkyltin alkoxides by the process according to claim 1 and then using the obtained dialkyltin alkoxide to produce the carbonate ester.

19. The process according to claim 8, wherein the reactor comprises: lines for supplying the starting material and the reactant, respectively, or a line for supplying the mixed solution of the starting material and the reactant; a line for removing the low boiling point reaction mixture containing water; and a line for taking out the high boiling point reaction mixture.

20. The process according to claim 19, wherein the line for removing the low boiling point reaction mixture containing water is in a position where gas-phase components are removed, while the line for taking out the high boiling point reaction mixture is in a lower position where the liquid-phase component is taken out.

21. The process according to claim 20, wherein the reactor is a tank reactor or a column reactor.

22. The process according to claim 21, wherein the reactor is a type that comprises a stirring tank, a multistage stirring tank, a distillation column, a multistage distillation column, a continuous multistage distillation column, a packed column, a thin film evaporator, a reactor with a support in its inside, a forced circulation reactor, a falling film evaporator, a falling drop evaporator, a trickle bed reactor or a bubble column.

23. The process according to claim 22, wherein an inert gas and/or a gaseous reactant and/or a gaseous inert organic compound and/or an organic solvent that forms an azeotropic mixture with water are supplied to the reactor.

24. The process according to claim 23, wherein the inert gas is selected from nitrogen, carbon dioxide and argon.

25. The process according to claim 16, wherein the dehydration reaction is performed at a dehydration rate represented by the following expression (4):

[Expression 1]

$$\text{Dehydration rate} > \frac{60X + 10Y}{A^{-1} \cdot \exp\left(\frac{B}{R \cdot T}\right)} \quad (4)$$

wherein the dehydration rate means the amount of the water that is formed by the dehydration reaction and drawn out of the system per unit time [mol·hr$^{-1}$]; X represents the total mole number [mol] of tin atoms contained in the alkyltin compound represented by the general formula (2) which is contained in the starting material; Y represents the total mole number [mol] of tin atoms contained in the alkyltin compound represented by the general formula (1) which is contained in the starting material; T represents a temperature [K] at which the dehydration reaction is performed; R represents a gas constant =8.314 J·mol$^{-1}$·K$^{-1}$; and A and B are coefficients depending on the kind of alkyltin compound, wherein coefficients A and B in the expression (4) depend on the kind of alkyltin compound as the starting material and are obtained based on the set primary standard substance; when the starting material contains an alkyltin compound represented by the chemical formula (1), the coefficients A and B represent a frequency factor and an activation energy of a pyrolytic reaction of the primary standard substance which is an alkyltin compound arbitrarily selected from the alkyltin compounds represented by the chemical formula (1) and contained in the starting material, and are obtained from the following equation (5); and when the starting material does not contain an alkyltin compound represented by the chemical formula (1), but contains an alkyltin compound represented by the chemical formula (2), the coefficients A and B represent a frequency factor and an activation energy of a pyrolytic reaction of the primary standard substance which is an alkyltin alkoxide arbitrarily selected from the alkyltin alkoxides represented by the following chemical formula (7) formed from the alkyltin compounds represented by the chemical formula (2) contained in the starting material and the reactant, and are obtained from the following equation (5),

[Expression 2]

$$k = A \cdot \exp\left(-\frac{B}{R \cdot T}\right) \quad (5)$$

wherein k represents a first-order rate constant [hr$^{-1}$]; A represents a frequency factor [hr$^{-1}$]; B represents an activation energy [J·mol$^{-1}$]; R represents a gas constant =8.314 J·mol$^{-1}$·K$^{-1}$; T represents a temperature [K] at which the pyrolitic reaction is performed, and the k represents a first-order rate constant of the pyrolitic reaction which is obtained by the following equation (6):

[Expression 3]

$$k \cdot t = -\ln(1-X) \quad (6)$$

wherein k represents a first-order rate constant [hr$^{-1}$]; t represents a heating time; and X [Hr] represents a reduction ratio [mol/mol] with respect to the initial concentration of a primary standard substance,

[Formula 9]

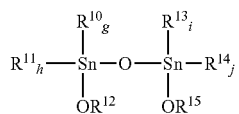

(7)

wherein $R^{10}$, $R^{11}$, $R^{13}$ and $R^{14}$ correspond to either $R^7$ or $R^8$ of the starting material; g, h, i and j correspond to either e or f of the starting material; at least one of $R^{12}$ and $R^{15}$ corresponds to $R^9$ of the reactant; g and h are integers of 0 to 2, g+h =2; and i and j are integers of 0 to 2, i+j=2.

26. A process for production of a carbonate ester characterised by producing a dialkyltin alkoxides by the process according to claim 25 and then using the obtained dialkyltin alkoxide to produce the carbonate ester.

* * * * *

UNITED STATES PATENT AND TRADEMARK OFFICE
CERTIFICATE OF CORRECTION

PATENT NO. : 7,541,482 B2
APPLICATION NO. : 11/596885
DATED : June 2, 2009
INVENTOR(S) : Nobuhisa Miyake et al.

It is certified that error appears in the above-identified patent and that said Letters Patent is hereby corrected as shown below:

Column 1, Line 4, change "REFERANCE" to --REFERENCE--.

Column 1, Line 11, change "referance." to --reference.--.

Column 71, Line 12, change "pyrolitic" to --pyrolytic--.

Column 71, Line 13, change "pyrolitic" to --pyrolytic--.

Column 72, Line 62, change "pyrolitic" to --pyrolytic--.

Column 72, Line 63, change "pyrolitic" to --pyrolytic--.

Column 74, Line 1, change "$R^{10,}\ R^{11,}\ R^{13}$" to --$R^{10},\ R^{11},\ R^{13}$--.

Signed and Sealed this

Eighteenth Day of August, 2009

David J. Kappos
*Director of the United States Patent and Trademark Office*